(12) United States Patent
Ramcharan et al.

(10) Patent No.: US 11,479,753 B2
(45) Date of Patent: Oct. 25, 2022

(54) HIERARCHICALLY STRUCTURED PROTEIN MATERIALS FOR THREE DIMENSIONAL (3D) CELLULAR SUPPORT SYSTEMS

(71) Applicant: THE REGENTS OF THE UNIVERSITY OF MICHIGAN, Ann Arbor, MI (US)

(72) Inventors: Stacy Ramcharan, Ann Arbor, MI (US); Luis Solorio, West Lafayette, IN (US); Jacob Jordahl, Chaska, MN (US); Joerg Lahann, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 585 days.

(21) Appl. No.: 16/300,499

(22) PCT Filed: May 11, 2017

(86) PCT No.: PCT/US2017/032197
§ 371 (c)(1),
(2) Date: Nov. 9, 2018

(87) PCT Pub. No.: WO2017/197138
PCT Pub. Date: Nov. 16, 2017

(65) Prior Publication Data
US 2019/0144818 A1   May 16, 2019

Related U.S. Application Data

(60) Provisional application No. 62/334,865, filed on May 11, 2016.

(51) Int. Cl.
*C12N 5/00* (2006.01)

(52) U.S. Cl.
CPC ........ *C12N 5/0062* (2013.01); *C12N 2533/00* (2013.01); *C12N 2533/14* (2013.01);
(Continued)

(58) Field of Classification Search
CPC ............ C12N 2533/40; C12N 2535/00; C12N 2533/00; C12N 2533/54; C12N 2533/30; C12N 2533/52; C12N 5/0062
See application file for complete search history.

(56) References Cited

U.S. PATENT DOCUMENTS

| 3,959,079 A | 5/1976 | Mareschi et al. |
| 5,858,721 A | 1/1999 | Naughton et al. |

(Continued)

FOREIGN PATENT DOCUMENTS

| EP | 0097907 A2 | 1/1984 |
| JP | 2012213390 A | 11/2012 |

(Continued)

OTHER PUBLICATIONS

Chen et al. Culturing of skin fibroblasts in a thin PLGA-collagen hybrid mesh. Biomaterials 26 (2005) 2559-2566 (Year: 2005).*
(Continued)

*Primary Examiner* — Taeyoon Kim
(74) *Attorney, Agent, or Firm* — Harness, Dickey & Pierce, P.L.C.

(57) ABSTRACT

A cellular support system comprises a three-dimensional scaffold structure comprising at least one void. At least one suspended protein bridge spans across the at least one void in the three-dimensional scaffold structure. The suspended protein bridge is capable of supporting cells and promotes three-dimensional cellular growth. In certain aspects, the protein in the suspended protein bridge is an extracellular matrix protein, such as collagens, laminins, fibronectins, and combinations thereof. Such a cellular support system sup-
(Continued)

ports thriving cell cultures in three-dimensions emulating cell growth in vivo in an extracellular matrix, including promoting cell remodeling. Methods for making such cellular support systems are also provided.

33 Claims, 28 Drawing Sheets

(52) U.S. Cl.
CPC ...... *C12N 2533/30* (2013.01); *C12N 2533/40* (2013.01); *C12N 2533/52* (2013.01); *C12N 2533/54* (2013.01); *C12N 2533/78* (2013.01); *C12N 2535/00* (2013.01)

(56) References Cited

U.S. PATENT DOCUMENTS

| | | | |
|---|---|---|---|
| 8,039,258 B2 | 10/2011 | Harris et al. | |
| 2006/0252981 A1* | 11/2006 | Matsuda | A61L 31/00 600/37 |
| 2008/0194010 A1 | 8/2008 | Liu | |
| 2009/0043079 A1 | 2/2009 | Chen et al. | |
| 2009/0148486 A1 | 6/2009 | Lu et al. | |
| 2009/0238853 A1 | 9/2009 | Liu et al. | |
| 2015/0037432 A1* | 2/2015 | Malinin | A61K 35/36 424/549 |

FOREIGN PATENT DOCUMENTS

| | | | |
|---|---|---|---|
| WO | 2012094611 A1 | 7/2012 | |
| WO | 2013040078 A2 | 3/2013 | |
| WO | WO-2015005349 A1 | 1/2015 | |
| WO | WO-2016042211 A1 * | 3/2016 | ......... A61L 27/3654 |

OTHER PUBLICATIONS

Zhang et al. Influence of surgical suture properties on the tribological interactions with artificial skin by a capstan experiment approach. Friction 5(1): 87-98 (2017) (Year: 2017).*
Lodish et al. Section 22.3 Collagen: The Fibrous Proteins of the Matrix. Molecular Cell Biology. 4th edition. New York: W. H. Freeman, p. 1-6 (Year: 2000).*
Mitsi et al. The ultrastructure of fibronectin fibers pulled from a proteinmonolayer at the air-liquid interface and the mechanism of the sheet-to-fiber transition. Biomaterials. Jan. 2015; 36: 66-79. (Year: 2015).*
Extended European Search Report for European Patent Application No. 17796855.9 dated Nov. 14, 2019, 9 pages.
Sabater i Serra, Roser et al., "Role of chemical crosslinking in material-driven assembly of fibronectin (nano)networks: 2D surfaces and 3D scaffolds," Colloids and Surfaces. B: Biointerfaces, vol. 148 (Published Jan. 31, 2016), pp. 324-332; ISSN: 0927-7765; DOI: 10.1016/J.COLSURFB.2016.08.044.
Capulli, A.K. et al.,: "Fibrous scaffolds for building hearts and heart parts", Advanced Drug Delivery Reviews, vol. 96, pp. 83-102 (Published online Dec. 4, 2015); ISSN: 0169-409X; DOI: 10.1016/J.ADDR.2015.11.020.
Li, D. et al., "Electrospinning Nanofibers as Uniaxially Aligned Arrays and Layer-by-Layer Stacked Films," Advanced Materials, vol. 16, No. 4, pp. 361-366 (Published Feb. 17, 2014); ISSN: 0935-9648; DOI: 10.1002/ADMA.200306226.
International Search Report and Written Opinion issued in PCT/US2017/032197, dated May 11, 2017; ISA/US.
Ahmed, Z. et al., "Nerve Guide Material Made from Fibronectin Assessment of in Vitro Properties," *Tissue Engineering* (2003), 9, 2, pp. 219-231.
Ahmed, Zubair et al., "Stabilization of fibronectin mats with micromolar concentrations of copper," *Biomaterials* (1999), 20, pp. 201-209.

Ahn, Seungkuk et al., "Self-Organizing Large-Scale Extracellular-Matrix Protein Networks," *Adv. Mater.* (Mar. 31, 2015), 27, pp. 2838-2845.
Baneyx, Gretchen et al., "Fibronectin extension and unfolding within cell matrix fibrils controlled by cytoskeletal tension," *PNAS* (Apr. 16, 2002), 99, 8, pp. 5139-5143.
Bhaskar, Srijanani et al., "Microstructured Materials Based on Multicompartmental Fibers," *JACS* (Apr. 29, 2009), 131, 19, pp. 6650-6651.
Brown, Robert A. et al., "Preparation of orientated fibrous mats from fibronectin: composition and stability," *Biomaterials* (1994), 15, 6, pp. 457-464.
Chang et al., "A laminin 511 matrix is regulated by TAZ and functions as the ligand for the alpha6Bbeta1 integrin to sustain breast cancer stem cells," *Molecular, Cell and Cancer Biology Publications* (2015), 22, 9 pages.
Deravi, Leila F. et al., "Differential Contributions of Conformation Extension and Domain Unfolding to Properties of Fibronectin Nanotextiles," *Nano Lett.* (Oct. 8, 2012), 12, pp. 5587-5592.
Ejim, Obiora S. et al., "Production of artificial-orientated mats and strands from plasm fibronectin: a morphological study," *Biomaterials* (1993), 1, 10, pp. 743-748.
Flynn, L.E., "The use of decellularized adipose tissue to provide an inductive microenvironment for the adipogenic differentiation of human adipose-derived stem cells," *Biomaterials* (2010), 31, pp. 4715-4724.
Ginestier, et al., "ALDH1 Is a Marker of Normal and Malignant Human Mammary Stem Cells and a Predictor of Poor Clinical Outcome," *Cell Stem Cell* (Nov. 14, 2007), 1, pp. 555-567 (2007).
Guan, Jingjiao et al., "Simultaneous fabrication of hybrid arrays of nanowires and micro/nanoparticles by dewetting on micropillars," *Soft Matter*, (Aug. 31, 2007), 3, pp. 1369-1371.
Kaiser, Peter et al., "Differential adhesion of fibroblast and neuroblastoma cells on size- and geometry-controlled nanofibrils of the extracellular matrix," *Soft Matter* (Oct. 12, 2009), 6, pp. 113-119.
Klotzsch, Enrico et al., "Fibronectin forms the most extensible biological fibers displaying switchable force-exposed cryptic binding sites," *PNAS* (Oct. 27, 2009), 106, 43, pp. 18267-18272.
Lee, Jungwoo et al., "Three-Dimensional Cell Culture Matrices: State of the Art," *Tissue Engineering: Part B* (2008), 14, 1, pp. 61-86.
Little, William C. et al., "Assay to mechanically tune and optically probed fibrillar fibronectin conformations from fully relaxed to breakage," *Matrix Biology* (2008), 27, pp. 451-461.
Mao, Yong et al., "Fibronectin fibrillogenesis, a cell-mediated matrix assembly process," *Matrix Biology* (2005), 24, pp. 389-399.
Mitsi, Maria et al., "The ultrastructure of fibronectin fibers pulled from a protein monolayer at the air-liquid interface and the mechanism of the sheet-to-fiber transition," *Biomaterials* (Oct. 13, 2014), 36, pp. 66-79.
Oberdörfer, York et al., "Conformational Analysis of Native Fibronectin by Means of Force Spectroscopy," *Langmuir* (2000), 76, pp. 9955-9958.
Pabba, Santosh et al., "Biopolymerization-driven self-assembly of nanofiber air-bridges," *Soft Matter* (Feb. 3, 2009), 5, pp. 1378-1385.
Paget, Stephen, "The Distribution of Secondary Growths in Cancer of the Breast," *The Lancet* (Mar. 23, 1889), 133, 3421, pp. 571-573.
Pham, Quynh P. et al., "Electrospinning of Polymeric Nanofibers for Tissue Engineering Application: A Review," *Tissue Engineering*, (2006), 12, 5, pp. 1197-1211.
Schwarzbauer, Jean E. et al., "Fibronectin fibrillogenesis: a paradigm for extracellular matrix assembly," *Curr. Opin. Cell Biol.* (1999), 11, pp. 622-627.
Simon, Karen A. et al., "Polymer-based mesh as supports for multi-layered 3D cell culture and assays" *Biomaterials* (Oct. 2, 2013), 35, 1, pp. 259-268.
Ulmer, J., Geiger, B. & Spatz, J.P. Force-induced fibronectin fibrillogenesis in vitro. Soft Matter 4, 1998-2007 (2008).
Wierzbicka-Patynowski, Iwona et al., "The ins and outs of fibronectin matrix assembly," *Journal of Cell Science*, (Aug. 15, 2003), 116, pp. 3269-3276.

(56) References Cited

OTHER PUBLICATIONS

Yoo, Sang Jin et al., "Simple and Novel Three Dimensional Neuronal Cell Culture Using a Micro Mesh Scaffold," *Experimental Neurobiology* (Jun. 2011), 20, 2, pp. 110-115.

Kaity, Santanu et al., "Microsponges: A Novel Strateg for Drug Delivery System"; Journal of Advanced Pharmaceutical Technology and Research; Jul.-Sep. 2010; vol. 1; Issue 3; pp. 283-290.

Jordahl, Stacy et al.; "Engineered Fibrillar Fibronectin Networks as Three-Dimensional Tissue Scaffolds;" Advanced Materials Communication 31(16); (Nov. 15, 2019, first published Sep. 30, 2019); (https://doi.org/10.1002/adma.201904580); 10 pages.

https://en.wiktionary.org/wiki/microsponge <https://protect-us.mimecast.com/s/fLobCERZ81HlojGwcNLUvF>; accessed on Jan. 12, 2022; 1 page.

\* cited by examiner

US 11,479,753 B2

HIERARCHICALLY STRUCTURED PROTEIN MATERIALS FOR THREE DIMENSIONAL (3D) CELLULAR SUPPORT SYSTEMS

CROSS-REFERENCE TO RELATED APPLICATIONS

This application is the U.S. National Phase Application under 35 U.S.C. 371 of International Application No. PCT/US2017/032197 filed on May 11, 2017, which claims the benefit of U.S. Provisional Application No. 62/334,865 filed on May 11, 2016. The entire disclosure disclosures of the above applications are incorporated herein by reference.

GOVERNMENT SUPPORT

[0001.1] This invention was made with government support under CA198929 awarded by the National Institutes of Health. The Government has certain rights in the invention.

FIELD

The present disclosure relates to hierarchically structured protein material for three-dimensional cellular support systems and methods for making such cellular support systems.

BACKGROUND

This section provides background information related to the present disclosure which is not necessarily prior art.

The nano- and microstructure of the cellular microenvironment is a decisive factor related to many biological phenomena important for regenerative medicine and biomedical research, such as cell morphology, adhesion, motility, or apoptosis. In vivo, nearly all tissue cells are found in an extracellular matrix comprising a complex three-dimensional fibrous mesh with a distribution of fibers and voids (including various extracellular proteins) that enable complex biochemical and physical signaling by cells. Mimicking such architecture could facilitate robust three-dimensional growth that accurately emulates cell growth in vivo. Conventional techniques for cell growth and manipulation have primarily been limited to 2-dimensional surfaces, which have been insufficient for emulating cell growth in a complex three-dimensional environment due to lack of the necessary structural architecture and materials. In spite of the importance of multidimensional scaffolding and patterning for biological applications, their realization, especially with biomedically relevant polymers, has been challenging. Because the local microstructure plays a pivotal role for many biological functions, a wide range of methods have been developed to design precisely engineered substrates for both fundamental biological studies and biotechnological applications.

Use of proteins in scaffolds could help better guide three-dimensional cellular growth, but has only met with limited success. Current protein adsorption systems include a solid flat substrate which is incubated in a solution of proteins allowing a certain amount of time in which the proteins adsorb onto the surface to form a conformal coating. Proteins adsorbed onto a solid substrate are not well-suited for cell culture applications due to a lack of three-dimensionality, porosity, and extremely high Young's moduli compared to physiological conditions. No technology currently exists which adequately simulates the natural three-dimensional extracellular matrix or allows the formation of a suspended proteins with control over composition and overall morphology. Thus, it would be desirable to have a cellular support scaffold system that includes one or more biocompatible materials and a suspended protein that facilitates robust cell growth and proliferation in three-dimensions, while providing control over composition and morphology.

SUMMARY

This section provides a general summary of the disclosure, and is not a comprehensive disclosure of its full scope or all of its features.

In various aspects, the present disclosure provides a cellular support system. The system optionally comprises a three-dimensional scaffold structure comprising at least one void. At least one suspended protein bridge spans across the at least one void in the three-dimensional scaffold structure. The suspended protein bridge is capable of supporting cells and promotes three-dimensional cellular growth.

In one variation, the void has a major dimension of greater than or equal to about 0.1 micrometers to less than or equal to about 5 centimeters.

In one variation, the suspended protein bridge comprises one or more extracellular proteins.

In one variation, the suspended protein bridge comprises one or more extracellular matrix proteins.

In one variation, the suspended protein bridge comprises one or more proteins selected from the group consisting of: collagens, laminins, fibronectins, tenascins, elastin, vitronectin, periostin, and combinations thereof.

In one variation, the three-dimensional scaffold structure is formed from a material selected from the group consisting of: a metal material, a polymeric material, a composite material, a ceramic material, a biologically-derived material, and combinations thereof.

In one variation, the three-dimensional scaffold structure comprises a polymer and is formed from a polymeric precursor or is a polymer selected from the group consisting of: polylactic acid, polyglycolide, polycaprolactone, poly(lactide-co-glycolide), poly(lactide-co-caprolactone), polyethylene glycol, starches, polydimethylsiloxane, polyurethanes, polyolefins, polyamides, celluloses, lignins, biodegradable polyesters, polystyrene, and combinations thereof.

In one variation, the three-dimensional scaffold structure has a rough surface that defines the at least one void, wherein an average surface roughness ($R_a$) of the rough surface is greater than or equal to about 0.025 micrometers.

In one variation, the three-dimensional scaffold structure comprises a polymer and a protein loading density in the cellular support system is less than or equal to about 8 milligrams of protein per milligram of polymer.

In one variation, the at least one void comprises a plurality of distinct suspended protein bridges spanning across the at least one void in the three-dimensional scaffold structure.

In one variation, at least two regions of a wall of the three-dimensional scaffold structure defining the void are coated with a protein so as to anchor a first end of the suspended protein bridge and a second end of the suspended protein bridge within the void.

In other aspects, the present disclosure provides a cellular support system that comprises a three-dimensional scaffold structure comprising a plurality of voids. Multiple voids of the plurality of voids in the three-dimensional scaffold structure may respectively comprise distinct suspended protein bridges. Each suspended protein bridge is capable of supporting cells and promotes three-dimensional cellular growth within the respective void in the plurality.

In one variation, a wall is defined between two of the plurality of voids having an average thickness of greater than or equal to about 0.025 micrometers.

In one variation, a wall is defined between two of the plurality of voids having an average thickness of greater than or equal to about 0.5 micrometers to less than or equal to about 300 micrometers.

In one variation, at least two regions of a wall defining each void of the plurality are coated with a protein so as to anchor a first end of the suspended protein bridge and a second end of the suspended protein bridge within the void.

In one variation, the void has a major dimension of greater than or equal to about 0.1 micrometers to less than or equal to about 5 centimeters.

In one variation, the three-dimensional scaffold structure has a rough surface that defines the plurality of voids, wherein an average surface roughness ($R_a$) of the rough surface is greater than or equal to about 0.025 micrometers.

In one variation, the suspended protein bridge comprises one or more extracellular proteins.

In one variation, the suspended protein bridge comprises one or more extracellular matrix proteins.

In one variation, the suspended protein bridge comprises one or more proteins selected from the group consisting of: collagens, laminins, fibronectins, elastin, vitronectin, periostin, and combinations thereof.

In one variation, the three-dimensional scaffold structure is formed from a material selected from the group consisting of: a metal material, a polymeric material, a composite material, a ceramic material, a biologically-derived material, and combinations thereof.

In one variation, the three-dimensional scaffold structure comprises a polymer and is formed from a polymeric precursor or is a polymer selected from the group consisting of: polylactic acid, polyglycolide, polycaprolactone, poly (lactide-co-glycolide), poly(lactide-co-caprolactone), polyethylene glycol, starches, polydimethylsiloxane, polyurethanes, polyolefins, polyamides, celluloses, lignins, biodegradable polyesters, polystyrene, and combinations thereof.

In one variation, the three-dimensional scaffold structure comprises a polymer and a protein loading density in the cellular support system is less than or equal to about 8 milligrams of protein per milligram of polymer.

In one variation, each void of the plurality of voids respectively comprises a distinct suspended protein bridge.

In yet other aspects, the present disclosure provides a method of making a cellular support system. The method comprises positioning a three-dimensional scaffold structure comprising at least one void in a container at a two-phase interface comprising a liquid comprising a protein and a fluid. The method also includes passing liquid past the three-dimensional scaffold structure to dynamically incubate the protein so as to form a suspended protein bridge spanning across the at least one void. The suspended protein bridge is capable of supporting cells and promotes three-dimensional cellular growth.

In one variation, the passing comprises moving the three-dimensional scaffold structure so that the liquid flows past the three-dimensional scaffold structure, wherein the moving is selected from the group consisting of: orbital rotation, tumbling rotation, vibration, shaking, and combinations thereof.

In one variation, the fluid is a gas that comprises air.

In one variation, the passing occurs for greater than or equal to about 5 minutes to less than or equal to about 24 hours.

In one variation, the liquid comprising protein is a protein solution having a concentration of protein from about 0.01 mg/mL to about 1 mg/mL.

In one variation, the protein comprises one or more extracellular proteins.

In one variation, the protein comprises one or more extracellular matrix proteins.

In one variation, the protein is selected from the group consisting of: collagens, laminins, fibronectins, tenascins, elastin, vitronectin, periostin, and combinations thereof.

In one variation, the three-dimensional scaffold structure is formed from a material selected from the group consisting of: a metal material, a polymeric material, a composite material, a ceramic material, a biologically-derived material, and combinations thereof.

In one variation, the three-dimensional scaffold structure comprises a polymer and is formed from a polymeric precursor or is a polymer selected from the group consisting of: polylactic acid, polyglycolide, polycaprolactone, poly (lactide-co-glycolide), poly(lactide-co-caprolactone), polyethylene glycol, starches, polydimethylsiloxane, polyurethanes, polyolefins, polyamides, celluloses, lignins, biodegradable polyesters, polystyrene, and combinations thereof.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figures 4A, 4B, 4C, 4D:
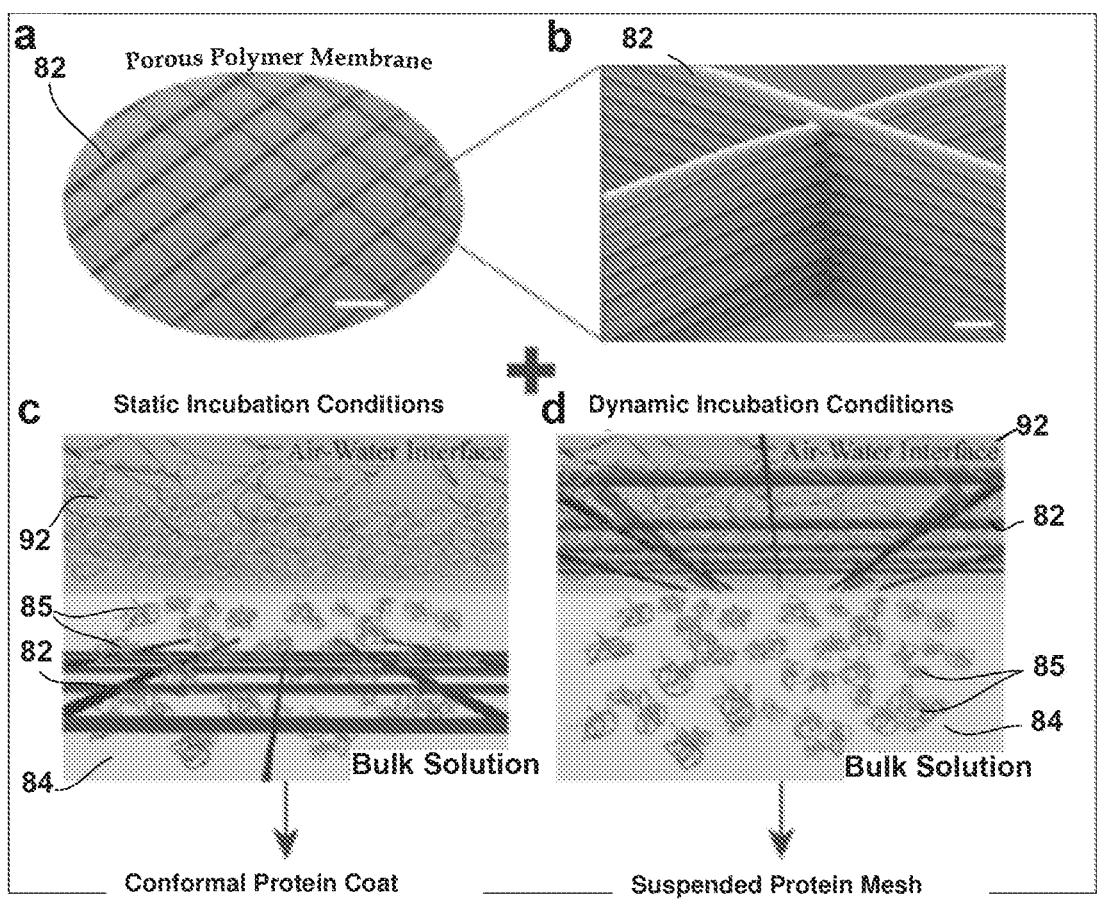

FIGS. 4A-4D. FIG. 4A shows a scanning electron microscope (SEM) of a three-dimensional scaffold structure having a plurality of voids in the form of a porous polymer membrane. FIG. 4B is an SEM showing a detailed view from FIG. 4B taken from the circled region. The scale bars are 500 μm and 25 μm in FIGS. 4A and 4B respectively. FIG. 4C shows a static incubation process for a three-dimensional scaffold structure like that in FIGS. 4A-4B, while FIG. 4D shows a dynamic incubation process for a three-dimensional scaffold structure like that in FIGS. 4A-4B in accordance with certain aspects of the present disclosure.

Figures 5A, 5B, 5C, 5D, 5E, 5F:
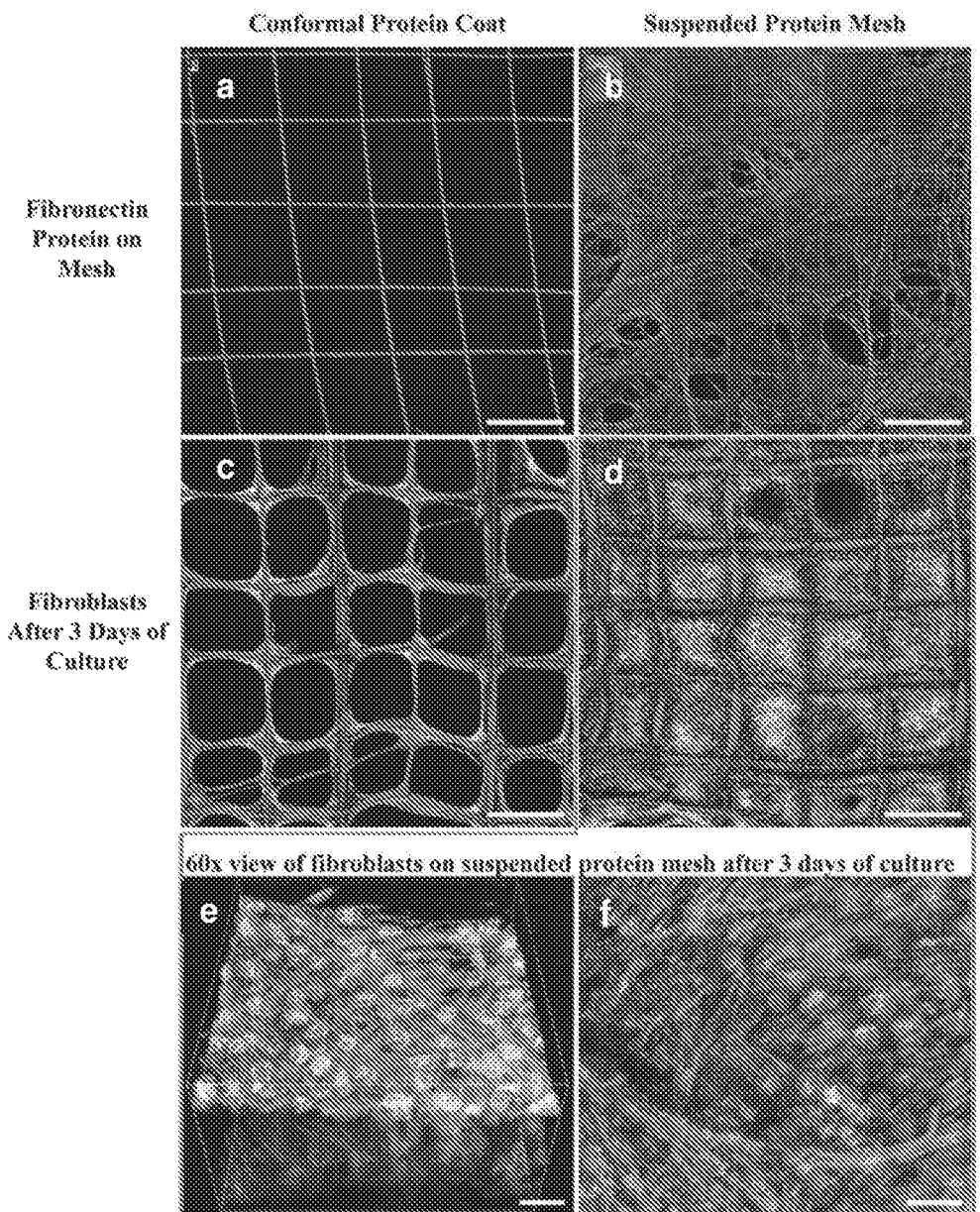

FIGS. 5A-5F. FIG. 5A shows a laser scanning confocal microscopy (LSCM) image of a conformal protein coat resulting from static incubation of a porous polymer scaffold in fibronectin protein solution. FIG. 5B shows an LSCM image of a suspended protein mesh formed within open pores of a porous polymer scaffold after incubation at the air-water interface under dynamic conditions. FIG. 5C shows culturing NIH-3T3 fibroblasts on conformal fibronectin coats like in FIG. 5A. FIG. 5D shows culturing of NIH-3T3 fibroblasts on suspended fibronectin protein mesh like in FIG. 5B. FIG. 5E shows a 3D volume view showing depth of tissue created by cells in culture on a suspended protein bridge mesh in a cell culture scaffold formed in accordance with certain aspects of the present disclosure. FIG. 5F shows a top view of the same cell culture scaffold as in FIG. 5E showing interconnectivity of cells on suspended protein mesh. Channels: blue, polymer microfibers; green, fibronectin; red, actin; cyan, cell nucleus. Scale bars: FIGS. 5A-5D are 500 μm and FIGS. 5E-5F are 25 μm.

Figures 6A, 6B, 6C, 6D:
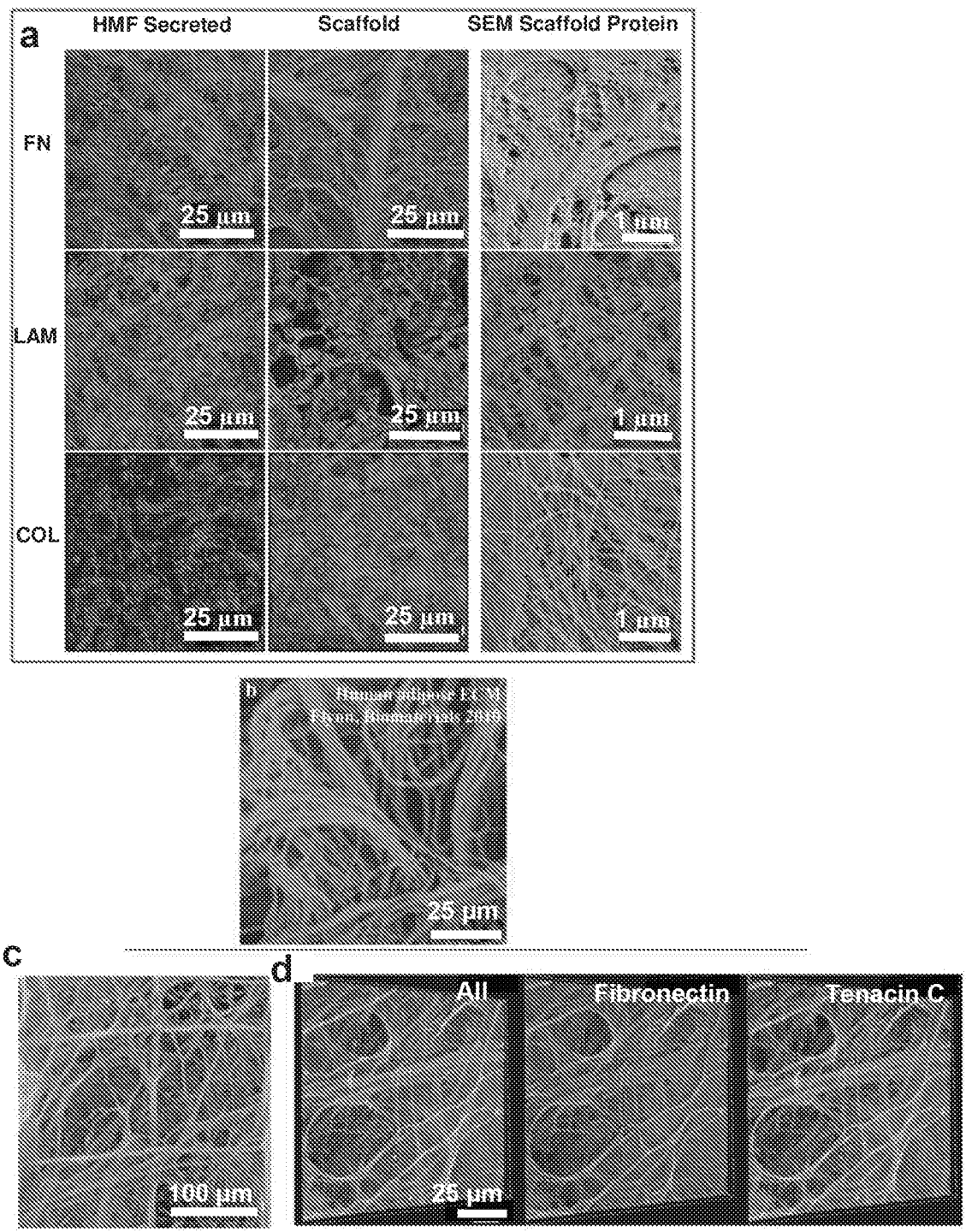

FIGS. 6A-6D show suspended protein bridge meshes in different cell culture scaffolds according to certain aspects of the present disclosure can be made with a large variety of proteins. FIG. 6A shows a left column having fibronectin (FN), laminin (LAM), or collagen (COL) as secreted by human mammary fibroblasts when cultured on tissue culture scaffold formed of polystyrene. The middle column of FIG. 6A is FN, LAM, and COL as suspended on 3D jet writing scaffolds. The right column are SEM images of FN, LAM, and COL fibrils as suspended on 3D jet writing scaffolds shown at 10,000× magnification. The left and middle columns are imaged by LSCM at 60× magnification, with scale bars of 25 μm. The right column has a scale bar of 1 μm. FIG. 6B shows a comparative SEM representative image of decellularized human adipose tissue revealing the fibrous morphology of physiological human tissue. FIG. 6C is a zoomed out view showing a larger scale visualization of fibronectin in mixture with tenascin c. FIG. 6D shows a 60× magnified view of both fibronectin and tenascin c (all), fibronectin alone, and tenascin c alone suspended mesh as shown in FIG. 6C.

Figures 7A, 7B:
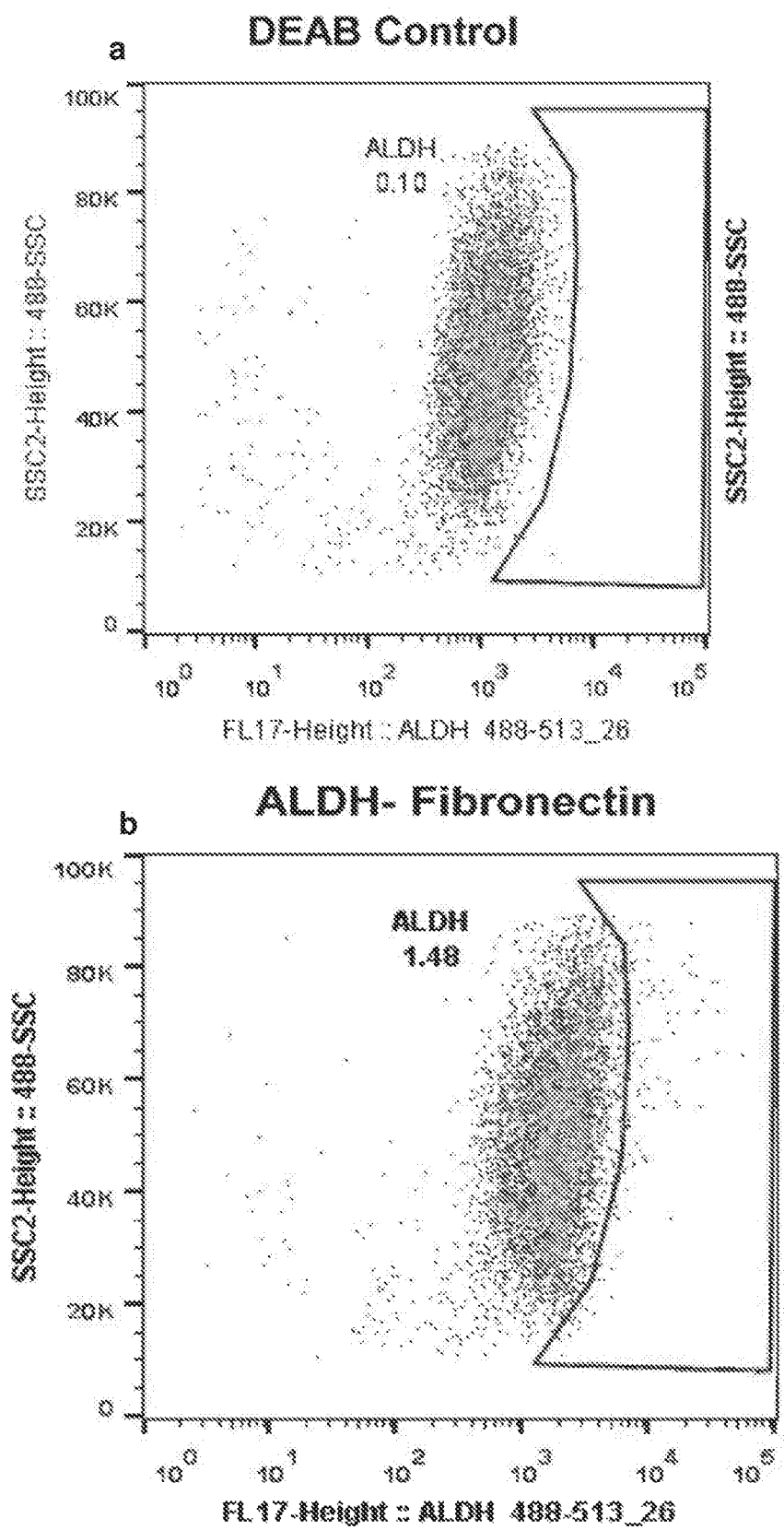
Figure 7C:
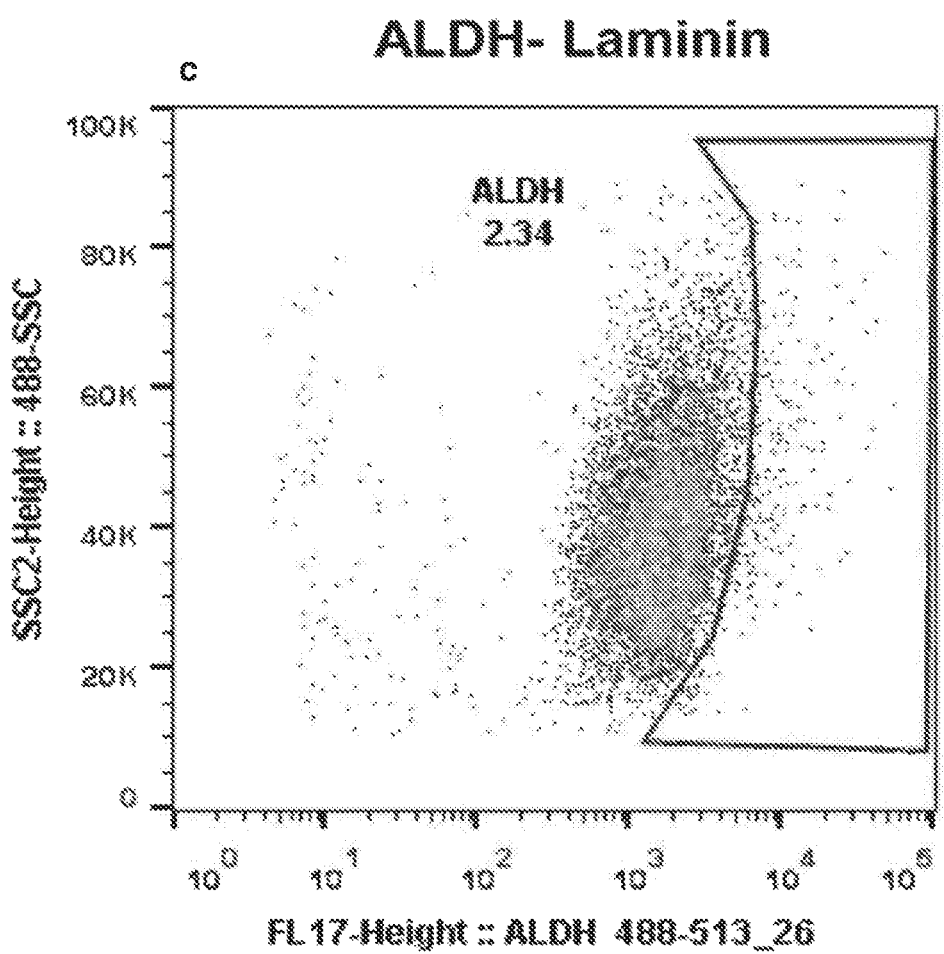

FIGS. 7A-7C show MCF7 breast cancer cells have an increased ALDH positive population when cultured on a cellular support systems having suspended laminin bridge structures in accordance with certain aspects of the present disclosure. A DEAB control is shown in FIG. 7A. FIG. 7B shows ALDH-fibronectin for a cellular support systems having suspended fibronectin bridge structures as a mesh prepared in accordance with certain aspects of the present disclosure. FIG. 7C shows ALDH-laminin for a cellular support systems having suspended laminin bridge structures as a mesh prepared in accordance with other aspects of the present disclosure.

Figure 8:
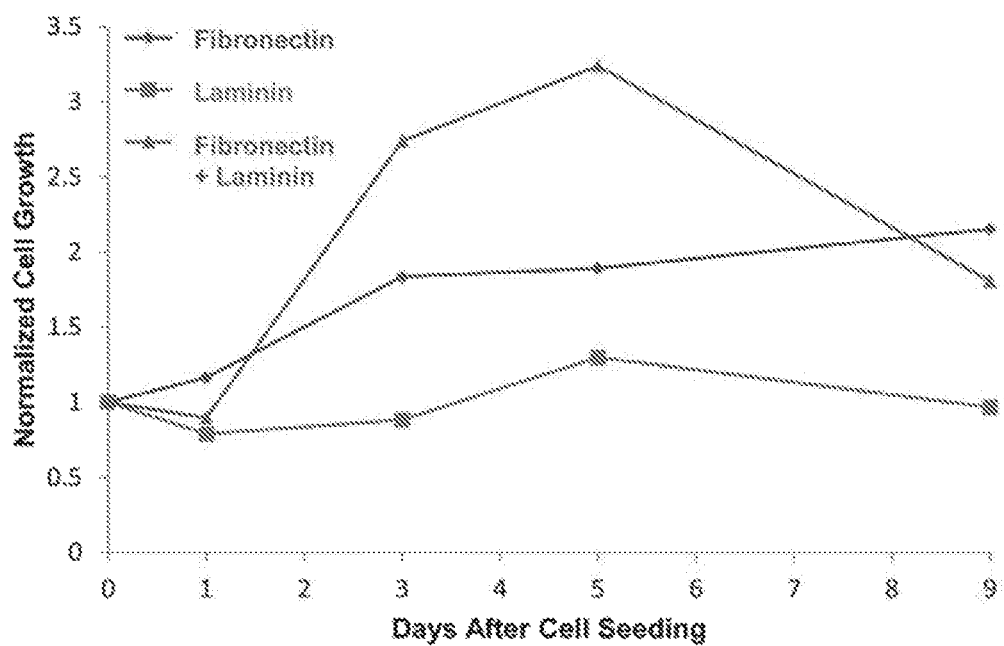

FIG. 8 shows a growth curve for a MDA-MB-231 human breast cancer cell line with normalized cell growth versus days after cell seeding. Three different suspended protein meshes are independently analyzed for impact on growth of MDA-MB-231 breast cancer cells: fibronectin only (green), laminin only (red), and fibronectin plus laminin (purple).

Figures 9A, 9B, 9C, 9D, 9E, 9F, 9G:
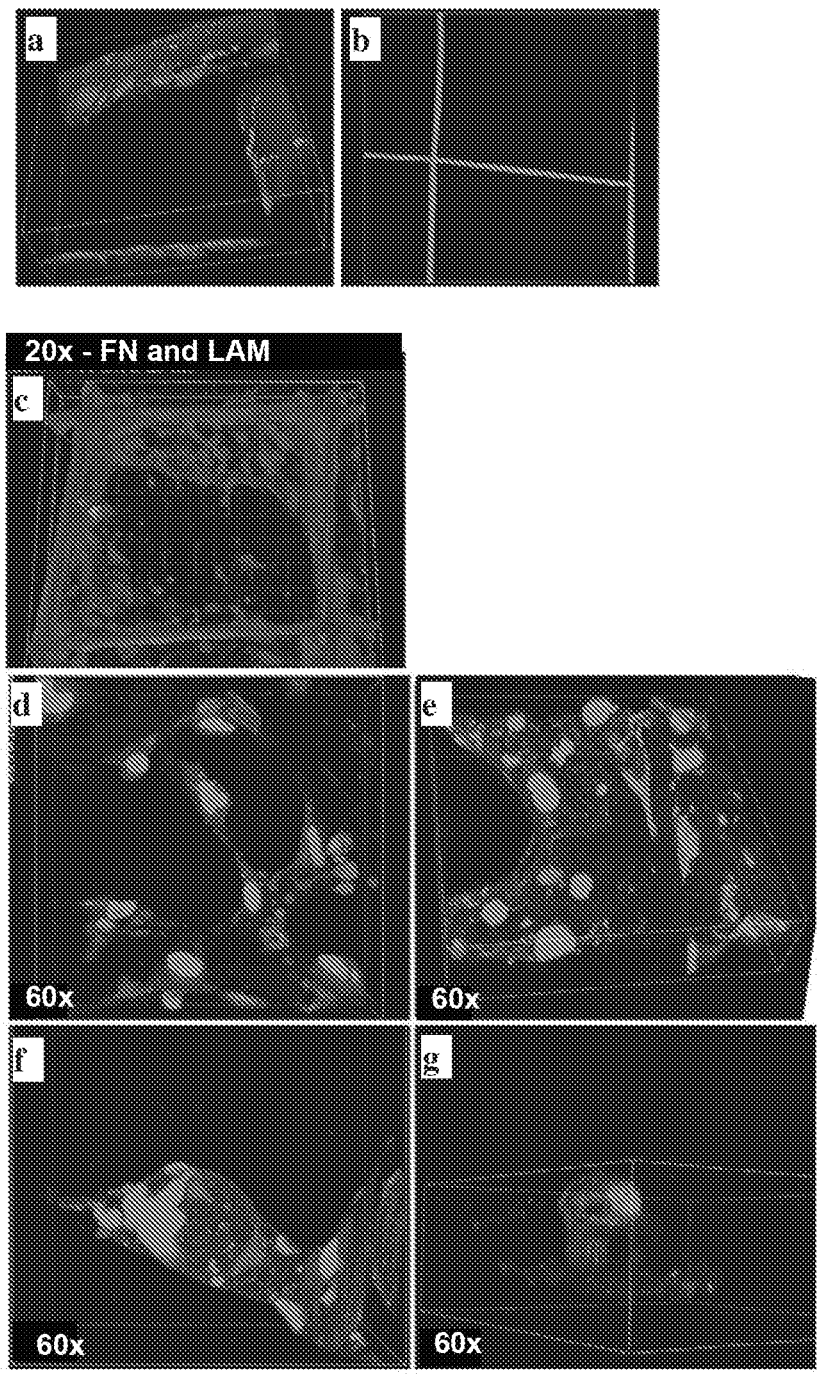

FIGS. 9A-9G show cellular support systems having suspended fibronectin bridge structures as a mesh prepared in accordance with certain aspects of the present disclosures. FIGS. 9A-9B show LSCM images at 20× magnification of cultured HUVECs (human umbilical vein endothelial cells) on either a suspended fibronectin mesh (FIG. 9A) or suspended laminin mesh (FIG. 9B) (polymer in blue, cell nucleus in pink, actin in red). FIG. 9C shows a first LSCM image at 20× of a scaffold having a mesh comprising both laminin and fibronectin with cultured HUVECs, showing that shows cells starting to branch out into the center of the scaffold pore. FIGS. 9D-9G show 60×LSCM images of HUVECS cultured on suspended protein meshes comprising both fibronectin and laminin.

Figure 10:
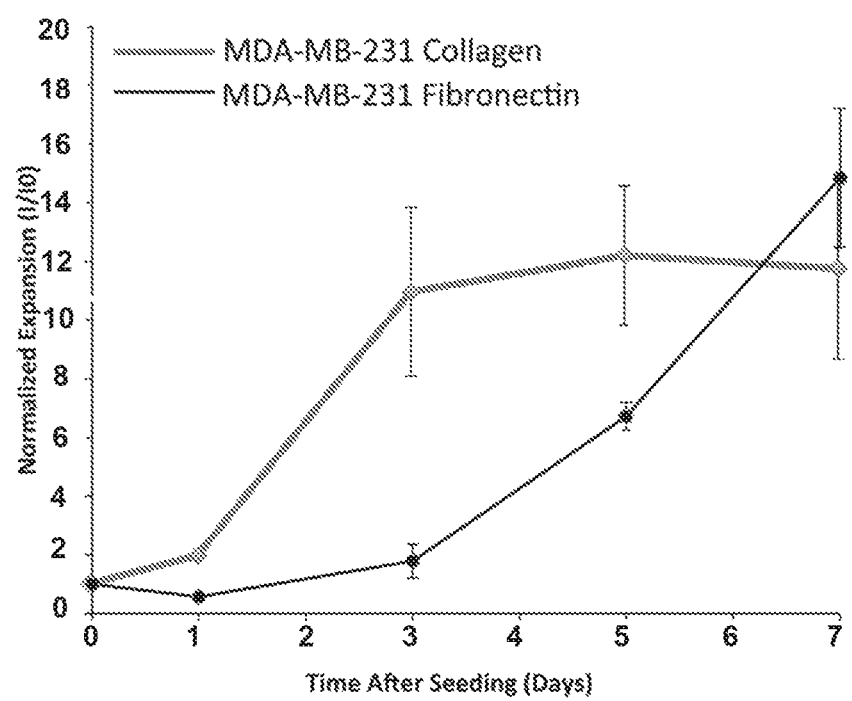

FIG. 10 is a chart of normalized expansion (I/IO) versus time after seeding (days) for MDA-MB-231 breast cancer cells, cultured on cellular support systems having suspended fibronectin bridge structures as a mesh prepared in accordance with other aspects of the present disclosure.

Figures 11A, 11B, 11C, 11D, 11E:
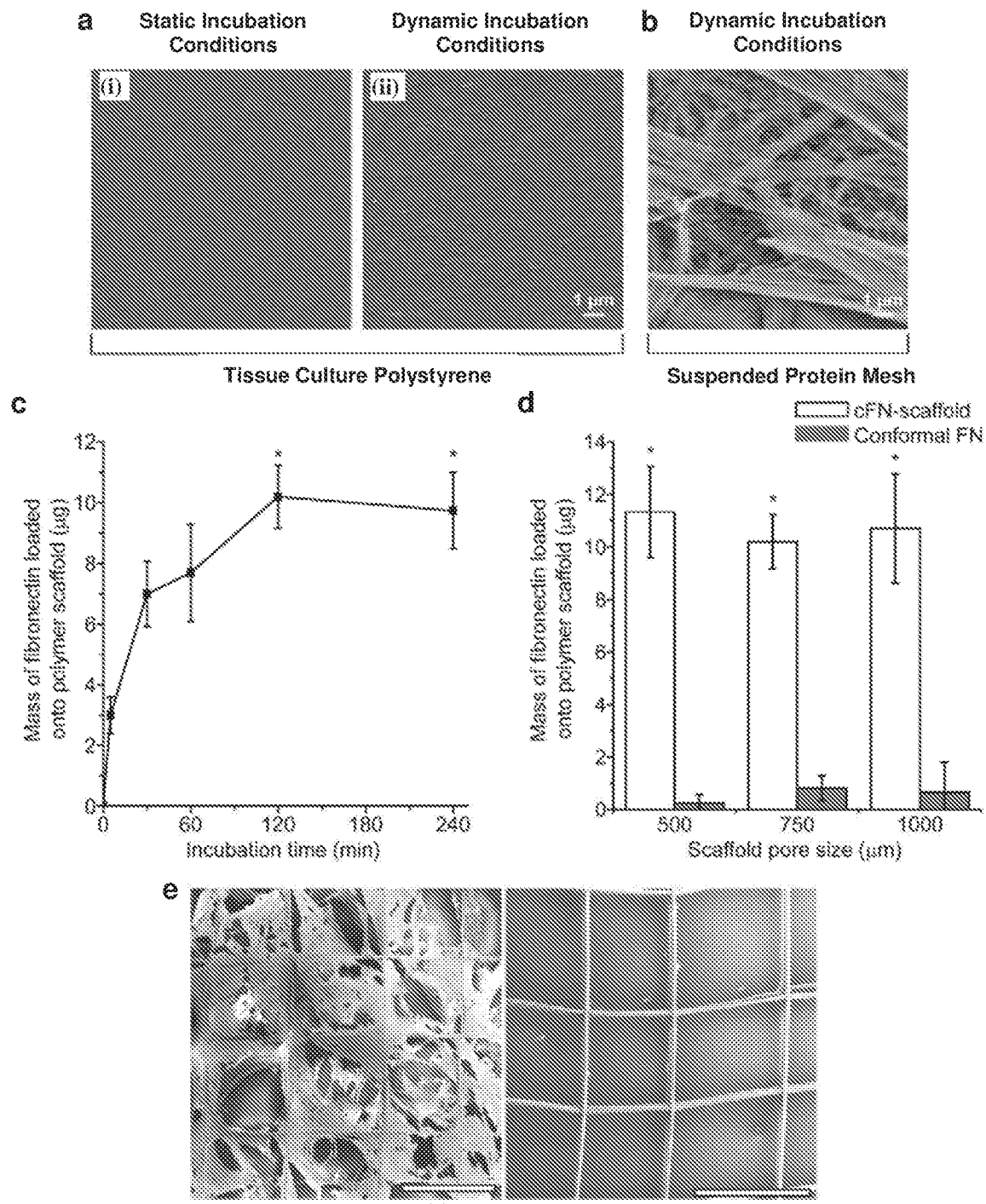

FIGS. 11A-11E. FIG. 11A shows SEM images illustrating comparison of static incubation and dynamic incubation conditions. The left (i) and middle (ii) SEM images show tissue culture on polystyrene coated with the same concentration of protein, at the same temperature, for the same amount of time under both static and dynamic incubation conditions. FIG. 11B shows an SEM image having a suspended protein bridge mesh on a three-dimensional scaffold structure prepared in accordance with the present disclosure that yields a matrix with superior mimicry of the physiological extracellular matrix. Scale bars are 1 μm. FIGS. 11C and 11D show charts of mass of fibronectin loaded onto a polymer support scaffold (m) for a comparative conformal protein coating on a scaffold (Conformal fibronectin (FN)) and a suspended protein bridge mesh on a three-dimensional scaffold structure prepared in accordance with the present disclosure (cellular fibronectin (cFN)-scaffold). FIG. 11C shows mass of conformal fibronectin (cFN) synthetically deposited onto microfiber scaffold over time of incubation at the fluid interface under shear flow. FIG. 11D show mass of fibronectin loaded onto a microfiber scaffold as a function of scaffold pore size after either shear-driven synthetic deposition (cFN-scaffolds, white bars) or conformal coating via static adsorption (grey bars). FIG. 11E shows SEM contrasting loading of fibronectin (left) synthetically deposited and (right) conformally coated onto polymer microfiber scaffolds. Scale bars are 500 μm.

Figures 12A, 12B:
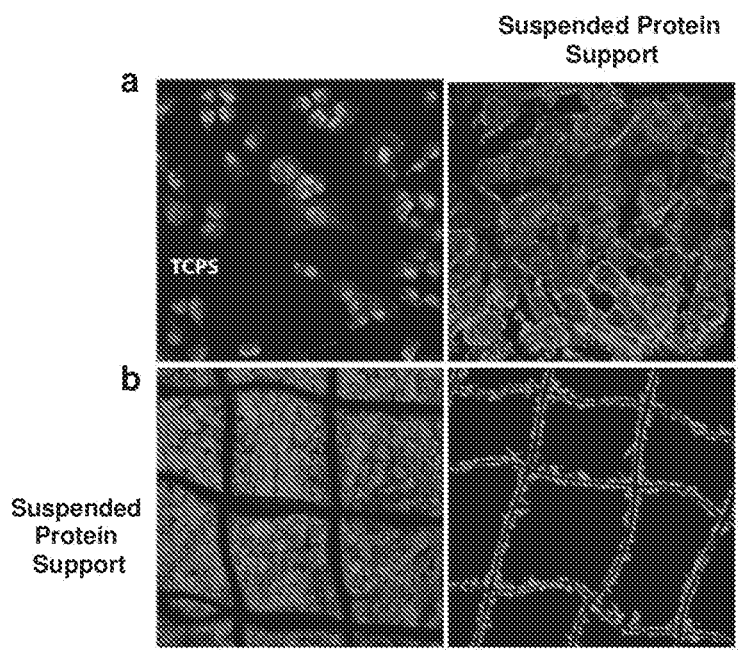

FIGS. 12A-12B show a comparison of a human breast cancer cell line MDA-MB-231s cultured on tissue culture polystyrene (TCPS) versus a suspended fibronectin protein bridge mesh on a three-dimensional scaffold structure prepared in accordance with the present disclosure, which remodels protein and moves off a suspended fibronectin bridge mesh. FIG. 12A (left) shows MDA-MB-231 (231s) human breast cancer cell line cultured on tissue culture polystyrene (TCPS). Cell nucleus is in purple, actin is in green. Laser scanning confocal microscope (LSCM) image at 60× magnification. FIG. 12A (right) shows MDA-MB-231 human breast cancer cells cultured and imaged on suspended fibronectin mesh scaffolds at 60× magnification on LSCM. Cell nucleus in cyan, actin in green. FIG. 12B (left) shows 231s after 5 days of culture forming a confluent volume of tissue on the suspended fibronectin mesh cell culture scaffold. FIG. 12B (right) shows that after 9 days of culture on suspended fibronectin mesh 231s are no longer tethered to the protein but rather move off into solution.

Figure 13:
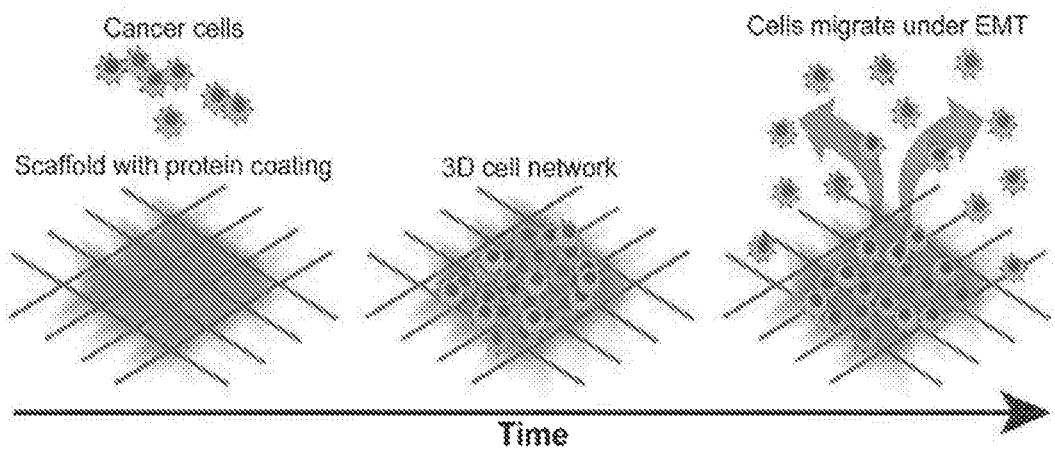

FIG. 13 shows a schematic of Epithelial to Mesenchymal Transition (EMT) cell behavior on tissue scaffolds having a protein coating. Cancer cells are first seeded onto scaffolds where they form a 3D interconnected cellular network. Upon reaching a critical confluency, cells become more mesenchymal and migrate off the scaffold, remaining viable in solution.

Figure 14:
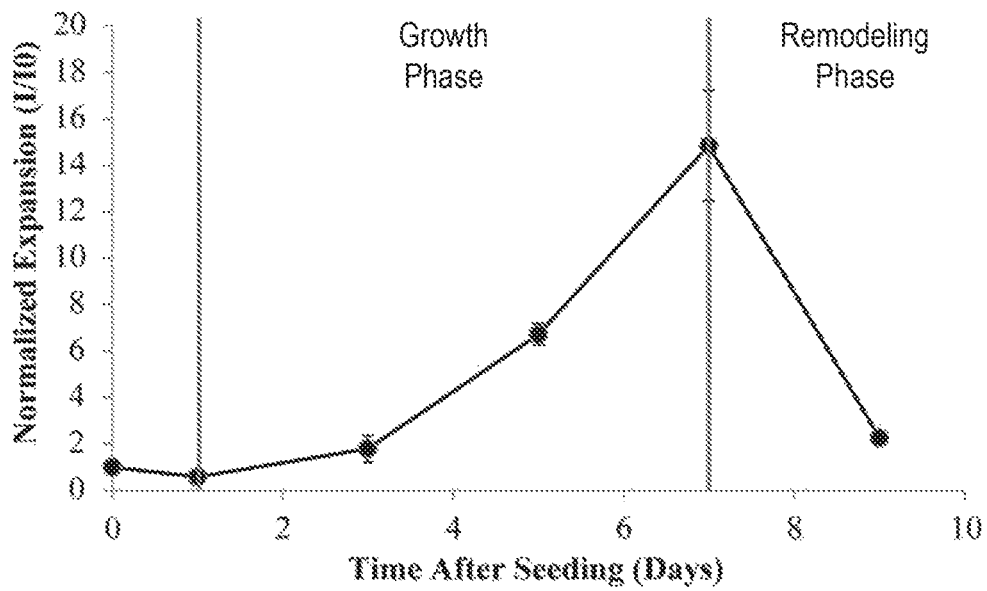

FIG. 14 shows that a suspended protein bridge mesh on a three-dimensional scaffold structure prepared in accordance with certain aspects of the present disclosure can be applied as an in vitro model for cancer metastasis. FIG. 14 shows time after seeding (days) versus normalized expansion (I/IO). In parallel, bioluminescence is used to produce the growth curve on the left. Initially, cells are rapidly proliferating in a "growth phase." At day 7, the cells reach a peak population, then enter a "remodeling phase" where they leave the suspended protein mesh, and remain viable in solution. MDA-MB-231 human breast cancer cells form confluent volumes at first, but eventually migrate off the suspended protein mesh, as shown in FIGS. 12A-12B.

Figure 15:
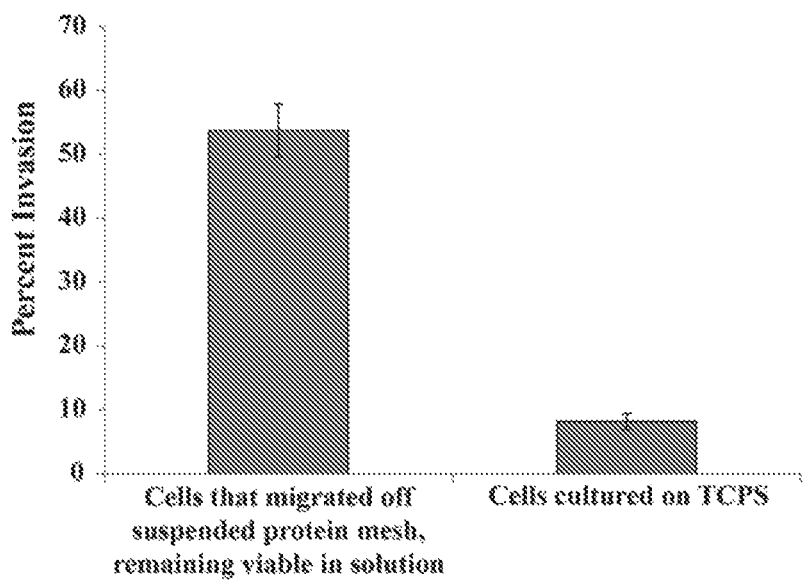

FIG. 15 shows percent invasion for cells that are cultured in parallel on either suspended fibronectin bridge meshes on a three-dimensional scaffold structure prepared in accordance with the present disclosure or a tissue culture polystyrene (TCPS) support.

Figure 16:
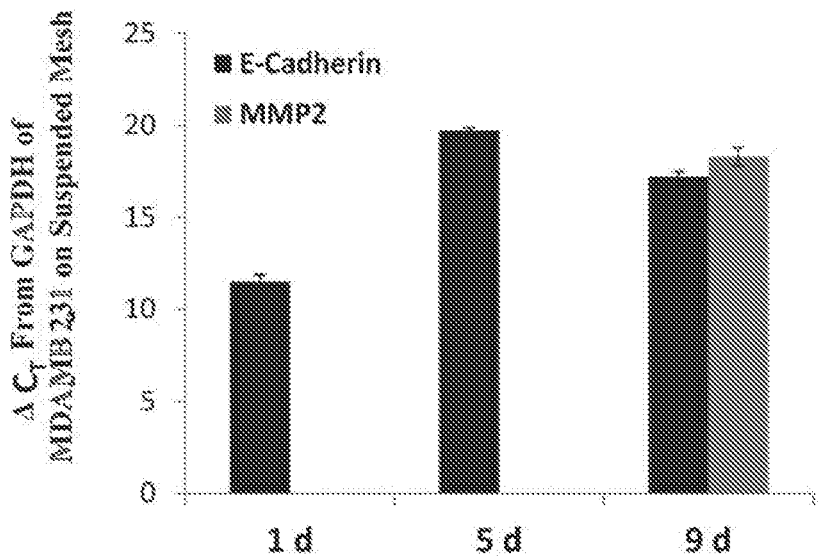

FIG. 16 shows $\Delta C_T$ from GAPDH for MDA-MB-231 human breast cancer cells cultured on suspended fibronectin protein meshes prepared in accordance with certain aspects of the present disclosure for nine days.

Figure 17A:
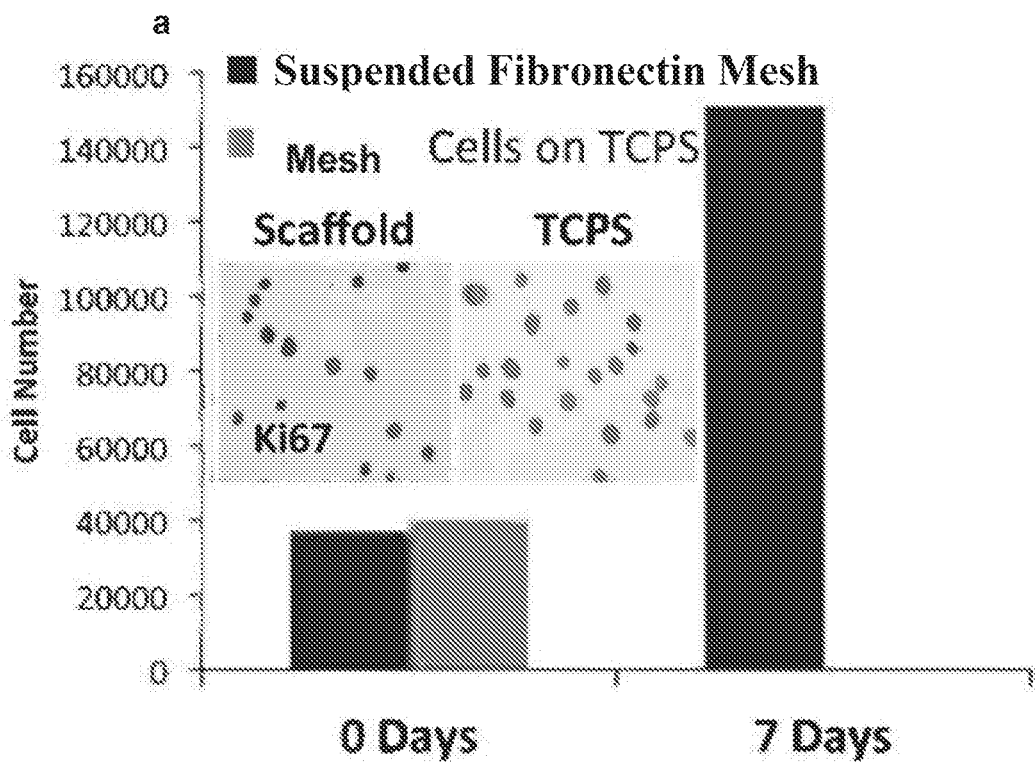
Figures 17B, 17C, 17D:
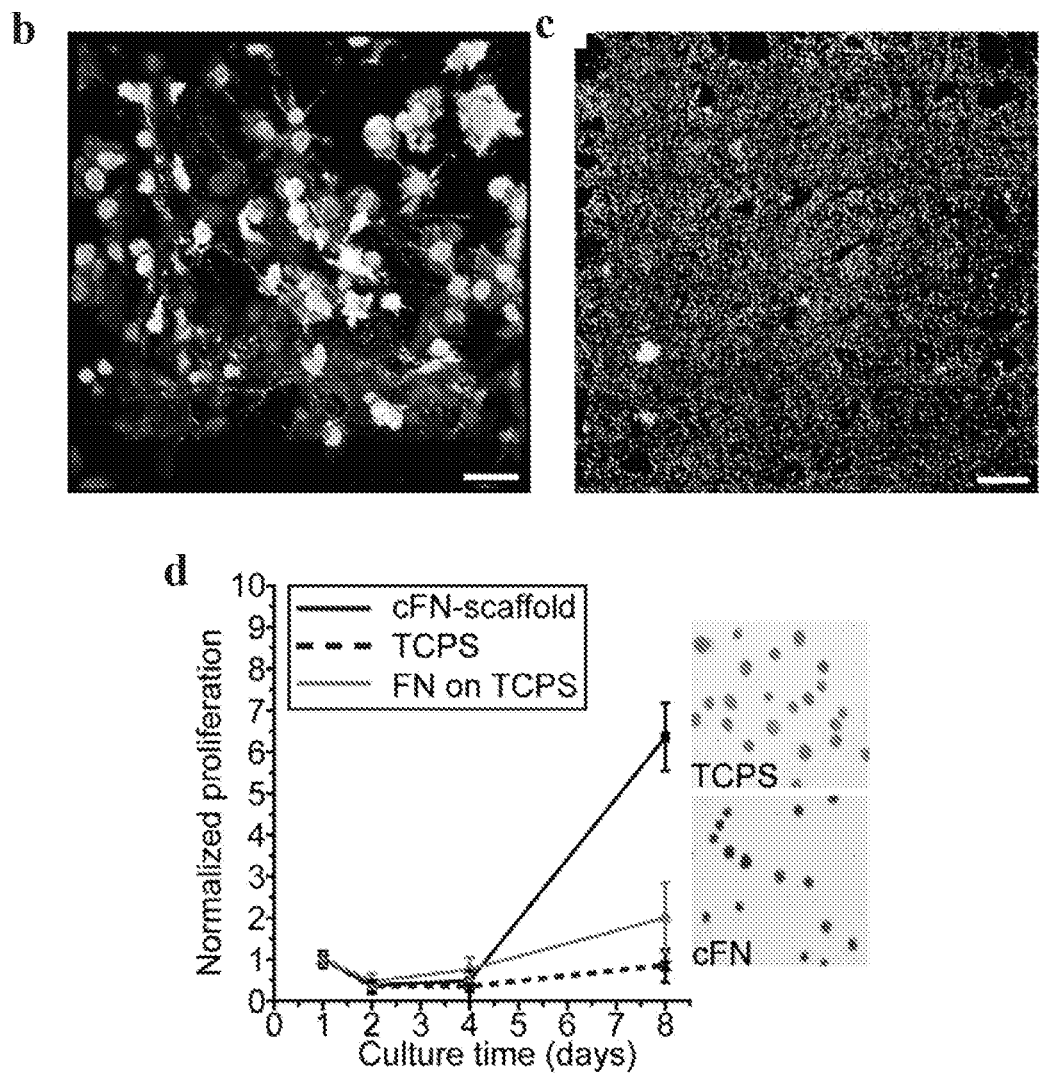
Figure 17E:
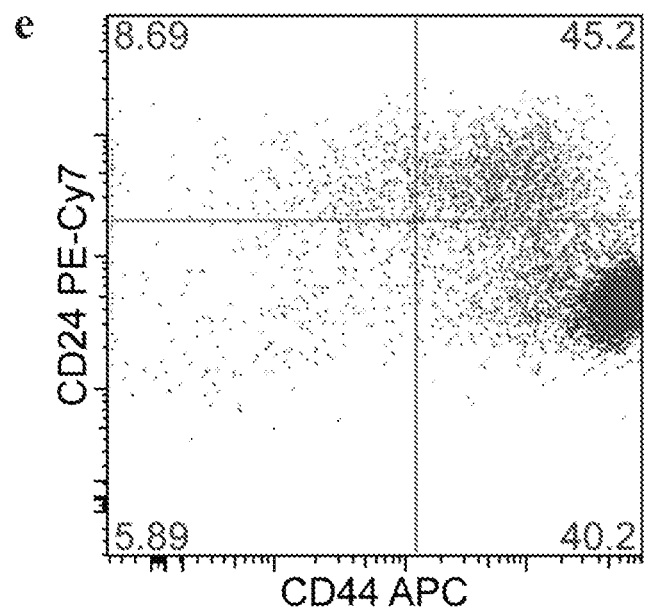

FIGS. 17A-17I show cFN-scaffolds prepared in accordance with certain aspects of the present disclosure enable expansion of patient breast cancer cells and enrich the tumor initiating cell population in an epithelial to mesenchymal transition (FIGS. 17B-17C) Ascites sample from Patient E cultured on cFN-scaffold. Channels: cyan, cell nucleus; red, actin; yellow, cytokeratin 5. FIG. 17A shows cell number counts at 0 days and 7 days for breast cancer patient cells on conventional tissue culture polystyrene (TCPS) versus a suspended protein bridge mesh on a three-dimensional scaffold structure prepared in accordance with the present disclosure (labelled as scaffold). FIG. 17B shows Patient E cells fill cFN-scaffold at large scale across many 500 µm pores. Scale bar is 500 µm. FIG. 17C shows a heterogeneous mix of cells form 3D structures within the pores and along the microfibers of the scaffold. Scale bar is 25 µm. FIG. 17D shows proliferation for ascites sample from Patient D normalized to the initial number of cells seeded. Proliferation is measured via mitochondrial activity after one day, three days, and seven days of culture on cFN scaffolds (black solid line and square marker), fibronectin conformally coated onto TCPS (grey line and triangular marker), or TCPS (black dotted line and criss-cross marker). Inset shows representative images of Ki67 staining of Patient E cells cultured on either TCPS or cFN-scaffolds. Darker color indicates that the cells are in a proliferative state on cFN-scaffolds but not on TCPS. FIG. 17E shows flow cytometry measurement of CD24 and CD44 in the ascites sample from Patient A where the original sample is shown in red and the same sample after five days of culture on cFN-scaffolds is shown in blue. FIGS. 17F-17I show flow cytometry measurements of the percentage of lineage negative cells that are (FIG. 17F) CD44$^+$/CD24$^-$ (FIG. 17G) EpCAM$^+$ (epithelial cell adhesion molecule) (FIG. 17H) ALDH$^+$ (aldehyde dehydrogenase) and (FIG. 17I) CD44$^+$/CD24$^-$/ALDH$^+$ within ascites samples from Patients A and B, and a pleural effusion sample from Patient C. Grey bars represent the original patient sample and white bars indicate result after cells are cultured on cFN-scaffolds in vitro for five days.

Figure 18A:
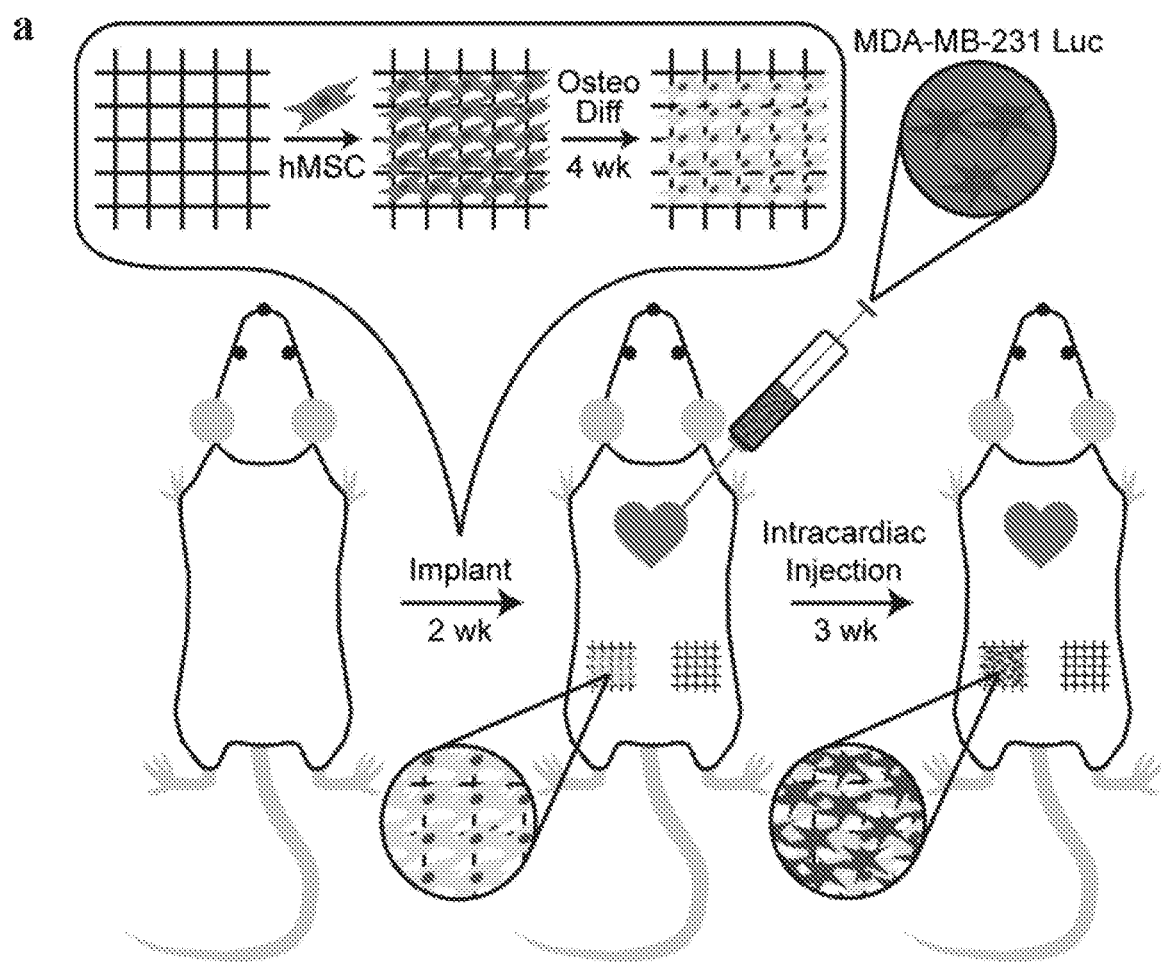
Figures 18B, 18C, 18D:
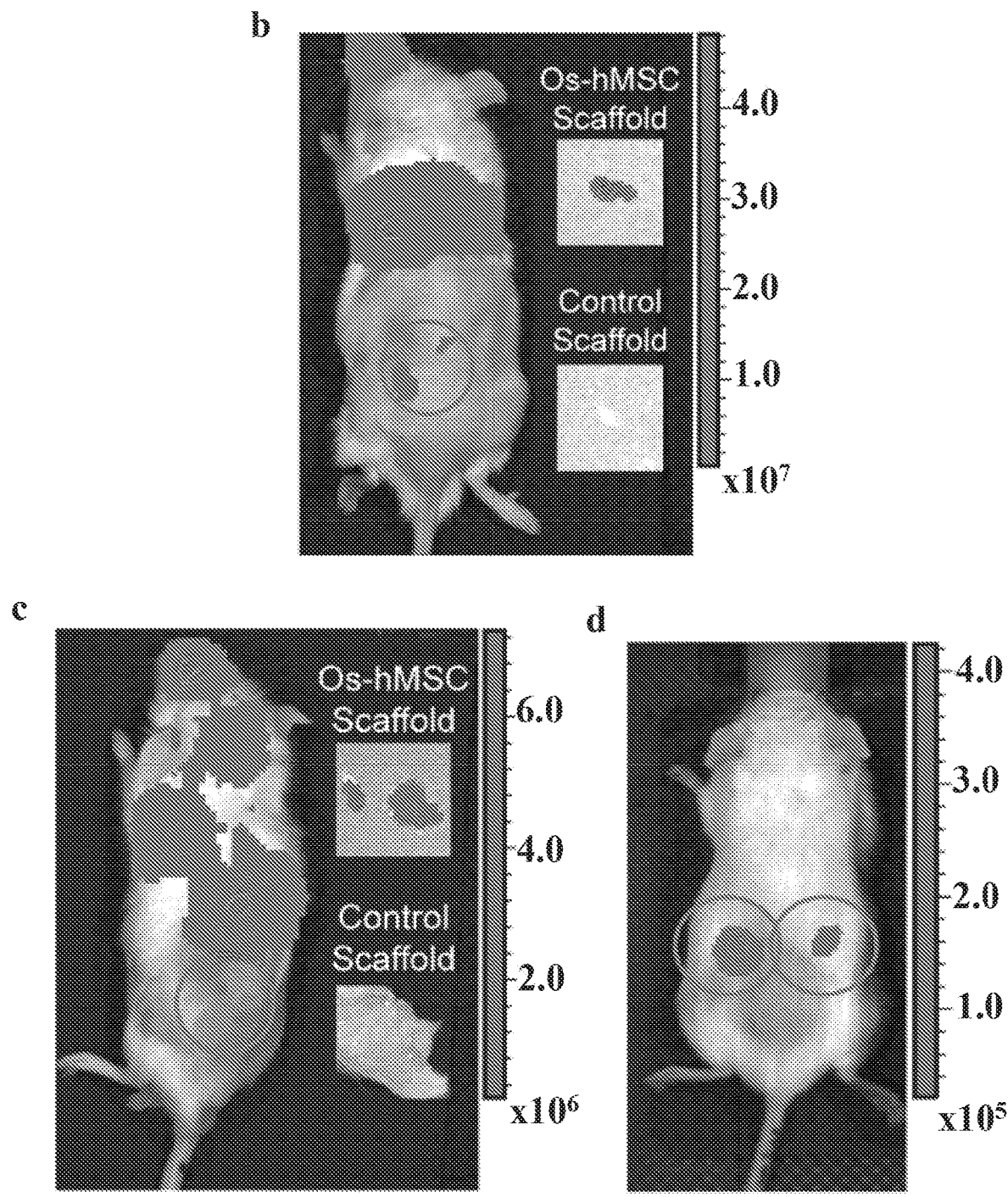

FIGS. 18A-18D. FIG. 18A shows a schematic for seeding human mesenchymal stem cells on a PLGA fiber scaffolds having suspended fibronectin that led to confluent volumes of cells over the course of 3-5 days, which are implanted into a NOD SCID mouse along with comparative scaffolds with fibronectin protein coating only. FIGS. 18B-18C shows the mice are injected with luciferin three weeks post-injection after scanning in a bioluminescent scanner. FIG. 18D shows that implantation of osteogenically differentiated cells on both sides of the mouse led to bioluminescent signal in both implants.

Figures 19A, 19B, 19C:
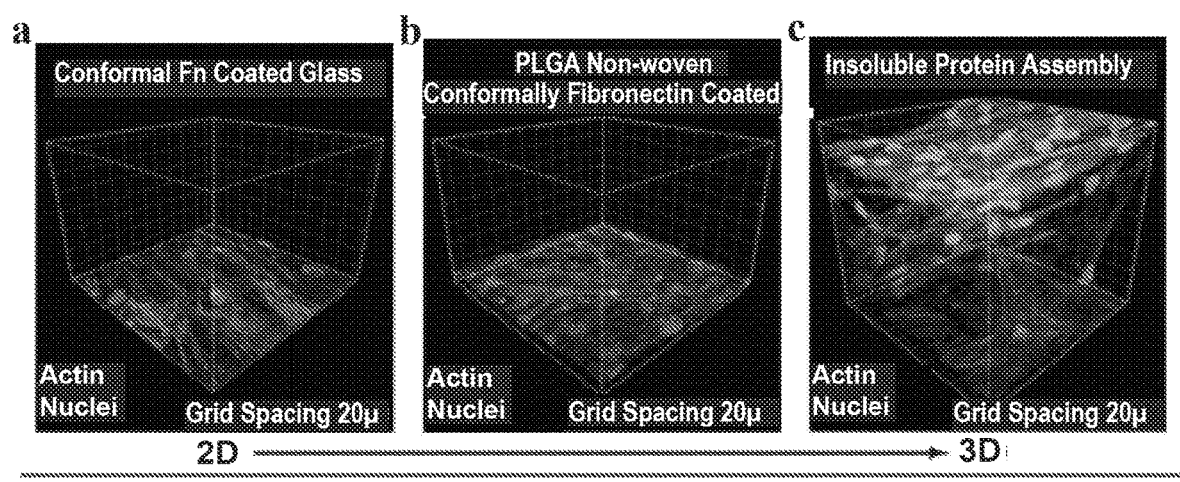

FIGS. 19A-19C show three-dimensional growth of human mesenchymal stem cells on a conformal fibronectin-coated glass (FIG. 19A), a conformally fibronectin coated PLGA non-woven scaffold (FIG. 19B), and a suspended insoluble protein bridge mesh on a three-dimensional scaffold structure prepared in accordance with the present disclosure (FIG. 19C).

Figure 20:
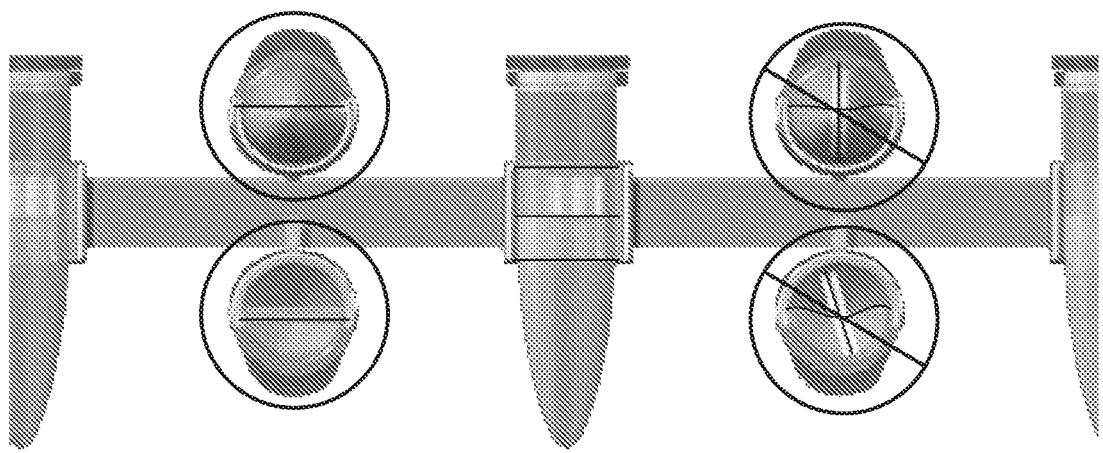

FIG. 20 shows a schematic of the proper positioning of an air-liquid matrix near a three-dimensional scaffold structure during rotation in accordance with certain aspects of the present disclosure.

Figures 21A, 21B, 21C, 21D, 21E, 21F, 21G:
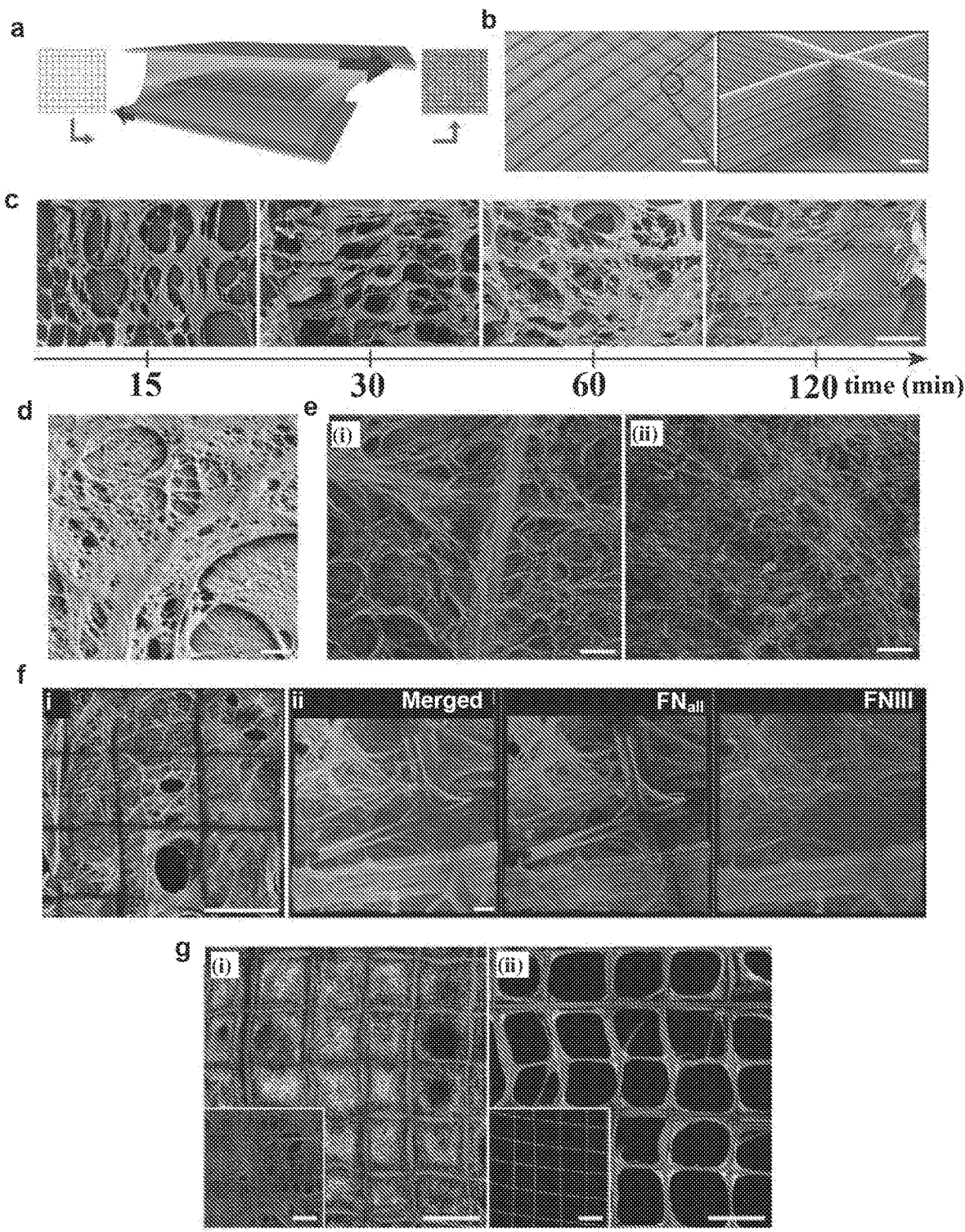

FIGS. 21A-21G show shear-driven synthetic deposition of cellular fibronectin (cFN). FIG. 21A shows a tissue scaffold secured at the interface of two fluid phases, where one phase carries the solubilized protein of interest. After incubation under the force of fluid shear, the scaffold emerges from this process carrying insoluble suspended networks of the protein, in the case of fibronectin, a cFN-scaffold prepared in accordance with certain aspects of the present disclosure. FIG. 21B shows polymer microfiber scaffolds fabricated via 3D jet writing providing a skeletal support for the suspension of networks of cFN across and within 500 µm wide square pores. Scale bars 500 µm (left, zoomed out view) and 25 µm (inset). FIG. 21C shows a time course depicting cFN loading onto the scaffold after 15, 30, 60, and 120 minutes of contact time at the fluid interface under shear. Scale bar is 500 µm. FIG. 21D shows a high resolution scanning electron micrograph (SEM) of cFN within a pore of the scaffold. Scale bar is 1 µm. FIG. 21E shows laser scanning confocal micrograph (LSCM) of cFN (green) suspended within the microfiber scaffold (shown on the left at (i)) for comparison to fibronectin deposited by human mammary fibroblasts cultured on glass and subsequently decellularized shown on the right at (ii). Scale bar is 25 µm. FIG. 21F shows at (i) a cross-sectional view of suspended fibronectin spanning across the large pores of the microfiber scaffold with the fibronectin-3 (FNIII) domain exposed. Scale bar is 500 µm. FIG. 21F at (ii) shows higher magnification of a cFN scaffold where fibronectin (green) and the specific FNIII domain (purple) are stained. Strong overlap of green and purple appear white in overlay image (labelled merged on the left). Scale bar is 25 µm. FIG. 21G shows NIH-3T3 mouse fibroblasts cultured three days on either a cFN-scaffold prepared in accordance with certain aspects of the present disclosure (i) or fibronectin conformally coated by static adsorption onto a microfiber scaffold (ii). Insets show representative images of the morphology and distribution of fibronectin (green) on scaffolds (blue) with either cFN (left inset) or conformally coated fibronectin (right inset). Channels: blue, polymer microfibers; green, fibronectin; cyan, cell nucleus; red, actin. Scale bars 500 µm.

Figures 22A, 22B, 22C:
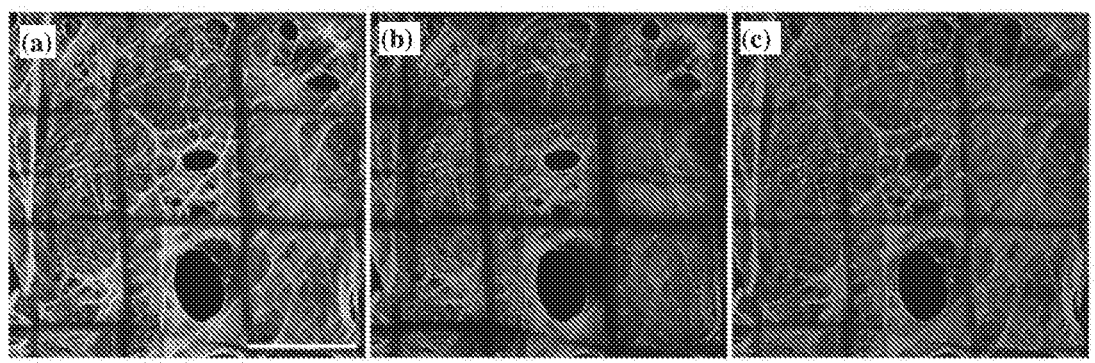

FIGS. 22A-22C shows a FNIII domain exposed across cFN-scaffold at large scale split channel view of FIG. 21F (i) detailing the extent of exposure of the FNIII domain across the open pores and at large scale throughout the cFN-scaffold. Channels: green, fibronectin; purple, FNIII domain. FIG. 22A shows both green and purple staining (fibronectin and FNIII). Scale bar is 500 µm. FIG. 22B shows green staining for fibronectin. FIG. 22C shows purple staining for the FNIII domain.

FIGS. 23A-23D show shear-driven synthetic deposition prepared in accordance with the present disclosure uniquely extends fibronectin into a cellular form.

Figures 23A, 23B, 23C, 23D:
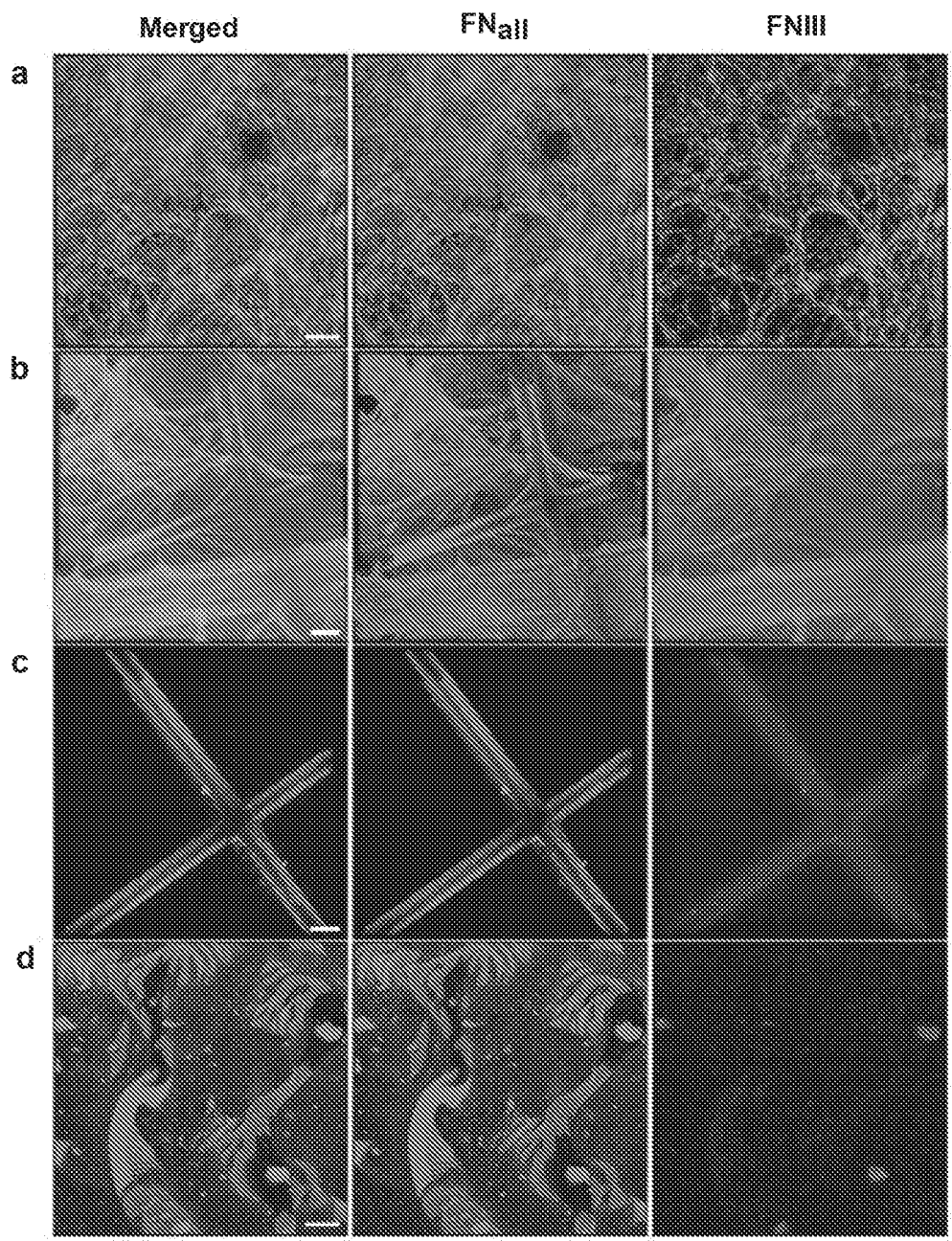

FIG. 23A shows fibronectin (green—middle column labelled $FN_{all}$) as secreted by human mammary fibroblasts cultured on glass and subsequently decellularized showing exposure of FNIII domains (purple—right column labelled FNIII). The overlay of the two channels shown in left column is labelled "merged." FIGS. 23B-23D show overlay of channels (left column—labelled "merged"), fibronectin (green, center column, labelled $FN_{all}$), and FNIII domain (purple, right column labeled $FN_{III}$) for plasma fibronectin on cFN-scaffold prepared in accordance with certain aspects of the present disclosure (FIG. 23B), conformally coated onto microfiber scaffold (FIG. 23C), and conformally coated onto glass via static adsorption (FIG. 23D). Scale bars are 25 µm. All images taken at the same laser power and imaging settings via LSCM. Strong overlap of green and purple appear white in overlay image (left images in FIGS. 23A and 23B).

Figures 24A, 24B, 24C, 24D, 24E, 24F:
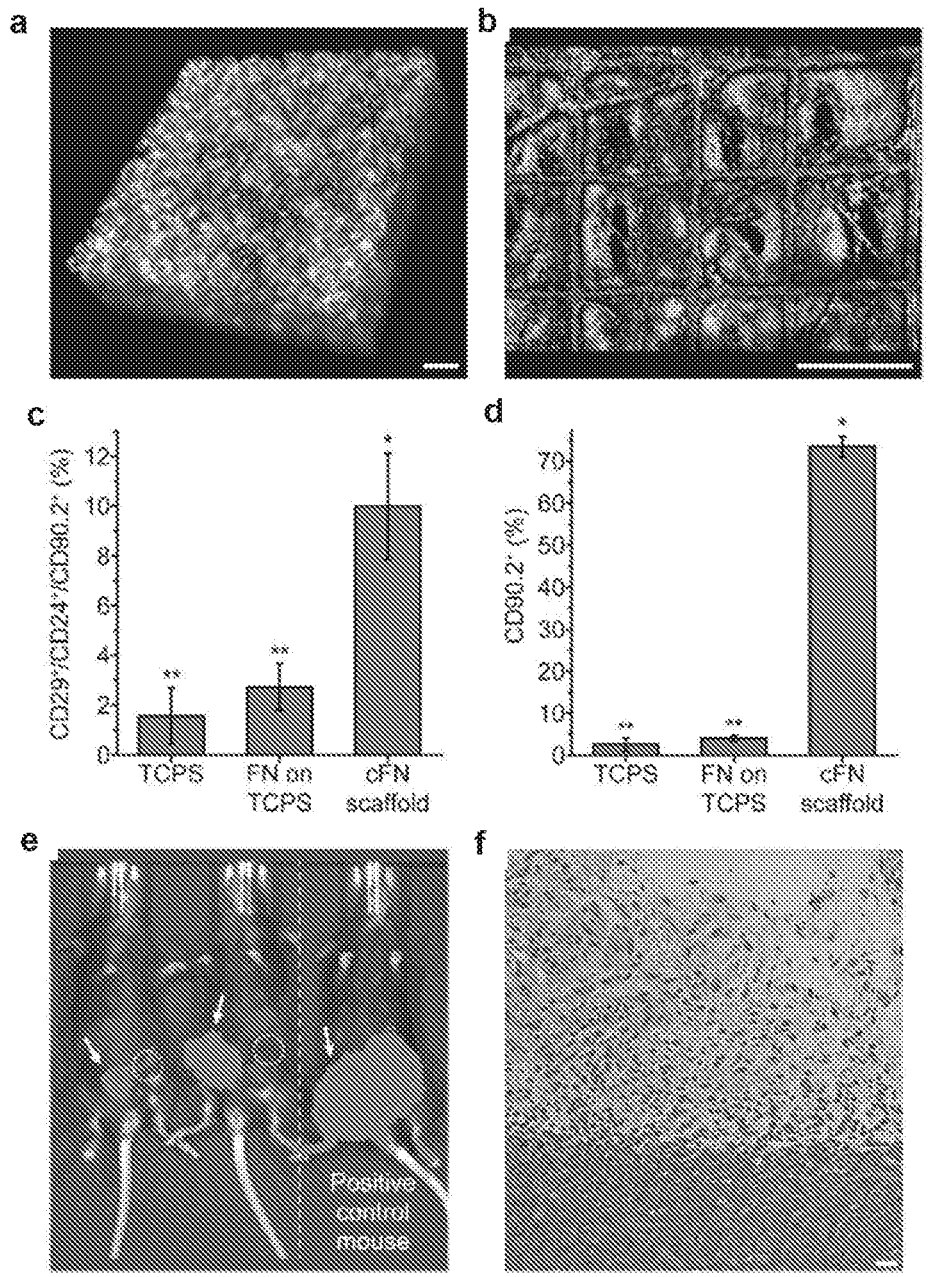

FIGS. 24A-24F show cellularized fibronectin (cFN)-scaffolds enhance tumor engraftment efficiency in a mouse breast cancer model. FIG. 24A shows a representative 3D LSCM of AT-3 mouse breast cancer tissue formed in vitro on cFN-scaffolds prepared in accordance with certain aspects of the present disclosure. Section thickness is approximately 70 µm. Scale bar is 25 µm. FIG. 24B shows a large scale view of AT-3 tissue cultured on cFN-scaffolds as in FIG. 24A. Cells proliferate and fill the 3D space within and across the suspended protein network. Scale bar 500 is µm. FIGS. 24A-24B channels: cyan, cell nucleus; red, actin. FIG. 24C shows quantification of the $CD29^+/CD24^+/CD90.2^+$ AT-3 cells identifying the tumor initiating population after three days of culture on TCPS, TCPS conformally coated with fibronectin (FN on TCPS), and cFN-scaffolds. A single star indicates that the cFN-scaffold is statistically different from TCPS and FN on TCPS; double star indicates that TCPS and FN on TCPS are statistically similar. FIG. 24D shows quantification of the $CD90.2^+$ population of AT-3 cells after three days of culture on TCPS, fibronectin conformally coated on TCPS (FN on TCPS), or cFN-scaffolds. A single star indicates that the cFN-scaffold result is statistically different from TCPS and FN on TCPS; double star indicates that TCPS and FN on TCPS results are statistically similar. FIG. 24E shows a bioluminescence image of immune-competent mice showing tumor formation 21 days after AT-3 cells are orthotopically implanted (image exposure time 10 seconds). The two mice on the left have had cFN-scaffolds carrying about 30,000 AT-3 cells implanted into the mammary fat pads indicated by arrows. The right mammary fat pad received an injection of approximately the same number of cells in the area indicated by circles. The third mouse on the right is a positive control having received a cFN-scaffold in the left mammary fat pad (arrow), and an injection in the mammary fat pad on the right, each delivering 200,000 AT-3 cells. Previous studies have concluded that a minimum of 200,000 AT-3 cells are required for tumor formation by injection. FIG. 24F shows Mason's Trichrome staining of a tumor graft that formed at the implant site of the cFN-scaffold carrying 30,000 AT-3 cells; AT-3 cells invaded surrounding tissues. Scale bar is 25 µm.

Figures 25A, 25B, 25C:
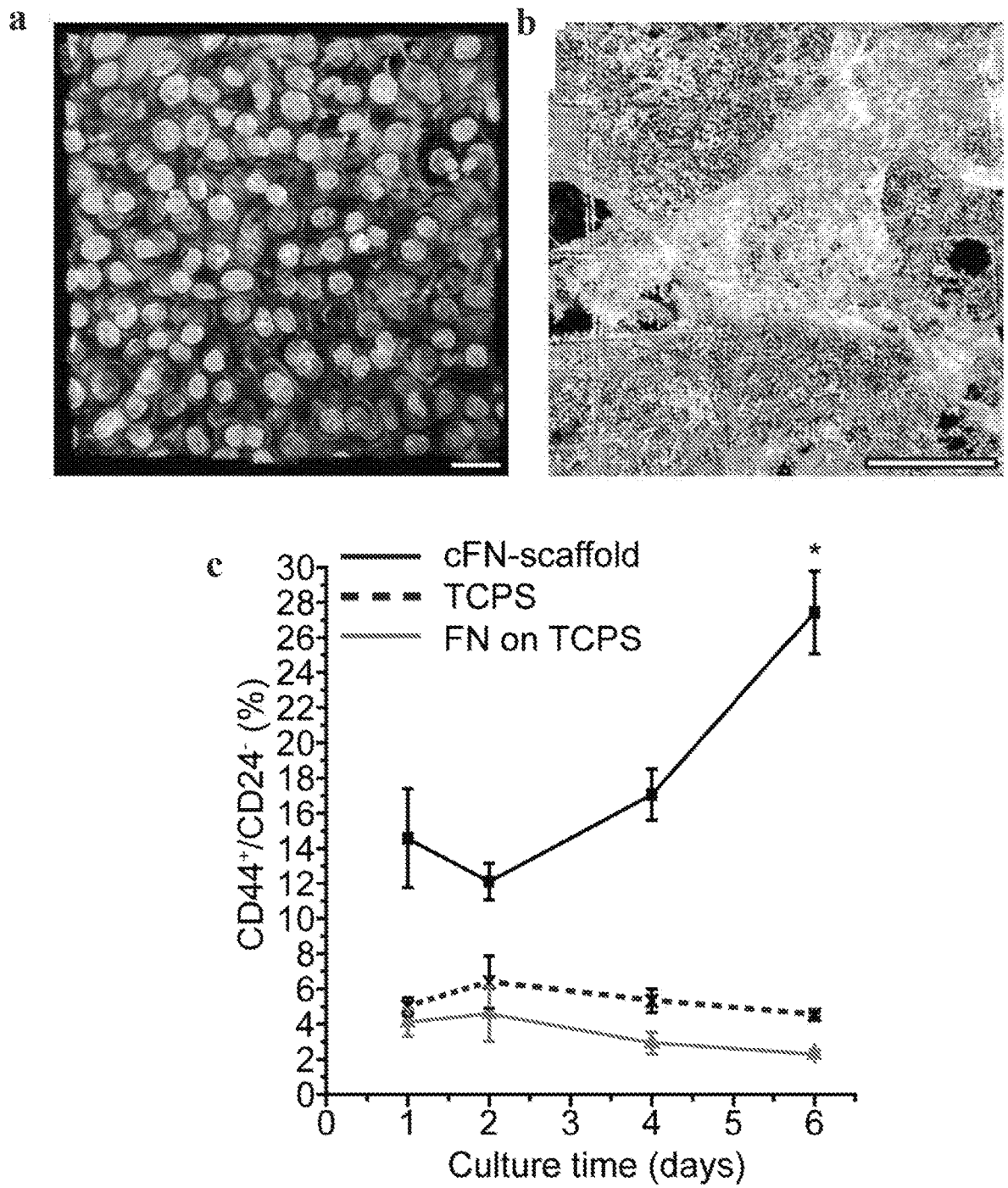
Figure 25D:
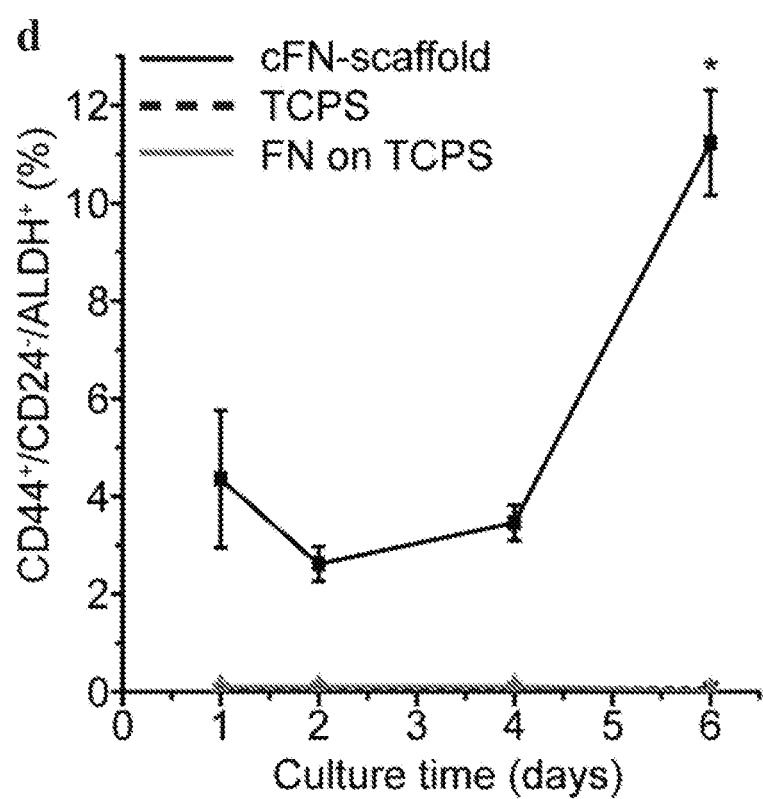

FIGS. 25A-25D show cellularized fibronectin (cFN)-scaffolds increase the tumor initiating population in MDA-MB-468 human breast cancer cells. FIG. 25A shows MDA-MB-468 breast cancer cells cultured four days on cFN-scaffolds prepared in accordance with certain aspects of the present disclosure. Scale bar is 25 µm. FIG. 24B shows a large scale view of MDA-MB-468 cells on cFN-scaffolds. Scale bar is 500 µm. FIGS. 25A-25B show channels: green, fibronectin; orange, laminin; cyan, cell nucleus; red, actin. FIGS. 25C-25D show a population of MDA-MB-468s on cFN-scaffolds (black solid line and square marker), TCPS (black dotted line and criss-cross marker), or fibronectin conformally coated onto TCPS (grey line and triangular marker) that are (FIG. 25C) $CD44^+/CD24^-$ and (FIG. 25D) $CD44^+/CD24^-/ALDH^+$ measured over time via flow cytometry. The starred time point is statistically different from the other three time points within the cFN scaffold dataset.

Figures 26A, 26B:
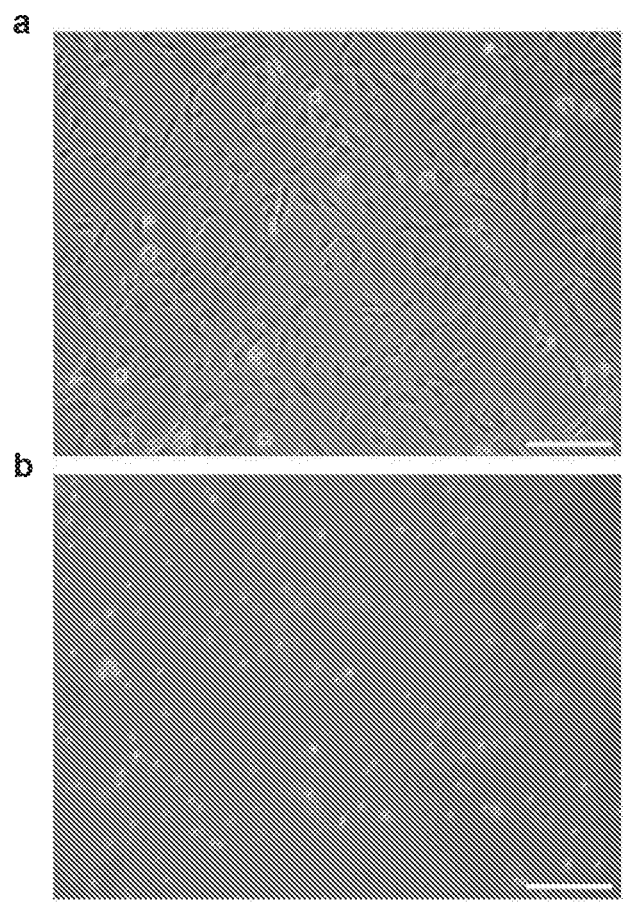

FIGS. 26A-26B show patient pleural effusion cells grow on tissue culture polystyrene only when first grown and expanded on a cellular support system comprising cFN-scaffolds prepared in accordance with certain aspects of the present disclosure. FIG. 26A shows pleural effusion samples from Patient A cultured first on a cFN-scaffold for one day then trypsinized and re-plated onto tissue culture polystyrene (TCPS) dish. FIG. 26B shows a Brightfield microscope image of cells from the same patient sample as in FIG. 26A plated directly from the patient onto TCPS. Image taken after one day of culture showing cells do not survive. Scale bars are 25 µm.

Figure 27:
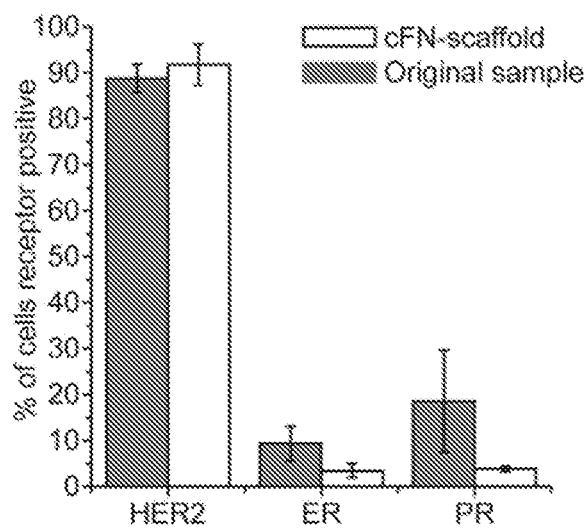

FIG. 27 shows a pleural effusion sample from Patient F made into a cytospin, stained, and quantified for positive signals of human epidermal growth factor receptor 2 (HER2), estrogen receptor (ER), and progesterone receptor (PR). This analysis is performed on cells from the original patient sample (grey bars) and after five days of culture on cFN-scaffolds (white bars). Hospital data reported that this patient's receptor status is $HER2^+$ $ER^-PR^-$. Error bars represent standard deviation of % of receptor positive cells measured from three to four microscope fields of view.

Corresponding reference numerals indicate corresponding parts throughout the several views of the drawings.

DETAILED DESCRIPTION

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%.

In addition, disclosure of ranges includes disclosure of all values and further divided ranges within the entire range, including endpoints and sub-ranges given for the ranges.

Example embodiments will now be described more fully with reference to the accompanying drawings.

In various aspects, the present disclosure provides a cellular support system. The cellular support system includes a three-dimensional scaffold structure comprising at least one void. The cellular support system also includes a suspended protein bridge spanning across the at least one void in the three-dimensional scaffold structure. The suspended protein bridge is capable of supporting cells and promotes three-dimensional cellular growth. The combination of these two components as herein described results in a solid, three dimensional protein matrix that mimics the extracellular matrix as deposited by cells in vivo. Using a hierarchically structured protein material with a periodic rather than a random structure affords various advantages of the present teachings. The scaffold and its voids or pores act as a nucleation site where the protein comes out of solution, and tethers onto the scaffold to create a suspended protein support. In this manner, the suspended protein bridge supports adherent cells, so that a solid, biocompatible environment for the culture of cells in three-dimensions is provided.

Three Dimensional Scaffold Structure

The cellular support system includes a three-dimensional scaffold structure comprising at least one void. A void as used herein is an open volume formed within a solid or semi-solid material. Voids may include pores, surface features, holes, openings, roughness, or topography, by way of example. For example, while a void may be a pore in a porous material, a void may also include spaces defined between adjacent features of a rough surface. A rough surface that defines a void may have an average surface roughness ($R_a$) value of greater than or equal to about 0.025 micrometers. The shape of the voids or pores is not limited, but may be any number of shapes including those having a cross-sectional shape of a square, a circle, a rectangle, an oval, a parallelogram, a triangle, or any other regular or irregular cross-sectional or three-dimensional shape.

The overall shape of the three-dimensional scaffold structure may be of any shape, including customized shapes and sizes, and is not correlated with the shape of the void(s). By way of non-limiting example, a square-shaped three-dimensional scaffold structure can include a plurality of circular voids/pores. In certain aspects, the three-dimensional scaffold structure may be an implantable device that is used in vivo and thus introduced into a subject, such as a human. In other aspects, the three-dimensional scaffold structure may be used as for cellular or tissue growth ex vivo or in vitro.

In certain variations, the three-dimensional scaffold structure comprises a plurality of voids. Such voids may be of the same shape and/or in a repeating pattern, but need not be of the same shape. Thus, a shape of each void need not be the same and there is no limitation on the number of voids/pores having the same shape. For example, a scaffold structure can have four voids, one having a triangular cross-sectional shape, two or more having a circular cross-sectional shape, and one having a rectangular or square cross-sectional shape.

In certain aspects, the three-dimensional scaffold structure is a porous material having a plurality of pores. The plurality of pores may optionally be open pores that are interconnected with one another. In certain variations, a pore density may be greater than or equal to about 1 void or pore regions/scaffold material to less than or equal to about $1.0 \times 10^{12}$ void or pore regions/scaffold material. As will be appreciated by those of skill in the art, as the scaffold structure becomes bigger, more pores are added, continuously making the pores smaller and also adding more pores. In certain aspects, the percent open area of the scaffold structure is maximized, so that the scaffold structure may have greater than or equal to about 0.0001% by volume of voids, optionally greater than or equal to about 0.001% by volume of voids, optionally greater than or equal to about 0.01% by volume of voids, optionally greater than or equal to about 0.1% by volume of voids, optionally greater than or equal to about 1% by volume of voids, optionally greater than or equal to about 10% by volume of voids, optionally greater than or equal to about 20% by volume of voids, optionally greater than or equal to about 30% by volume of voids, optionally greater than or equal to about 40% by volume of voids, optionally greater than or equal to about 50% by volume of voids, optionally greater than or equal to about 60% by volume of voids, optionally greater than or equal to about 70% by volume of voids, optionally greater than or equal to about 80% by volume of voids, optionally greater than or equal to about 90% by volume of voids, optionally greater than or equal to about 91% by volume of voids, optionally greater than or equal to about 92% by volume of voids, optionally greater than or equal to about 93% by volume of voids, optionally greater than or equal to about 94% by volume of voids, optionally greater than or equal to about 95% by volume of voids, and in certain preferred aspects, optionally greater than or equal to about 96% by volume of voids.

The void may have a major dimension of greater than or equal to about 0.025 micrometers, optionally greater than or equal to about 0.1 micrometers to less than or equal to about 5 centimeters, optionally greater than or equal to about 0.5 micrometers to less than or equal to about 4 centimeters, optionally greater than or equal to about 1 micrometers to less than or equal to about 3 centimeters, and in certain variations, optionally greater than or equal to about 5 micrometers to less than or equal to about 2 centimeters. By major dimension, it is meant the greatest dimension of the void and may be, for example, length, width, or diameter. In certain variations, a void in the form of a pore may have a length of greater than or equal to about 0.1 mm (100 μm) to 1 millimeter for cell culture applications.

Figure 1:
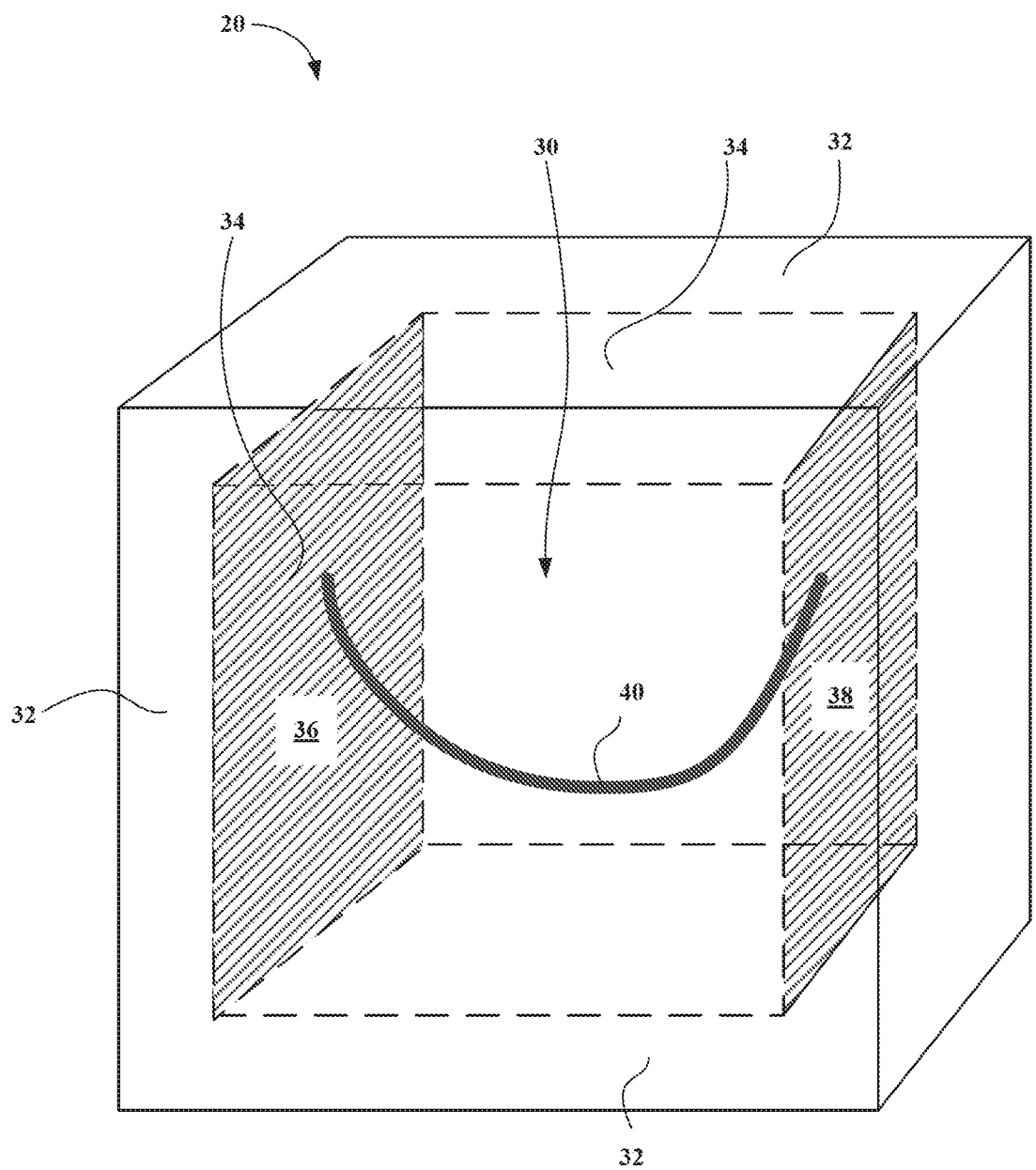
FIG. 1 shows a simplified schematic of a cellular support system having three-dimensional scaffold structure with a single void region and a suspended protein bridge spanning the void region prepared in accordance with certain aspects of the present disclosure.

A simplified non-limiting three-dimensional scaffold structure 20 is shown in FIG. 1. The scaffold structure 20 has an interior void 30 in a representative rectangular shape. The scaffold structure 20 has a single interior void 30 for purposes of illustration, although as discussed above, multiple voids may in fact be present. The scaffold structure 20 includes walls 32 that define and surround the void 30. Interior surfaces 34 of the walls 32 thus define the void 30. A first interior surface 36 and a second interior surface 38 include a protein-containing coating. It should be noted that the coating need not be applied to the entire surface, but may only be applied to discrete regions of the interior surfaces. Further, while the other interior surfaces 34 are not shown to be coated, these may likewise have one or more regions that are coated with the protein-containing coating. As will be described in greater detail below, the scaffold structure 20 also includes one or more suspended protein bridges 40 spanning across the void 30. Thus, the suspended protein bridge 40 is anchored on a first end on the first interior surface 36 and also anchored on a second end on the second interior surface 38. The protein-coating adhered to the first and second interior surfaces 36, 38 can facilitate the anchoring of the protein bridge 40 to the scaffold structure 20. The scaffold structure serves as a skeletal frame and nucleation site for one or more suspended protein bridges 40 which span and fill in the voids/pores 30 of the scaffold structure 20. While not shown, in certain variations, a plurality of suspended protein bridges may form a suspended protein mesh structure.

The scaffold structure 20 thus can promote cell growth in three-dimensions. As noted above, an overall length and width of the three-dimensional scaffold structure 20 is unrestricted and will be dictated by the intended application. By way of example only, scaffold structure 20 may have dimensions of 10 millimeters by 8 mm with a thickness of 0.6 millimeters and have a void/pore that is a single square opening with a side length of 5 millimeters, which may be advantageous for use in laboratory three-dimensional cell culture since this size fits into a centrifuge tube and the well of a 24-well plate.

Figure 2:
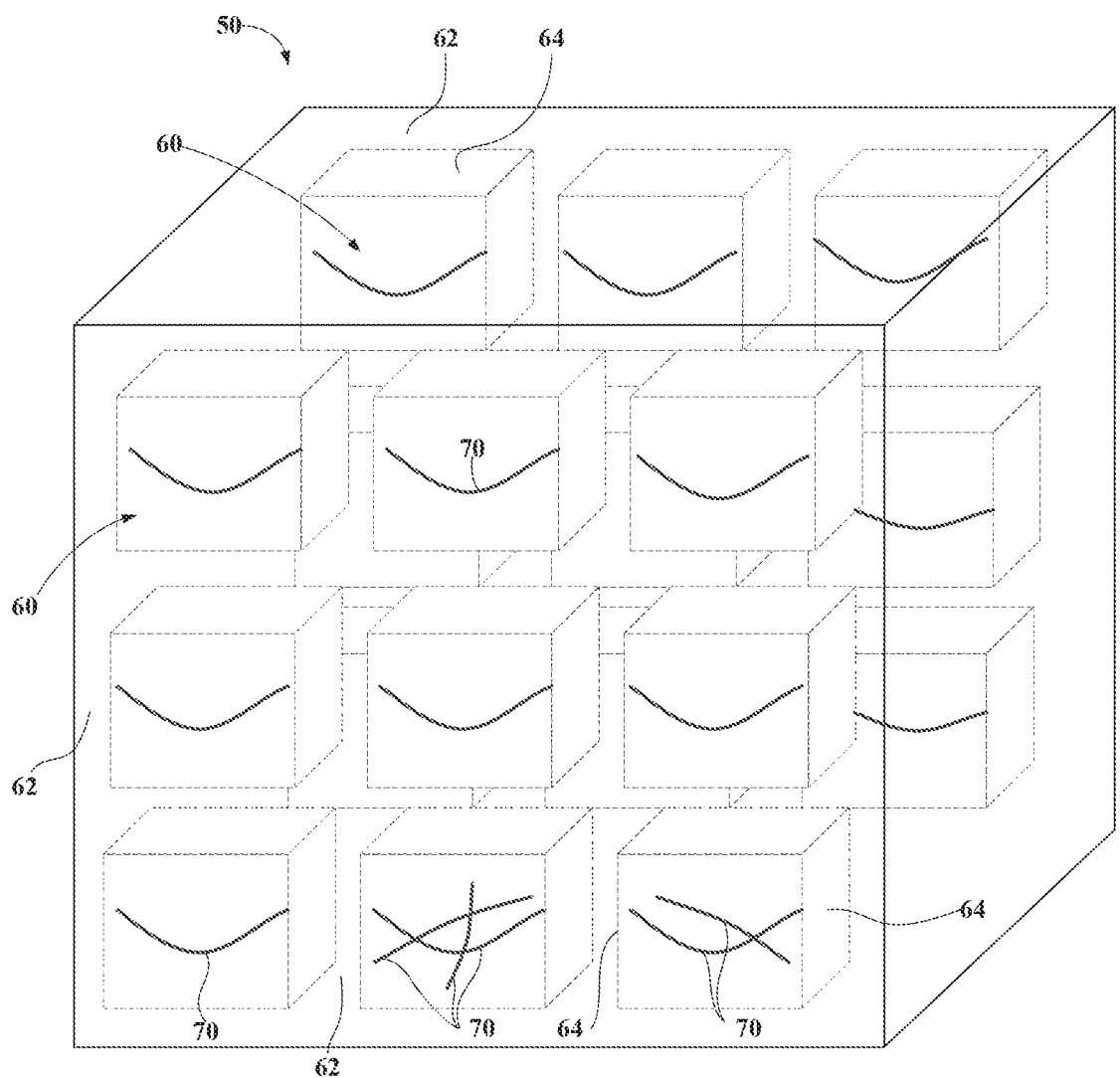
FIG. 2 shows a simplified schematic of another cellular support system having three-dimensional scaffold structure with a plurality of void regions and at least one suspended protein bridge spanning each void region prepared in accordance with certain aspects of the present disclosure.

FIG. 2 shows another simplified non-limiting three-dimensional scaffold structure 50. The scaffold structure 50 has a plurality of interior voids 60 that have a representative rectangular shape in a regular repeating three-dimensional mesh pattern; however, as noted above the voids 60 are not limited to these shapes or positions and may have different shapes and arrangements within the scaffold structure 50. The scaffold structure 50 includes walls 62 that define and surround each void 60. Interior surfaces 64 of the walls 62 thus define the voids 50. As in the embodiment in FIG. 1, any of the interior surfaces 64 may have a protein-containing coating disposed thereon. Each void 60 has at least one suspended protein bridge 70 spanning from a first interior surface 64 to a second interior surface 64 across the void 60 and thus anchored at each end on each respective interior surface 64. While not every void 60 may have a suspended protein bridge 70, in certain variations like that shown in FIG. 2, each void 60 may have multiple suspended protein bridges, including two, three, or multiple bridges 70. For example, each void 60 may have one bridge to thousands of bridges per void, for example, in certain variations, from greater than or equal to about 10 bridges to less than or equal to about 1,000 bridges. In certain aspects, the suspended protein bridges 70 may be a plurality of suspended bridge structures numerous enough to form a suspended protein mesh across the void. It should be noted that while the orientation and position of the protein bridges 70 is shown generally to be the same, they may have different orientations, different anchor points, and therefore different lengths within each void. Further, different voids within the scaffold may have different numbers or densities of suspended protein bridge structures.

In certain aspects, a wall 62 defined between the plurality of voids 60 has an average thickness of greater than or equal to about 0.025 micrometers. In certain variations, a wall 62 defined between the plurality of voids 60 has an average thickness of greater than or equal to about 0.5 micrometers, optionally greater than or equal to about 1 micrometer, and in certain aspects, optionally greater than or equal to about 5 micrometers. In certain variations, a wall may have an average thickness of greater than or equal to about 0.5 micrometers to less than or equal to about 300 micrometers, optionally greater than or equal to about 1 micrometers to less than or equal to about 300 micrometers, optionally greater than or equal to about 5 micrometers to less than or equal to about 300 micrometers, optionally greater than or equal to about 10 micrometers to less than or equal to about 300 micrometers, and in certain variations, optionally greater than or equal to about 100 micrometers to less than or equal to about 300 micrometers. In certain aspects, a depth or major dimensions of each void/pore 60 is less than or equal to a thickness of a wall 62 of the scaffold structure.

In various aspects, the three-dimensional scaffold structure is formed of a biocompatible material. By "biocompatible," it is meant that a material or combination of materials can be contacted with cells, tissue in vitro or in vivo, or used with mammals or other organisms and has acceptable toxicological properties for contact and/or beneficial use with such cells, tissue, and/or animals. For instance, in certain aspects, a biocompatible material may be one that is suitable for implantation into a subject without adverse consequences, for example, without substantial toxicity or acute or chronic inflammatory response and/or acute rejection of the material by the immune system, for instance, via a T-cell response. It will be recognized, of course, that "biocompatibility" is a relative term, and some degree of inflammatory and/or immune response is to be expected even for materials that are highly compatible with living tissue. However, non-biocompatible materials are typically those materials that are highly toxic, inflammatory and/or are acutely rejected by the immune system, e.g., a non-biocompatible material implanted into a subject may provoke an immune response in the subject that is severe enough such that the rejection of the material by the immune system cannot be adequately controlled, in some cases even with the use of immunosuppressant drugs, and often can be of a degree such that the material must be removed from the subject. In certain aspects, biocompatible materials are those that are approved for use in humans by an appropriate regulatory agency, such as the Federal Drug Administration (FDA) in the United States; the European Commission (EC)/European Medicines Agency (EMEA) in Europe; or Health Products and Food Branch (HPFB) in Canada.

In certain variations, the scaffold structure is formed of a biodegradable material, while in other variations; the scaffold structure is formed of a non-biodegradable material. A biodegradable material may dissolve or disintegrate ex vivo or in vivo. "Dissolving" refers to physical disintegration, erosion, disruption and/or dissolution of a material and may include the resorption of a material by a living organism. Dissolution or erosion occurs when the material is exposed to a solvent comprising a high concentration of water, such as growth or culture media, serum, blood, saliva, bodily fluids, and the like. In certain aspects, the three-dimensional scaffold structure optionally comprises a combination of biocompatible materials, like a combination of polymer materials.

The material forming the scaffold structure may include a biofunctional active ingredient that is released as the biodegradable material dissolves or disintegrates. Biofunctional active ingredients or agents may include pharmaceutical active ingredients, proteins, peptides, growth factors, biofactors, imaging agents by way of non-limiting example.

The biofunctional active ingredient may be dispersed within the material that forms the scaffold. Inclusion of a biofunctional active ingredient or agent may be preferred where the scaffold material is biodegradable thus allowing the release of various compounds of interest such as pharmaceuticals or imaging agents.

The three-dimensional scaffold structure can be made of a wide variety of materials, including inorganic and organic biocompatible materials. The three-dimensional scaffold structure may be formed from a material selected from the group consisting of: a metal material, a ceramic material, a glass material, a polymeric material, a composite material (having a polymeric material and a reinforcement material), a ceramic material, a biologically-derived material (a material derived from a biological source, such as cellulose or paper), and combinations thereof and need not be uniform or homogeneous throughout the scaffold structure (e.g., there may be distinct regions of the scaffold with different compositions). Certain polymeric and composite materials may be biodegradable, while other polymeric, composite, and metal materials are not biodegradable. Specifically, biocompatible polymer materials, such as biodegradable or non-biodegradable polymers, synthetic or natural polymers can be used.

By way of example, suitable polymers include polyethers, such as a polyethylene oxide (PEO), polyoxyethylene glycol or polyethylene glycol (PEG), biodegradable polymers such polyesters like polylactic acid, polycaprolactone, polyglycolic acid, poly(lactide-co-glycolide polymer (PLGA), poly (lactide-co-caprolactone), and copolymers, derivatives, and combinations thereof. Suitable water-soluble and/or hydrophilic polymers, which are biocompatible, include cellulose ether polymers like hydroxypropyl methyl cellulose (HPMC), hydroxypropyl cellulose (HPC), hydroxyethyl cellulose (HEC), methyl cellulose (MC), carboxymethyl cellulose (CMC), and combinations thereof. Various polysaccharides include starches such as maltodextrin, amylose, corn starch, potato starch, rice starch, tapioca starch, pea starch, sweet potato starch, barley starch, wheat starch, modified starch (e.g., hydroxypropylated high amylose starch), and the like.

In certain variations, the three-dimensional scaffold structure comprises a polymer and is formed from a polymeric precursor or is a polymer selected from the group consisting of: polylactic acid, polyglycolide, polycaprolactone, poly (lactide-co-glycolide), poly(lactide-co-caprolactone), polyethylene glycol, polydimethylsiloxane, polyurethanes, polyolefins, polyamides, celluloses, lignins, starches, biodegradable polyesters, polystyrene, and combinations thereof.

Other water-soluble polymers among those useful herein include, without limitation, sodium alginate, carrageenan, xanthan gum, gum acacia, Arabic gum, guar gum, pullulan, agar, chitin, chitosan, pectin, karaya gum, locust bean gum, various polysaccharides; starches such as maltodextrin, amylose, corn starch, potato starch, rice starch, tapioca starch, pea starch, sweet potato starch, barley starch, wheat starch, modified starch (e.g., hydroxypropylated high amylose starch), dextrin, levan, elsinan and gluten; and proteins such as collagen, whey protein isolate, casein, milk protein, soy protein, keratin, and gelatin.

The choice of the scaffold structure material can vary based upon the intended application of the cell culture system. When used to facilitate three-dimensional culture of adherent cells, polymeric materials may be advantageous by providing a softer mechanical environment. These include, without limitation, polylactic acid, polyglycolide, polyethylene glycol, polycaprolactone, starches, biodegradable polyesters, co-polymers such as poly(lactide-co-glycolide) and poly(lactide-co-caprolactone), and non-degradable materials such as polystyrene. If intended for long-term use, or as an implant with intention of surgical removal, a metal scaffold may be preferred for rigidity, stability, and lack of degradability.

In certain aspects, the three-dimensional scaffold structure can be chemically anisotropic. This may be achieved, for example, by reacting or tethering different functional groups to localized areas of select surfaces of the scaffold structure. Chemical anisotropy can also be realized by compartmentalizing the bulk material of the scaffold structure into domains of varying chemical composition.

In certain aspects, the three-dimensional scaffold structure may be custom-made or commercially available. Scaffolds can be custom made with desired opening sizes and shape. For polymeric scaffolds, fabrication options include without limitation, solid free form fabrication, additive manufacturing (e.g., 3D printing, 3D jet writing, direct writing), and extrusion. Metal scaffolds, again without limitation, can be milled, machined, photochemically etched, or formed via additive manufacturing (e.g., direct metal laser sintering). In certain aspects, three-dimensional scaffold structures may be formed via photolithography from a suitable commercially available resist SU-8 sold by MicroChem, which is a negative tone photoresist high contrast epoxy based material. In other aspects, the three-dimensional scaffold structure may be formed from non-woven electrospun polymeric microfiber mats. In another aspect, three-dimensional scaffold structure may include an array of micropillars. Another suitable commercially available three-dimensional scaffold structure further includes a mesh filter screen commercially available from Component Supply. In other certain variations, the three-dimensional scaffold structure may include a non-woven fiber mat, a woven fiber mat, or paper substrate.

Protein Bridge Structures

The cellular support system also includes at least one suspended protein bridge spanning across the at least one void in the three-dimensional scaffold structure. The suspended protein bridge comprises at least one protein. A protein as used herein is a polypeptide chain comprising bonded amino acids, where the polypeptide chain has undergone folding (including primary, secondary, and tertiary folding) to form the complex folded molecule. In certain aspects, the protein has greater than 50 amino acids. The protein is initially dissolved as a solubilized protein in a liquid. After conducting the methods described herein, the dissolved protein is transformed into an insoluble protein bridge, notably without the need for use of cells to do so. The final product of the suspended protein bridge may comprise an insoluble molecule formed into a complex folded shape. The complexly folded molecule is insoluble in water and aqueous solutions, preferably is fibrillar, and is also biologically active to cells in the environment.

The proteins selected for use in the cellular support system are those proteins that can form suspended protein bridges across or within the voids/pores of the aforementioned three-dimensional scaffold structure. Different proteins can be combined to form suspended protein supports of varying composition. Importantly, proteins that do not form suspended protein supports can be combined with/co-assembled with proteins that do form suspensions to create bridge structures containing multiple proteins. Thus, the composition forming the protein bridge may comprise a plurality of distinct proteins.

In certain preferred aspects, the suspended protein bridge comprises one or more extracellular proteins. In certain variations, the suspended protein bridge comprises one or more extracellular matrix proteins. An extracellular matrix protein is one or more of the large structural fibrillar proteins often found physiologically in the extracellular matrix (ECM) of animals or plants. In certain variations, the suspended protein bridge comprises one or more proteins selected from the group consisting of: collagens, laminins, fibronectins, tenascins, elastin, vitronectin, periostin, and combinations thereof. In other variations, the suspended protein bridge comprises one or more proteins selected from the group consisting of: collagens, laminins, fibronectins, and combinations thereof. As noted above, the suspended protein bridges can include mixtures of such proteins, each at different relative ratios. In certain variations, a ratio of fibronectin to laminin in a protein mixture may be at a ratio of about 9:1. In other variations, a ratio of fibronectin to tenascin c may be at a ratio of about 19:1. The protein material forming the suspended protein bridges may also form a surface coating on one or more regions of the interior surfaces of the scaffold structure voids/pores. As noted above, the coating may serve to structurally and mechanically anchor the suspended protein bridge to an interior surface of the void of the scaffold structure. In this manner, the suspended protein bridge is capable of spanning regions of the void while supporting the additional weight of cells that adhere to it.

In certain aspects, the three-dimensional scaffold structure of the cellular support system comprises a polymer. A protein loading density in the cellular support system is greater than less than or equal to about 8 milligrams of protein per milligram of the polymer in the cellular support system. By way of example, a suitable protein loading density may be 100 micrograms of protein per milligram of polymer.

In certain aspects, the suspended protein bridge extends down into each void at a depth ranging from greater than or equal to about 30% of a scaffold wall thickness up to about 100% of a scaffold wall thickness adjacent to the void. Notably, in other variations, the suspended protein bridge only forms across a surface of the scaffold, rather than necessarily extending into a depth of the void. In certain variations, the suspended protein bridge may form across a rough surface defining a void on the scaffold the surface.

Global stiffness of the protein-scaffold structure and compressibility of the suspended protein bridges can be tuned by modifying the scaffold composition, and/or modulating pore shape and size. Larger voids/pores in the scaffold structure will favor greater compressibility, whereas smaller voids/pores will favor stiffer protein bridges.

Larger pores given a fixed scaffold length and width also reduces interactions between the protein and solid scaffold surfaces, tending to maintain the protein in its native conformation. This also minimizes exposure of adherent cells (if any) to synthetic scaffold material (if synthetic) to preserve cell phenotype and maintain natural cell behavior.

This technology can decouple mechanical properties from chemical composition by tuning the geometry of the scaffold structure and/or its voids/pores. This is a problem that often arises with hydrogels (chemical crosslinking, for example).

The suspended protein bridge thus provides cells with an ECM-like network of protein which is susceptible to remodeling by the cells, allowing for study of cell migration and metastasis, which is a unique aspect of the inventive technology. When cells secrete insoluble proteins to form their microenvironment, they are also revealing biologically active cryptic binding sites on the protein that are otherwise inaccessible to cells when the protein is solubilized. Here, because the proteins present in the protein bridge are insoluble, the cryptic binding sites can be revealed despite being fully-defined and cell-free.

The suspended protein bridge is thus capable of supporting cells and promotes three-dimensional cellular growth. By "promoting" cell growth, cell proliferation, cell differentiation, cell repair, or cell regeneration, it is meant that a detectable increase occurs in either a rate or a measurable outcome of such processes when the cellular support system is present as compared to a cell or organism's process in the absence of the cellular support system, for example, conducting such processes naturally. By way of example, as appreciated by those of skill in the art promoting cell growth in the cellular support system may increase a growth rate of target cells or increase a total cell count of the target cells, when compared to cell growth or cell count of the target cells in the absence of such a cellular support system. By "supporting" cell growth, cell proliferation, cell differentiation, cell repair, or cell regeneration, it is meant that the cellular support system provides a physical substrate for one or more target cells that enhances target cell growth, vitality, proliferation, differentiation, repair, or regeneration, by way of non-limiting example. As appreciated by those of skill in the art, the cellular support system may both support and promote the growth, vitality, proliferation, differentiation, repair, and/or regeneration processes of one or more target cells in vitro, ex vivo, or in vivo, for example. The cellular support system thus can serve a role as a cellular scaffold structure that supports and/or promotes target cell growth, target cell proliferation, target cell differentiation, target cell repair, and/or target cell regeneration in three-dimensions, in contrast to the support and growth on conventional two-dimensional planar or two-dimensional scaffold surfaces. The cellular support system of the present disclosure can be employed to promote growth of one or more target cells in a predetermined three-dimensional pattern.

The suspended protein bridges can be lyophilized for long-term storage, transport, and analysis. The protein bridges can also last in an aqueous solution without degradation, as fabricated, for over one week.

Cellular Support System

The cellular support system provided by the present disclosure, including suspended protein bridges, is thus capable of supporting cells and promotes three-dimensional cellular growth. Thus, use of the protein bridge supports in the void(s) of a three-dimensional support structure creates a three-dimensional cell culture system. The suspended protein bridges provide a biocompatible environment that simulates in vivo conditions for the culture of cells in vitro. In certain variations, the cells can be pluripotent stem cells, embryonic stem cells, adult stem cells, cancer stem cells, and the like. The cellular support system is capable of maintaining the pluripotency of stem cells for long periods, e.g., over a month.

Adherent cells may be derived from any species and include but are not limited to: 1) commercially available, established cell lines; 2) primary cells; and/or cells isolated directly from a human patient and may include, without limitation, of: i) embryonic stem cells; ii) adult stem cells; iii) induced pluripotent stem cells; iv) somatic cells; and/or v) cancer cells, by way of non-limiting example.

Adherent cells have been observed to form sheets that span the voids of the three-dimensional scaffold structure of the cellular support system, facilitated by the presence of one or more suspended protein bridges, in accordance with various aspects of the present disclosure. Other cell architectures have also been observed such as cell clusters spotted periodically across the voids of the scaffold structure. Cells residing within the voids/pores experience minimal interaction with the scaffold structure material making cells less likely to display an artificial phenotype, often induced by other two dimensional (2D) and three-dimensional (3D) cell culture systems. Thus, in certain aspects, the percent open area of the scaffold structure is maximized.

The microenvironment formed by the suspended protein bridges provides cells with an ECM-like network of protein that is susceptible to remodeling. These proteins contain binding sites to which cells adhere. Cells can therefore embed themselves among the protein bridges within three-dimensional (3D) space, as opposed to simply sitting atop a conformal protein coating on a two-dimensional (2D) substrate. Cells can break down or remodel the suspended protein bridge/support to suit their needs and create their own cell niche as is done in vivo. This is a feature unique to the cellular support systems of the present teachings. Conformal protein coatings cannot be remodeled by cells to form their desired microenvironment. Hydrogels of proteins cannot be broken down by cells because the protein and the structural support are coupled. In certain aspects, the inventive technology allows cells to completely break down the suspended protein, while still providing a structurally sound environment within the support of the scaffold structure. An example of this is given in FIGS. 12A-12B showing MDA-MB-231 breast cancer cells on suspended protein supports as a metastatic model.

To administer adherent cells to cellular support systems formed according to certain aspects of the present disclosure, cells may be suspended in a biocompatible fluid or cell media. This suspension is highly concentrated and deposited in a droplet onto a cellular support system, or the cellular support system is allowed to incubate in the cell suspension. Static or dynamic incubation conditions are both feasible. Contact time between the cells and the protein-scaffold construct, or scaffold, may be at least 10 minutes. During this time, cells are housed at 37° C. and 5% $CO_2$. After cells invade or seed onto the cellular support system, standard cell culture techniques apply for the growth, maintenance, and proliferation of the cells.

Alternatively, cells can be seeded onto the cellular support system and maintained in more non-traditional cell culture systems, such as a bioreactor.

Notably, the use of suspended protein bridges in cellular support system forming a 3D cell culture places no restriction on external environmental control mechanisms which can include, without limitation, static incubation at 37° C. and 5% $CO_2$ or housing in a bioreactor.

Cell proliferation has been found from the time of seeding to confluency to increase 16-fold on suspended protein bridges in cellular support systems prepared according to certain variations of the present disclosure, but only a 6-fold on tissue culture polystyrene. In certain variations, the cellular support system according to the present disclosure enhances cancer stem cell populations. In one variation, a 100% success rate in cultivating primary human breast cancer patient cells in vitro with maintenance of receptor status is observed when grown in cellular support systems prepared according to certain variations of the present disclosure. Suspended protein bridges further offer an ability to study of the effect of ECM composition on cell behavior. This includes the effect of individual ECM proteins and specific combinations of distinct ECM proteins.

In various aspects, cellular support systems provided by the present disclosure can be used in applications for the culture of cells including without limitation: stem cells differentiated directly on the scaffold/cellular support system; scaffolds/cellular support systems folded into higher order 3D structures such as tubes to guide formation of cell-based architectures; scaffolds/cellular support systems used with bioreactor systems for 1) production of proteins or enzymes by cell secretion, 2) differentiation of stem cells to a specific, desired cell type; and highly repeatable growth or proliferation of cells under tightly controlled culture conditions to generate tumors on scaffolds a) from cancer cell lines, and b) from cells isolated directly from cancer patients; personalized drug screening on patient derived tumors developed on scaffolds/cellular support systems; delivery of cells in cell-based therapies in vivo, where the scaffold/cellular support system provides a method of integrating cells in a protein matrix prior to implantation for regenerative purposes; and/or investigation of cell responses based on the composition of the surrounding extracellular matrix.

Thus, three-dimensional (3D) cellular support systems prepared in accordance with the present disclosure and used as a cell culture platform are unlike any other currently known tissue scaffolds in that the protein is in an insoluble fibrillar ECM-like network. Previously, insoluble fibrillar ECM-like proteins have only been secreted by cells. For the first time, a fully defined suspended protein support can be manufactured in a cell-free system. Cells are then able to infiltrate this space, tethering to the protein in vitro as it would physiologically to the extracellular matrix in vivo. A major advantage is the ability for cells to remodel their proteinaceous environment. Physiologically, cells break down extracellular matrix proteins and secrete them again in a continuous process known as remodeling. Certain cells may break down matrix proteins more than others, while other cells may secrete particular proteins in higher quantities. Cell mobility is often tied to the breakdown of matrix proteins. Making it possible to tune the composition and mechanical properties of the suspended protein support bridges, the cellular support system according to the present disclosure provides a superior and physiologically relevant 3D cell culture platform as compared to those currently available. Thus, the inventive cellular support systems provide a vast improvement over current state of the art for cell-delivery applications, and have demonstrated improved tumor grafting efficiency in mice.

Methods of Making Cellular Support Systems

In certain aspects, the present disclosure provides methods of making a cellular support system. Such methods may include synthesizing a suspended insoluble protein bridge from a solubilized protein precursor, without the use of cells, to form a cellular support system. Such methods can be conducted without any use of cells, which have been used in previous techniques for such a transformation. The present disclosure thus provides a method of making a cellular support system comprising positioning a three-dimensional scaffold structure comprising at least one void at a two-phase interface in a container comprising a liquid comprising a protein and a second fluid, such as a liquid or gas. The protein may thus be a solubilized protein. In certain variations, the second phase is a gas, such as air. In other variations, the second fluid phase may be a liquid and may optionally carry a solubilized protein. Thus, a three-phase interface may be defined by the solid three-dimensional scaffold structure being disposed at the two-phase interface defined between a first liquid phase and a second fluid phase.

The method further includes flowing or passing liquid past the three-dimensional scaffold structure to dynamically incubate the protein, so as to form a suspended protein bridge spanning across the at least one void. In certain variations, the passing of the liquid may comprise moving the three-dimensional scaffold structure so that the liquid flows past it to dynamically incubate the protein thereon. In other aspects, the scaffold structure may be stationary and the liquid may flow past it for the dynamic incubation. For example, the liquid comprising the protein may be sparged or bubbled in the container to pass the liquid over the three-dimensional scaffold structure. After the process of formation, the suspended protein bridge may be insoluble. The suspended protein bridge is capable of supporting cells and promotes three-dimensional cellular growth.

In certain aspects, the passing is conducted by moving the three-dimensional scaffold structure so that the liquid flows past the three-dimensional scaffold structure to dynamically incubate the protein so as to form a suspended protein bridge spanning across the at least one void. The moving may be selected from the group consisting of: orbital rotation, tumbling rotation, vibration, and shaking. The passing for dynamic incubation may occur for greater than or equal to about 5 minutes to less than or equal to about 24 hours, optionally for greater than or equal to about 15 minutes to less than or equal to about 24 hours, and in certain variations, optionally for greater than or equal to about 1 hour to less than or equal to about 24 hours.

The liquid comprising protein may be a protein solution having a concentration of protein from about 0.01 mg/mL to about 1 mg/mL. The materials used in this method may be any of those previously described above. In certain variations, the protein comprises one or more extracellular proteins, optionally one or more extracellular matrix proteins. By way of example, the protein is optionally selected from the group consisting of: collagens, laminins, fibronectins, tenascins, elastin, vitronectin, periostin, and combinations thereof. The three-dimensional scaffold structure is formed from a material selected from the group consisting of: a metal material, a polymeric material, a ceramic material, a biologically-derived material, a composite material, and combinations thereof. In certain aspects, the three-dimensional scaffold structure comprises a polymer and is formed from a polymeric precursor or is a polymer selected from the group consisting of: polylactic acid, polyglycolide, polycaprolactone, poly(lactide-co-glycolide), poly(lactide-co-caprolactone), polyethylene glycol, polydimethylsiloxane, polyurethanes, polyolefins, polyamides, celluloses, lignins, starches, biodegradable polyesters, polystyrene, and combinations thereof.

In certain aspects, the present disclosure contemplates a fully synthetic cell-free method of synthesizing insoluble protein bridges from solubilized protein starting materials. The final insoluble protein bridge may thus be formed with a correct folded conformation when formed in this cell-free technique.

Figure 3:
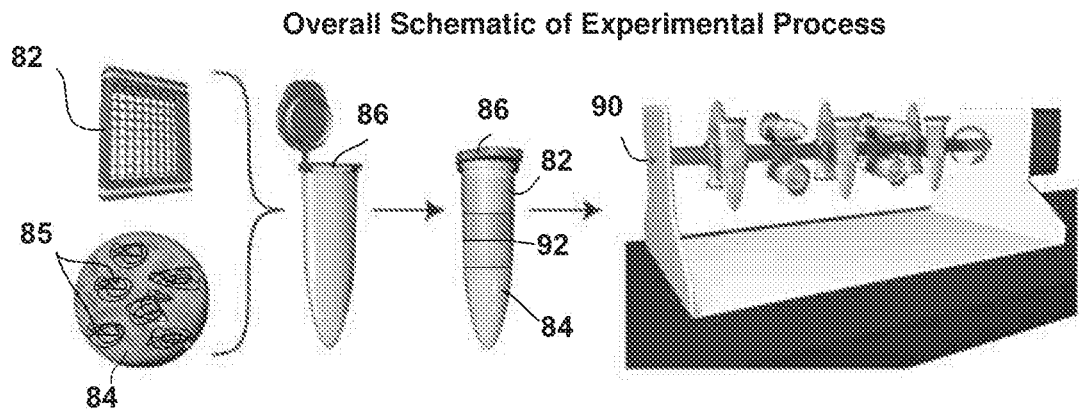
FIG. 3 shows a schematic of a process for forming a cellular support system having a three-dimensional scaffold structure with a plurality of void regions and at least one suspended protein bridge spanning each void region prepared in accordance with certain aspects of the present disclosure.

FIG. 3 shows a representative schematic of an exemplary system configuration in which such a method can be conducted. A porous membrane 82 is used as a three-dimensional scaffold structure having a plurality of void regions, while a liquid protein solution 84 includes an extracellular protein 85. The porous membrane 82 is also shown in FIGS. 4A-4B. The liquid protein solution 84 is added to a sealable container 86 (e.g., a micro-centrifuge tube) and then the porous membrane 82 is positioned midway within the container 86. One or more sealable containers 86 are affixed on a rotator device 90. The containers 86 are rotated on the rotator device 90 for a predetermined amount of time.

The porous membrane 82 is positioned at an air-liquid interface 92 within the container 86. As the container moves or rotates, the liquid protein solution 84 flows past the porous membrane 82 shifting the air-liquid interface 92 somewhat. FIG. 4C shows comparative static incubation conditions, while FIG. 4D shows dynamic incubation conditions in accordance with certain aspects of the present disclosure. In FIG. 4C, the porous membrane 82 is fully submerged in the liquid protein solution 84. In FIG. 4D, the porous membrane 82 is secured at the air-water interface 92 in container 86. Thus, as the container 86 rotates, the air-water interface 92 translates through the porous membrane 82 at different angles, but remains at or near the porous membrane 82.

Under static incubation conditions shown in FIG. 4C, a conformal protein coat forms on the surface of the porous membrane 82. In contrast, under dynamic incubation conditions like that in FIG. 4D, fluid continuously flows (as shown by the direction arrows) and a suspended mesh of protein bridge structures are formed in the voids of the porous membrane 82. In one variation, the container 86 (e.g., micro-centrifuge tube) is tumbled on the rotator device 90 at a set temperature for a fixed amount of time. For a fibronectin protein, the rotation/tumbling is conducted for two hours at about 30° C. to form the suspended mesh of protein bridges.

In various aspects, the scaffold structure is incubated in a solution of one or more proteins. These proteins in solution will dictate the protein composition of the final product. The relative amount of each protein in solution is an expected ratio of each protein relative to each other in the final product. Thus, most or all of the protein is dissolved in solution. If the suspended protein bridges comprise more than one type of protein, then those proteins are included and dispersed in the solution at the desired ratio. The final overall protein concentration, whether comprised of one or more proteins, is greater than or equal to about 0.1 microgram per milliliter of the total liquid composition.

In one variation, a final product having approximately 80% by mass of the protein is fibronectin and 20% laminin, 0.08 mg of fibronectin and 0.02 mg of laminin are dissolved per milliliter of aqueous solution. The amount of each protein may also be adjusted such that the proteins are dissolved in a desired molar ratio rather than mass ratio.

Alternatively, incubation of the three-dimensional scaffold structure with multiple proteins can be done sequentially in solutions of at least one protein at a time. This might be desired to prevent certain interactions between multiple proteins while incubating.

Incubation conditions are flexible and based on the protein(s) of interest. The contact time, protein solution concentration, incubation temperature, and fluid flow conditions are optimized in order to determine the set of parameters under which the protein(s) form suspended protein supports within or across the scaffold structure's void(s).

1. Contact Time

The time in which the scaffold structure is in contact with the protein solution can vary depending on the protein(s); but typically contact time ranges from greater than or equal to 5 minutes to less than or equal to about 24 hours. In certain aspects, the contact time may be greater than or equal to about 1 hour to less than or equal to about 24 hours. Generally, a longer contact time tends to favor a higher protein loading onto scaffold structure and stronger protein adhesion.

2. Protein Solution Concentration

Some proteins require a higher concentration in solution. The exact concentration will vary based on the solution surface tension, ionic strength, and desired protein loading, but in certain preferred aspects, a suitable protein solution concentration ranges from about 0.01 mg/mL to 1 mg/mL.

3. Incubation Temperature

Temperature during incubation must be selected carefully to prevent protein denaturation that can occur when temperatures are too high. Again, different proteins and substrates may result in different optimal incubation temperatures. In one aspect, a suitable range of incubation temperatures is greater than or equal to about 4° C. to less than or equal to about 40° C. In certain aspects, it may be desirable to incubate in sequences of different temperatures for the duration of the contact time.

4. Fluid Flow

The scaffold structure is incubated under at least two-phase flow. The first phase is the liquid protein solution, which is transferred to a liquid tight container at a volume that only partially fills the container. The remaining volume of the container contains the second phase, typically air or another gas. The scaffold is the third phase, and is held in a position at the interface of the liquid protein solution. Fluid flow then ensues. Fluid flow can be achieved by several methods, without limitation, orbital rotation, tumbling rotator, vibration, or shaking.

In one variation, a three-dimensional scaffold structure having at least one void is secured at the center of the interface to ensure an even protein density. Positioning the substrate with a bias to one side or another will result in a tendency for more protein to adsorb to one side of the scaffold substrate than the other. This can be advantageous if a spatial gradient in protein loading throughout the scaffold is desired. Failure to secure the scaffold at the absolute midpoint of the two-phase system does not compromise an ability to form a protein suspension across a void; it is only to provide a uniform protein density, if desired.

FIG. 20 shows a schematic of one variation of proper positioning of an air-liquid matrix near a three-dimensional scaffold structure during rotation in accordance with certain aspects of the present disclosure. Process conditions dictate the formation of suspended protein mesh, so that superporous polymer membranes serve as supports for the suspended protein mesh, and are either fully submerged in the bulk protein solution or secured at the air-water interface. As noted above, under static incubation conditions, a conformal protein coat forms on the polymer surface. In contrast, with fluid flow under dynamic incubation conditions, a suspended protein mesh forms throughout the polymer support. In FIG. 20, open circles indicate proper position of the scaffold structure at the air-liquid interface when the container is held vertically, while the crossed-out circles show incorrect position for this variation.

Once the scaffold structure is positioned and secured at the two-phase interface, the entire system is subjected to dynamic conditions in order to induce flow of the protein solution air interface over the scaffold. This can be achieved by mounting the liquid tight container to a rotisserie rotator, orbital shaker, or the like. Alternative methods to exposing the scaffold to the interface between the protein solution and the second phase (typically air) include but are not limited to dip coating, sparging, and bubbling. In various aspects, the present disclosure contemplates all methods of shearing a fluid interface over or across a scaffold structure having at least one void. The scaffold structure and its voids/pores act as a nucleation site for the protein to form suspended protein supports or bridges.

5. Overall Optimization

Each of the aforementioned incubation parameters may be tuned to produce the desired suspended protein bridge characteristics. The list of parameters includes: (i) number of different proteins to be suspended (one or more); (ii) types of protein(s) to be suspended; (iii) if multiple proteins are desired 1) a ratio of proteins relative to the others; and/or 2) scaffold incubation in one solution that is a mixture of multiple proteins, or consecutive incubation periods in solutions of one protein at a time; (iv) concentration of protein solution(s); (v) time in which scaffold structure will be in contact with protein solution; and (vi) temperature(s) at which scaffold structure will be incubated with protein solution.

Methods of inducing two-phase flow, where a liquid protein solution interface flows and shears over the scaffold, include by way of example: 1) shaker motion; 2) rotisserie rotation; 3) bubbling; 4) dip coating; and/or 5) sparging.

The resulting suspended protein support can be visually described as a network of protein that adsorbs onto the solid surfaces of the scaffold structure including the surfaces of the inner walls of the void(s)/pore(s), and may also extend as a web into the void space of any openings or across any surface features on the scaffold structure. This effectively forms insoluble protein bridges that are suspended within and across the voids(s) of the scaffold structure. Furthermore, the organization of the protein into insoluble structures formed from such a process (1) distinguishes the inventive technology from unorganized hydrogels; (2) resembles the insoluble fibrillar network of fibers that form the extracellular matrix in vivo; and/or (3) presents cells with biologically active and meaningful conformations of the suspended protein.

FIGS. 5A-5F show LSCM images of fibrillar networks of fibronectin suspended within scaffold pores. FIGS. 5B, 5D, and 5E-5F show protein bridge networks that facilitate tissue formation in cellular support systems in accordance with certain aspects of the present disclosure. FIG. 5A shows an LSCM image of a conformal protein coat resulting from static incubation of a porous polymer scaffold in fibronectin protein solution. FIG. 5B shows an LSCM image of a suspended protein mesh formed within open pores of a porous polymer scaffold after incubation at the air-water interface under dynamic conditions. FIG. 5C shows that after three days of culturing NIH-3T3 fibroblasts on conformal fibronectin coats, cells only tend to adhere along the polymer fibers. FIG. 5D shows that when NIH-3T3 fibroblasts are cultured three days on the suspended fibronectin mesh, the fibroblasts fill all pores to depths of several cell diameters thick indicating suspended protein mesh yields superior cell proliferation and tissue formation results. FIG. 5E shows a 3D volume view showing depth of tissue created by cells in culture on a suspended protein bridge mesh in a cell culture scaffold formed in accordance with certain aspects of the present disclosure. FIG. 5F shows a top view of the same cell culture scaffold as in FIG. 5E showing interconnectivity of cells on suspended protein mesh. Channels: blue, polymer microfibers; green, fibronectin; red, actin; cyan, cell nucleus.

Example 1

Suspended fibronectin fibrils are assembled across polymeric scaffold structures fabricated via 3D jet writing. The scaffolds have a checkerboard-like array of square-shaped pores each 0.5 mm in length. First, 0.1 mg of fibronectin is dissolved in 1 mL of phosphate buffered saline within a 2-mL micro-centrifuge tube. The materials used herein are as follows: Fibronectin, Human, 5 mg (356008) commercially available from Corning; Gibco DPBS, calcium and magnesium free; metal frames are custom made, N45 Neodymium ¼"×⅛"×1/16" rare earth magnets, neon latex orthodontic elastics—4.5 oz. ⅛"—Medium Pull; Micro-centrifuge Tube: VWR Micro-centrifuge Tube with X-Resin™ 2 mL Clear Nonsterile 89511-266 commercially available from Biotix; an incubator at 30° C. and rotator for micro-centrifuge tubes that fits inside incubator. The scaffold is mounted in the centrifuge tube parallel to the air-protein solution interface that forms when the tube is lying on its side. The midpoint of the scaffold is aligned with the air-protein solution interface when the tube is standing vertically.

Mounting and Positioning Scaffold Structures into Frames

The frames are sterilized by spraying with ethanol. The scaffold is held with fine tip tweezers and then lightly sprayed with 70% ethanol on both sides to sterilize. The scaffold is easier to mount in frames when scaffold and frames are damp. Each scaffold requires two frames (so that scaffold is sandwiched in between).

Next, one frame is laid down on a sterile surface. While damp, the scaffold is placed onto a frame such that the scaffold is aligned with open square area. Using a fine tip tweezer, a second frame is placed on top to evenly sandwich scaffold in between.

To secure the scaffold between frames, place a rubber band within grooves on the two ends of the frames. Fine tip tweezers are helpful, but there are various ways to achieve this mount. Ideally, the scaffold does not shift as the rubber bands are being placed. Also, it is beneficial to avoid applying too much pressure on the frames while the scaffold is in between, as this may cut the scaffold structure or sever the fibers. The tube/container now contains the scaffold and an aliquot of liquid protein solution is then added.

Forming Aliquot

DPBS is chilled until cold and kept on ice for aliquoting.

On ice, DPBS is added to a fibronectin bottle as commercially obtained to achieve a concentration of 1 mg/mL. The commercially obtained bottle is gently rotated until all protein is dissolved.

100 µL of protein solution are aliquoted into a non-fouling 2 mL micro-centrifuge tube. All solutions are kept on ice for duration of aliquoting.

The aliquots can be stored at −20° C. Then, one 100 µL aliquot can be thawed at 4° C. for 10-15 minutes or until thawed. One aliquot is added to each container/vial having a scaffold structure positioned therein.

800 µL of DPBS (calcium and magnesium free) is added to each thawed aliquot without allowing the pipette tip to touch the fibronectin to avoid adsorption of protein on the pipette tip.

The tube is gently rocked and rotated by hand to ensure the solution is freely flowing under rotation in all directions. All surfaces within the micro-centrifuge tube are able to be wetted by protein solution. When tilting the tube in any direction, the solution flows from one end to the other. Flicking the tube may also be helpful. It is desirable to avoid bubbles as much as possible.

The framed scaffold structure (previously mounted in a metal frame in earlier steps within the container) is introduced into protein solution and the tube is closed. The scaffold and frame are desirably air dried to remove all ethanol. The tube may be flicked to remove any bubbles that form within scaffold structure pores. Again, avoiding bubbles is desirable to the extent possible.

A magnet may be placed on the side of the container/tube. Holding the tube vertically, the magnet may be slid up and down the outer side of the tube until the middle of the scaffold frame is aligned with air-water interface. Turning the tube on its side, enables checking that the scaffold frame is level and at the center of the tube. The magnets may be secured (e.g., with tape) to hold scaffold frame in this position.

This tube, now containing the scaffold and 0.9 mL of fibronectin solution, is secured to a rotisserie rotator. One or more tubes may be mounted onto a rotator. The rotisserie rotator is placed in an incubator at 30° C. and the scaffold structure is rotated, end-over-end, in the fibronectin solution for two hours at a rate of eight full rotations (360° of rotation) per minute. See for example, FIG. 3.

Next, the protein solution may be removed. The tube with the scaffold structure can be rinsed multiple times (e.g., 3 times) with DPBS. The protein scaffolds in DPBS can be stored in micro-centrifuge tube at 4° C. This results in a fibronectin loading of about 55 μg per mg of polymer material; in other words, the protein loading equates to about 6% of the scaffold mass. Additionally, the fibronectin forms web-like bridges across the square pores, where the solid scaffold material between openings serves as structural pillars for the suspended protein. This suspended fibronectin extends down into the opening of each pore at depths ranging from 50 to 150 micrometers, or 30% to 100% of the scaffold thickness. Ideally, such protein scaffolds are used within 1 week or subsequently lyophilized by known techniques to extend shelf-life of the cellular support system comprising a three-dimensional scaffold structure having a suspended protein bridge spanning at least one void.

Example 2

Suspended protein support compared to a non-woven fiber mat. A non-woven electrospun polymer microfiber mat is subjected to the same protocol used for suspended fibronectin supports on 3D jet writing scaffolds described in Example 1. The result is the formation of suspended protein supports similar to those that have been formed traditionally on 3D jet writing scaffolds. Samples of different areas of the suspended protein support on the non-woven electrospun mat show good three-dimensional cell growth. This result shows that the scaffold structure need not comprise large open areas, but rather certain surface features, pores, roughness, or topography to serve as a nucleation site for the formation of insoluble protein structures from the protein solution interface.

Without the three dimensional protein space provided by the suspended protein support, the growth of cultured cells, here, human mesenchymal stem cells, is strongly limited in the z-direction. Suspended protein bridges lead to 3D cell structures more like a tissue, rather than a mono- or bi-layer of cells on a surface.

Example 3

The materials and components used in this example are the same as those listed in Example 1, except the protein is laminin instead of fibronectin. The laminin is mouse laminin commercially available as 23017-015 (liquid) from Life Technologies. A Super Glue Longneck Bottle from Loctite Adhesives (liquid, not gel) is also used. First, an aliquot of 300 μL of laminin solution is placed into a non-fouling 2 mL micro-centrifuge tube. All solutions are kept on ice for duration of aliquoting. The aliquots are stored at −20° C.

Mounting and Positioning Scaffold Structures into Frames

The frames are sterilized by spraying with ethanol. Holding the scaffold with fine tip tweezers, the scaffold is lightly sprayed with 70% ethanol on both sides for sterilization. The scaffold is easier to mount in frames when scaffold and frames are damp. Each scaffold requires two frames (so that scaffold is sandwiched in between).

Next, one frame is laid down on a sterile surface. A line of LOCTITE™ super glue is applied around the outer edge of the square opening of the frame. The scaffold structure is placed onto the frame such that scaffold structure is aligned with open square area. The edges of the scaffold structure are well wetted in the line of super glue. Using fine tip tweezer, the second frame is placed on top to evenly sandwich scaffold in between. The super glue cures for 30 minutes, fixing the scaffold in between the frames. Too much applied pressure is avoided while the scaffold is in between, as this may cut the scaffold or sever the fibers. The mounted scaffold is then rinsed three times for 10 minutes each in DI water.

Process: Forming Protein Mesh on Scaffolds

The steps for forming the protein bridges on the scaffold structure are the same as those described above in Example 1, except for laminin, 700 μL of DI water (not DPBS) is added to the 300 μL aliquot. Also, the incubation is for 2 hours at 26° C. (rather than 30° C.). After incubation, DI water is used for triple washing rather than DPBS. The laminin mesh constructs thus formed are stored in DI water at room temperature rather than at 4° C., because colder temperatures cause the laminin to resolubilize.

Example 4

The same components as those listed in Example 1 are used, except instead of fibronectin protein, collagen type I as extracted from the tail of a rat is used. The other components include 33 mM Acetic Acid, 0.34 N NaOH, and Dulbecco's DMEM (as purchased, without additives such as serum).

Collagen Stock Solution and Aliquot

First, a 50 mL falcon tube is weighed. The lyophilized Rat Collagen Type I is added to the tube. The tube is reweighed after the addition of collagen. Next, 33 mM acetic acid is added to collagen for a final collagen concentration of 2.7 mg/mL. Then, the mixture is stirred at 4° C. until fully dissolved (2-7 days). The aliquot can be stored at 4° C. until required for use. This can be used directly from stock 2.7 mg/mL solution, or 900 μL aliquots can be created in micro-centrifuge tubes. The stock solution or aliquots can be stored at 4° C. The three-dimensional scaffold structures are the same as those described above in Example 1.

The process for forming the protein bridge mesh on the scaffold structure is like that in Example 1, except DMEM and 0.34 N NaOH are placed on ice. If not aliquotted, 900 μL of the 2.7 mg/mL stock solution is added to micro-centrifuge tube on ice. On ice, 100 μL of DMEM is added. The solution is yellow in color. On ice still, 140 μL of 0.34 N NaOH is added to micro-centrifuge tube. The solution should now turn pink with the addition of base. (DMEM helps to mediate ionic strength of final solution, acts as a pH indicator, and helps achieve a more uniform protein mesh.) The tumbling is conducted for 6 hours at 27° C.

FIGS. 6A-6D show suspended protein bridge meshes in different cell culture scaffolds can be made with a large variety of proteins according to certain aspects of the present disclosure. FIG. 6A shows a left column having fibronectin (FN), laminin (LAM), and collagen (COL) as secreted by human mammary fibroblasts when cultured on tissue culture polystyrene. The middle column of FIG. 6A is FN, LAM, and COL as suspended on 3D jet writing scaffolds. The right column includes SEM images of FN, LAM, and COL fibrils as suspended on 3D jet writing scaffolds shown at 10,000× magnification. This matrix of images demonstrates that suspended protein meshes can be compared to proteins as naturally secreted by cells to form their own matrix when cultured on 2D polystyrene (tissue culture polystyrene plates). FIG. 6B shows a comparative SEM representative image from Flynn, "The use of decellularized adipose tissue to provide an inductive microenvironment for the adipogenic differentiation of human adipose-derived stem cells," Biomaterials 31 (2010) pp. 4715-4724, the relevant portions of which are incorporated herein by reference. FIG. 6B shows decellularized human adipose tissue revealing the fibrous morphology of physiological human tissue. The similarities between the SEM images in FIG. 6A and the extracellular matrix (ECM) shown in FIG. 6B indicates the superior performance of the inventive cellular support systems having suspended protein matrices at mimicking native ECM. FIG. 6C is a zoomed out view showing a larger scale visualization of fibronectin in mixture with tenascin c. This demonstrates capability of cellular support systems having suspended protein bridge meshes to be made of mixtures of proteins. A ratio of fibronectin to tenascin c is 95:5, also illustrating that the ratio of one protein to another can be controlled. FIG. 6D shows a 60× magnified view of both fibronectin and tenascin c (all), fibronectin alone, and tenascin c alone suspended mesh as shown in FIG. 6C.

FIGS. 7A-7C show MCF7 breast cancer cells have an increased ALDH positive population when cultured on cellular support systems having suspended laminin bridge structures in the form of a mesh prepared in accordance with certain aspects of the present disclosure (FIG. 7C). A comparison to a cellular support system having suspended fibronectin bridge structures as a mesh prepared in accordance with other aspects of the present disclosure is shown in FIG. 7B. A DEAB control is shown in FIG. 7A. FIG. 7B shows an increase from 1.48% on fibronectin to 2.34% on laminin in FIG. 7C. This data, among many other studies in the literature show that cells respond differently when exposed to various extracellular matrix compositions. Having a diverse library of proteins that can be used when fabricating suspended protein bridge structures indicates versatility and commercial potential of the inventive technology.

FIG. 8 shows a growth curve for MDA-MB-231 human breast cancer cell line with normalized cell growth versus days after cell seeding. Three different suspended protein meshes are independently analyzed for impact on growth of MDA-MB-231 breast cancer cells: fibronectin only (green), laminin only (red), and fibronectin plus laminin (purple). FIG. 8 thus shows differences in growth depending on the composition of the suspended protein mesh. The combination of the two proteins results in the largest growth, followed by fibronectin, and finally laminin. This demonstrates the superiority of certain aspects of the present technology to allow researchers to control which proteins cultured cells are exposed to, and to elucidate impacts of the composition of the protein microenvironment on cell behavior in a controlled experimental setup.

FIGS. 9A-9G show cellular support systems having suspended fibronectin bridge structures as a mesh prepared in accordance with certain aspects of the present disclosure. FIGS. 9A-9B show LSCM images at 20× magnification with polymer in blue, cell nucleus in pink, and actin in red having HUVECs cultured on either a suspended fibronectin mesh (FIG. 9A) or suspended laminin mesh (FIG. 9B). Neither protein alone was able to support these cells in vitro (hence these images, which are the best areas found, are poor and show little to nothing). Such cellular support systems having suspended fibronectin bridge structures are superior to other competing technologies given the large library of proteins applicable and the significant impact of protein composition on cell behavior. FIG. 9C shows a first LSCM image at 20× of a scaffold having a mesh comprising both laminin and fibronectin that shows HUVEC cells starting to branch out into the center of the scaffold pore (polymer in blue, cell nucleus in pink, actin in red). FIGS. 9D-9G show 60×LSCM images of HUVECS cultured on suspended protein meshes comprising both fibronectin and laminin. In FIGS. 9D-9G, cells are forming branches and even tubular structures. Cells cultured on the combination of fibronectin and laminin are able to proliferate, and thrive, forming 3D structures around the suspended protein.

FIG. 10 shows an impact of protein composition on cell behavior. Suspended protein supports provide a means for researchers to probe the effect of different ECM composition in a controlled experiment. MDA-MB-231 breast cancer cells, cultured on a suspended fibronectin support of a cell culture system prepared in accordance with certain aspects of the present disclosure, remodeled the proteinaceous environment and migrated off the scaffold into solution after seven days. This phenomenon can be applied as a model of cancer metastasis as discuss further below. Suspended collagen supports on the other hand, are not remodeled, and cells did not migrate off the scaffold. Instead, with collagen, cells stay within the microenvironment. The trends with which these cells expand also differ based on the identity of the protein used to form suspended protein supports (i.e., composition). Note that different proteins can be combined to form suspended protein supports of more than one protein making the principles and cellular support systems of the present teachings a powerful tool.

FIGS. 11A-11E show the superior nature of a suspended protein bridge mesh on a three-dimensional scaffold structure prepared in accordance with the present disclosure, which yields unique protein morphologies and high densities of protein loading. FIG. 11A shows SEM images illustrating comparison of static incubation and dynamic incubation conditions. The left (i) and middle (ii) SEM images show tissue culture on polystyrene coated with the same concentration of protein, at the same temperature, for the same amount of time under both static and dynamic incubation conditions as compared to the right SEM image of FIG. 11B having a suspended protein bridge mesh on a three-dimensional scaffold structure prepared in accordance with certain aspects of the present disclosure having dynamic incubation conditions. In FIG. 11A, fibronectin is conformally coated onto tissue culture polystyrene (TCPS) via (i) static adsorption in contrast to (ii) shear-driven synthetic deposition of fibronectin onto TCPS using the same method as when producing cFN-scaffolds. The suspended protein bridge mesh clearly yields a matrix with superior mimicry of the physiological extracellular matrix. FIG. 11B is a cFN-scaffold after shear-driven deposition of fibronectin onto a microfiber scaffold.

Cellular fibronectin (cFN) is found in many isoforms, each exposing the mechano-sensitive FNIII domain, which is key to fibrillogenesis and matrix assembly. cFN is assembled by cells that bind to the protein through integrin-based structures. Translocation of these integrins on the cell surface imparts tension that unfolds FNIII domains, exposing self-association binding sites that allow interactions between fibronectin molecules leading to cFN fibrillogenesis.

Use of cFN-scaffolds can be extended a variety of tissue types including endothelial cells, human mesenchymal stem cells, induced pluripotent stem cells, human embryonic stem cells, Ewing sarcoma cells, pancreatic and prostate cancer cells, by way of non-limiting example. Such versatility is made feasible by modeling the microenvironment as described in the present teachings, where synthetic material may constitute less than 4% of the overall scaffold volume. The large open area allows cells to customize the ECM, such as with laminin secretions from MDA-MB-468s, and form more complex multicellular cell-cell and cell-protein constructs. cFN-scaffolds prepared in accordance with certain aspects of the present disclosure can successfully model EMT in vitro which is highly desirable to understand therapeutic effects since EMT is directly related to drug resistance and a resistance to apoptosis.

FIGS. 11C and 11D shows charts of mass of fibronectin loaded onto a polymer support scaffold (μg) for a comparative conformal protein coating on a scaffold (Conformal fibronectin (FN)) and a suspended protein bridge mesh on a three-dimensional scaffold structure prepared in accordance with the present disclosure (cFN-scaffold). FIG. 11C shows mass of conformal fibronectin (cFN) synthetically deposited onto microfiber scaffold after 15, 30, 60, 120 and 240 minutes of incubation at the fluid interface under shear flow. Stars indicate no statistical difference between the 120 and 240 minute time points. FIG. 11D show mass of fibronectin loaded onto a microfiber scaffold as a function of scaffold pore size after either shear-driven synthetic deposition (cFN-scaffolds, white bars) or conformal coating via static adsorption (grey bars). Stars indicate no statistical difference amongst the protein masses measured from scaffolds of three different pore sizes, while stars also indicate that all shear-driven synthetic deposition (white bars) is statistically different from the conformal coatings (grey bars). FIGS. 11C and 11D shows good agreement with SEM images in FIG. 11B, where microBCA analysis shows that suspended protein meshes achieve high density protein loads. Suspended protein meshes offer significantly higher protein loading when compared to conformal coatings on porous scaffolds irrespective of scaffold pore size. FIG. 11E shows SEM contrasting loading of fibronectin (left) synthetically deposited and (right) conformally coated onto polymer microfiber scaffolds.

FIG. 12A-12B show comparison of a human breast cancer cell line MDA-MB-231s cultured on tissue culture polystyrene (TCPS) versus a suspended fibronectin protein bridge mesh on a three-dimensional scaffold structure prepared in accordance with certain aspects of the present disclosure, which remodels protein and moves off suspended fibronectin bridge mesh. FIG. 12A (left) shows MDA-MB-231 (231s) human breast cancer cell line cultured on tissue culture polystyrene (TCPS). The cell nucleus is in purple, actin is in green. Laser scanning confocal microscope (LSCM) image at 60× magnification. FIG. 12A (right) shows MDA-MB-231 human breast cancer cells cultured and imaged on suspended fibronectin mesh scaffolds at 60× magnification on LSCM. Suspended fibronectin bridge meshes allow a higher degree of cell-cell contacts in 3D space to form a thriving tissue in vitro compared to the same cells cultured on TCPS for the same amount of time. Cells cultured on TCPS have a more artificial flattened morphology and make fewer cell-cell contacts. Furthermore, cells on TCPS do not perform protein matrix remodeling as cells cultured on suspended protein supports do.

In the in vivo cell delivery application shown in FIG. 13, implanting suspended fibronectin meshes with pre-established cell-cell and cell-ECM contacts in vitro is advantageous compared to injection of freely floating cells removed from TCPS. FIG. 12B (left) shows 231s after 5 days of culture form a confluent volume of tissue on the suspended fibronectin mesh cell culture scaffold. FIG. 12B (right) shows that after 9 days of culture on suspended fibronectin mesh 231s are no longer tethered to the protein but rather move off into solution. Subsequent experiments show that these cells are still 98% viable in solution. At 9 days, the original protein mesh is no longer visible indicating that the cells have broken down or remodeled the proteinaceous environment as they move off into solution. This behavior parallels an Epithelial to Mesenchymal Transition (EMT). Note that having the supporting scaffold, in addition to the protein mesh, allows cells to entirely break down the protein, while still having the scaffold as a skeletal structural support, for example, the 9 day MDA-MB-231s. Other technologies which are made entirely of protein would not remain mechanically stable in the case of modeling cancer metastasis where cells break down the protein matrix.

FIG. 14 shows that a suspended protein bridge mesh on a three-dimensional scaffold structure prepared in accordance with the present disclosure can be applied as an in vitro model for cancer metastasis. FIG. 14 shows time after seeding (days) versus normalized expansion (I/IO). As seen in FIGS. 12A-12B, MDA-MB-231 human breast cancer cells form confluent volumes at first, but eventually migrate off the suspended protein mesh. In parallel, bioluminescence is used to produce the growth curve on the left. Initially, cells are rapidly proliferating in a "growth phase." At day 7, the cells reach a peak population, then enter a "remodeling phase" where they leave the suspended protein mesh, and remain viable in solution. A subsequent study shows that cells in solution are still 98% viable and can be collected for re-seeding onto a new suspended protein mesh. This indicates that the cells are not simply dying and falling off the mesh, but rather selecting to "migrate off" as they would in metastasis.

FIG. 15 shows percent invasion for cells that are cultured in parallel on either a tissue culture polystyrene (TCPS) support, or on suspended fibronectin bridge meshes on a three-dimensional scaffold structure prepared in accordance with certain aspects of the present disclosure. To validate that the suspended protein mesh does indeed serve as a metastatic model, during the remodeling phase, cells that migrated off the meshes are collected from solution for this assay. Cells taken off the TCPS are used for comparison. A modified Boyden chamber with an 8 μm pore scaffold is coated with 300 μg/ml Matrigel for 2 h at 37° C. Both groups of cells are serum starved for three hours. 25,000 cells are placed in the upper chamber. 10% FBS is placed in the lower chamber to induce invasion. A significant increase in the invasive potential of the cells is observed using cells that migrated off of the scaffolds as shown in the graph.

FIG. 16 shows $\Delta C_T$ from GAPDH for MDA-MB-231 human breast cancer cells cultured on suspended fibronectin protein meshes prepared in accordance with certain aspects of the present disclosure for nine days. After 1 day, 5 days, and 9 days, the cells are analyzed for expression of E-cadherin (indicative of a proliferative state), and MMP2 (indicative of protein break down, extracellular matrix remodeling, and migratory behavior). In agreement with the growth curve in FIG. 14, MMP2 upregulation appears at day 9 when cells are indeed migrating off the suspended protein mesh as well as breaking down or remodeling the original protein mesh as it was fabricated.

FIG. 17A shows cell number counts at 0 days and 7 days for breast cancer patient cells on conventional tissue culture polystyrene (TCPS) versus a suspended protein bridge mesh on a three-dimensional scaffold structure prepared in accordance with the present disclosure (labelled as scaffold). The cells show little to no proliferation on tissue culture polystyrene (TCPS) compared to a suspended protein bridge mesh on a three-dimensional scaffold structure prepared in accordance with the present disclosure (labeled as scaffold) after 7 days. Ki67 is a cell marker that indicates whether the cell is in a proliferative state. For the scaffold, Ki67 is positive as shown by the dark colored cell stain. On conventional TCPS, the stain appears lighter purple in color indicating that these cells are negative for Ki67 and therefore not in a proliferative state. FIGS. 17B-17I will be discussed further below.

FIG. 18A shows a schematic for seeding human mesenchymal stem cells on a PLGA fiber scaffolds having with fibronectin bridges that led to confluent volumes of cells over the course of 3-5 days. Once confluency is achieved, the cells differentiate towards an osteogenic lineage for four weeks. After four weeks, the two scaffolds laden with differentiated cells are implanted into the back of a NOD SCID mouse. On the opposite side of the back, two scaffolds containing only the fibronectin protein coating are implanted. The implants are allowed to incorporate into the mouse for two weeks before an intracardiac injection of bioluminescent cancer cells (MDA-MB-231 Luc) is performed. FIGS. 18B-18C show three weeks post-injection, the mice are injected with luciferin, and scanned in a bioluminescent scanner. Presence of bioluminescent signal near the implantation site indicates the cancer cells had metastasized to the osteogenically differentiated scaffold. Explantation of the implants reveals that bioluminescent samples are located on the side containing osteogenically differentiated cells, while the control scaffolds containing only the protein coating are not bioluminescent (had no cancer cells). FIG. 18D shows that implantation of osteogenically differentiated cells on both sides of the mouse led to bioluminescent signal in both implants. This demonstrates that metastasis can occur on both sides of the mouse simultaneously.

FIGS. 19A-19C show three-dimensional growth of human mesenchymal stem cells on a conformal fibronectin-coated glass (FIG. 19A), a conformally fibronectin coated PLGA non-woven scaffold (FIG. 19B), and a suspended insoluble protein bridge mesh on a three-dimensional scaffold structure prepared in accordance with the present disclosure (FIG. 19C). Without the three dimensional protein space provided by the suspended protein support in FIG. 19C, the growth of cultured cells is strongly limited in the z-direction, as shown in FIGS. 19A-19B. Suspended proteins supports lead to 3D cell structures more like a tissue, rather than a mono- or bi-layer of cells on a surface.

Example 5

This example is another where cellular fibronectin (cFN) is deposited onto microfiber scaffolds to form a cell support system having a three-dimensional scaffold structure with void regions having a suspended fibronectin bridge. Where not otherwise indicated, the same techniques and components as those listed in the previous examples are used.

With the targeted goal of mimicking a native-like fibronectin matrix in vitro, a large-scale, freely suspended networks of cFN is formed in a cell-free manner. Induction of fibrillogenesis via the sheet-to-fiber transition requires a shear force at the interface of two phases during the formation process: namely an interface between air and a fibronectin solution as shown in FIG. 21A. A porous support at the interface serves as a nucleation site for fibrillogenesis, and on which the cFN network can be suspended such that the interaction of the protein with any synthetic surface is minimized. Poly(lactide-co-glycolide) (PLGA) microfiber scaffolds fabricated by 3D jet writing are selected as a support for the free-standing suspension of cFN networks because they have approximately 4% material by volume, while maintaining structural integrity as shown in FIG. 21B.

Briefly, in the 3D jet writing process to form the scaffold, fibers ranging from about 8 micrometers to about 12 micrometers in diameter are patterned into a computer controlled geometry and stacked to achieve a third dimension. Scaffold size and geometry are tunable, but all scaffolds reported here are 5.8 mm by 6 mm, made by stacks of ten fibers, patterned into a grid array of square pores 500 μm wide unless otherwise noted. Each pore offers large open areas that can contain upwards of 35,000 cells, allowing cells to secrete their own ECM, migrate, and form multicellular structures, while limiting interference from synthetic material on cell behavior and protein conformation.

To synthetically create cFN networks, the PLGA microfiber scaffold is secured at the air-solution interface as shown in FIG. 21A. By shearing the interface over the scaffold, insoluble fibronectin fibrils are drawn out from the sheet of globular fibronectin that forms at the fluid interface. A time course depicting cFN loading onto the scaffold after 15, 30, 60, and 120 minutes of contact time at the fluid interface under shear during incubation is shown in FIG. 21C. The mass of protein loaded onto the scaffold increases with time under shear flow until 120 minutes, after which no significant increase in protein mass is observed. Fibronectin loading onto the scaffold is significantly higher when exposed to shear flow at the two-phase interface relative to a conformal protein coating, irrespective of scaffold pore size. Through a sheet-to-fiber transition, fibronectin fibrils (FIG. 21D) suspend across and within scaffold pores at large scale as shown in FIG. 21F, forming a cFN-scaffold. As a control, tissue culture polystyrene (TCPS) is either treated with the same fluid shear procedure or statically incubated in fibronectin solution, both resulting only in the adsorption of a conformal protein coating rather than textured fibrils as formed on cFN-scaffolds.

To validate that the morphology of fibronectin on cFN-scaffolds compares with that of cell-secreted fibronectin, human mammary fibroblasts are cultured on glass substrates to confluency. The substrates are subsequently decellularized, and in parallel with a cFN-scaffold, stained for human fibronectin as shown in FIG. 21E, where (i) shows the cFN-scaffold and (ii) shows the glass substrate.

Next, the fibronectin-3 (FNIII) domain is positively stained as a direct indication that the synthetically deposited protein is indeed in cellular form. In vivo, cFN is found in many isoforms, each exposing the mechano-sensitive FNIII domain, which is important for fibrillogenesis and matrix assembly. cFN is assembled by cells that bind to the protein through integrin-based structures. Translocation of these integrins on the cell surface imparts tension that unfolds FNIII domains, much like the shear force applied in forming cFN-scaffolds. The unfolded FNIII domains expose self-association binding sites that allow interactions between fibronectin molecules leading to an interconnected cFN matrix. FNIII stained positively is found on cFN-scaffolds as well as on the decellularized human mammary fibroblast matrix as shown in FIGS. 21F, 22A-22C, and 23A-23B. In FIGS. 22A-22C, the FNIII domain is exposed across cFN-scaffold at large scale split channel view of FIG. 21F at (i) details the extent of exposure of the FNIII domain across the open pores and at large scale throughout the cFN-scaffold. FIG. 21F at (ii) shows higher magnification views of $FN_{all}$, FNIII, and a merged view of $FN_{all}$ and FNIII. FIGS. 23A-23D show comparison of shear-driven synthetic deposition prepared in accordance with certain aspects of the present disclosure uniquely extends fibronectin into a cellular form (FIG. 23A), showing fibronectin (green) as secreted by human mammary fibroblasts cultured on glass and subsequently decellularized showing exposure of FNIII domains (purple). FIGS. 23B-23D show merged overlays of channels (in the left columns), fibronectin (green, center columns), and FNIII domain (purple, right columns) for plasma fibronectin on cFN-scaffold prepared in accordance with certain aspects of the present disclosure (FIG. 23B) and for comparison, conformally coated onto microfiber scaffold (FIG. 23C), and conformally coated onto glass via static adsorption (FIG. 23D). All images taken at the same laser power and imaging settings via LSCM. Strong overlap of fibronectin (green) and FNIII (purple) appear white in the merged overlay image (left images in FIGS. 23A-23B), but this is not observed in FIGS. 23C-23D. Thus, little to no FNIII signal is observed on glass or microfiber scaffolds that are conformally coated with fibronectin via static adsorption, indicating that conformal coatings lack exposed FNIII domains and the associated biological activity.

As a final validation that cFN-scaffolds serve as an in vitro environment for 3D cell culture, NIH-3T3-fibroblasts are grown for three days on either cFN-scaffolds or conformally coated fibronectin scaffolds. FIG. 21G contrasts the fibroblasts on the conformal coating ((ii) on the right side) formed by static adsorption to the tissue element that formed on the cFN-scaffold formed in accordance with certain aspects of the present disclosure ((i) on the left side). Suspended fibronectin enables the cells to bridge across scaffold pores and rapidly fill the entire volume of the cFN-scaffold at a high cell density, promoting cell-cell and cell-ECM interactions while minimizing contact with the synthetic material. On the other hand, cells simply adhere to the microfiber surfaces when the scaffold is conformally coated (FIG. 21G). FIG. 21G insets also show representative images of the cFN-scaffold and conformally coated scaffold prior to cell seeding. This technique applies not only to fibronectin, but also to other proteins, such as laminin and collagen I (two other common ECM components) by way of non-limiting example.

Example 6

This example explores improvement on tumor engraftment efficiency of three-dimensional tissue cFN-scaffolds formed in accordance with certain aspects of the present disclosure. Where not otherwise indicated, the same techniques and components as those listed in the previous examples are used.

Since fibronectin is a major ECM protein of the pre-metastatic niche and has been co-localized with micro-metastasis, the potential of cFN-scaffolds prepared in accordance with certain aspects of the present disclosure to induce phenotypic changes in breast cancer cells is investigated. Patient derived xenografts (PDXs) provide a more physiologically relevant platform for drug screening and prognoses, and open an avenue for more personalized cancer therapies. Unfortunately, breast cancer PDXs, currently formed by implanting patient cells into a mouse mammary fat pad and awaiting tumor formation, suffer from low tumor take rates and those that do form are typically limited to the most aggressive cancers. The potential for cFN-scaffolds to improve engraftment efficiency in a mouse breast cancer tumor graft assay is tested. AT-3 firefly luciferase expressing mammary cancer cells, a cell line derived from the primary mammary gland tumor of MMTV-PyMT mice, are cultured on cFN-scaffolds. After three days, the AT-3s form a dense, interconnected network of cell-cell contacts on the cFN-scaffolds (FIG. 24A) at large scale (FIG. 24B) and are still in a proliferative phase.

Three-millimeter-wide disks carrying AT-3 cells are then punched out from a scaffold and orthotopically implanted into three immunocompetent C57BL/6 mice. Previous studies have concluded that a minimum of 200,000 AT-3 cells are required for tumor formation by injection. Due to consistency of tumor inoculation with a minimum dose of 200,000 cells by direct injection, the first of three mice serves as a positive control receiving a cFN-scaffold with approximately 200,000 cells in one mammary fat pad, and an injection of 200,000 cells in the contralateral fat pad. The remaining two mice receive approximately 30,000 cells via injection into one mammary fat pad, and an implanted cFN-scaffold carrying approximately 30,000 cells into the contralateral fat pad. The number of AT-3 cells carried by each cFN-scaffold is verified by luciferin prior to implantation (data not shown). Bioluminescence readings after two days indicate that the cFN-scaffold implants carrying only 30,000 cells had resulted in the start of tumor formation, whereas no signal was detected at the injection site. This result remains consistent for the 21-day duration of the study as shown in FIG. 24E, where a bioluminescence image of immune-competent mice showing tumor formation 21 days after AT-3 cells are orthotopically implanted (image exposure time 10 seconds). The two mice on the left have had cFN-scaffolds carrying about 30,000 AT-3 cells implanted into the mammary fat pads indicated by arrows. The right mammary fat pad received an injection of approximately the same number of cells in the area indicated by circles. The third mouse on the right is a positive control having received a cFN-scaffold in the left mammary fat pad (arrow), and an injection in the mammary fat pad on the right, each delivering 200,000 AT-3 cells. Follow up histological analyses of the tumor grafts resulting from the cFN-scaffold implant of 30,000 cells show the AT-3s invading into neighboring tissue in FIG. 24F.

Intrigued by this invasiveness, and in search of a mechanistic explanation of the improved engraftment efficiency, the population of tumor-initiating cells amongst AT-3s cultured three days on TCPS, fibronectin conformally coated onto TCPS (FN on TCPS), or cFN-scaffolds is quantified, as shown in FIGS. 24C and 24D. Murine breast cancer cells that are positive for the surface markers CD29 (Beta-1 integrin) and CD24 (Heat shock protein) retain their capacity for self-renewal and have the capacity to initiate a tumor. Additionally, the $CD24^+/CD90^+$ population has been identified to be the metastatic subpopulation of TICs. No statistical differences are observed in the population of $CD24^+/CD29^+$ cells cultured on TCPS or FN on TCPS. However, a significant increase in the CD24$^+$/CD29$^+$ population of AT-3 cells is observed when cultured on cFN-scaffolds (P<0.05). The vast majority of the AT-3 cells are positive for CD29, regardless of the culture substrate, indicating that observed differences in the TIC population are the result of differences in CD24 expression. No significant difference in the CD90$^+$ population is observed for cells cultured on TCPS or FN on TCPS, however an almost 30-fold increase is observed for cells cultured in cFN-scaffolds (P<0.05) (FIG. 24D). Within the different culture environments, no significant differences are observed between the CD24$^+$/CD29$^+$ and CD24$^+$/CD90$^+$ populations. However, a significantly greater population of CD24$^+$/CD90$^+$ cells is observed in cFN-scaffolds than on TCPS or FN on TCPS. A significantly greater percentage of cells are CD24$^+$/CD29$^+$/CD90$^+$ on cFN-scaffolds than on TCPS or FN on TCPS as shown in FIG. 24C. Overall, AT-3s cultured on cFN-scaffolds show a significant enrichment of tumor-initiating cells relative to the control substrates.

This is further corroborated by the enhanced tumorigenicity in the mouse tumor engraftment study. The flow cytometry results demonstrate that conformally coating fibronectin onto TCPS does not result in the same biological functionality as fibronectin fibrils freely suspended across cFN-scaffolds.

Example 7

This example explores enrichment of tumor-initiating cell population in human breast cancer cells on cFN-scaffolds formed in accordance with certain aspects of the present disclosure. Where not otherwise indicated, the same techniques and components as those listed in the previous examples are used.

The increased tumorigenicity observed in the AT-3 mouse breast cancer cell line is also phenotypically seen in the triple negative human breast cancer cell line, MDA-MB-468. FIG. 25A shows a representative section of the confluent MDA-MB-468 tissue element on a cFN-scaffold after four days of culture. FIG. 25B demonstrates the scalability of the cFN-scaffolds with a lower magnification view. Having a small percentage of cells that express the mesenchymal CD44$^+$/CD24$^-$ tumor initiating phenotype (less than 3%), MDA-MB-468s are selected as a model human cell line to clearly distinguish any enrichment of the tumor initiating population due to culture on cFN-scaffolds. In addition to the CD44$^+$/CD24$^-$ cells which are a migratory mesenchymal phenotype, the epithelial-like tumor-initiating cells by aldehyde dehydrogenase (ALDH) expression are quantified. ALDH is a known marker of both mammary stem cells and the proliferative behavior needed for tumor formation, and has been considered a superior indicator of tumor-initiating cells relative to CD44$^+$/CD24$^-$. MDA-MB-468s are also cultured on TCPS, and TCPS coated conformally with fibronectin (FN on TCPS). Cells from the three substrates are analyzed over time for the percent of the population that is CD44$^+$/CD24$^-$ as shown in FIG. 25C, ALDH$^+$, and the overlapping immunotype, CD44$^+$/CD24$^-$/ALDH$^+$ (FIG. 25D), which has been described by Ginestier, et al., "ALDH1 Is a Marker of Normal and Malignant Human Mammary Stem Cells and a Predictor of Poor Clinical Outcome," Cell Stem Cell 1, pp. 555-557 (2007), the relevant portions of which are incorporated herein by reference, as being most tumorigenic when forming PDXs. At each time point, the CD44$^+$/CD24$^-$ and CD44$^+$/CD24$^-$/ALDH$^+$ populations are present at a higher percentage on cFN-scaffolds than TCPS or FN on TCPS with a significant enrichment by the sixth day in culture as shown in FIGS. 25C and 25D. Initially after seeding, a significantly greater ALDH population is observed in MDA-MB-468s cultured on cFN-scaffolds relative to TCPS and FN on TCPS, but after four days in culture, all three substrates show no difference in the percentage of cells expressing ALDH. Furthermore, no statistical changes are observed within the population expressing the epithelial cell adhesion molecule (EpCAM$^+$) being greater than 99% regardless of the culture substrate. This enrichment of the mesenchymal tumor initiating cells on cFN-scaffolds is not due to proliferation trends since the three substrates yield similar growth curves. This proliferation behavior is not unusual as it is also seen with T47D and Sum159 human breast cancer cell lines. Altogether, these data suggest that the cFN-scaffolds prepared in accordance with certain aspects of the present disclosure are inducing EMT in the MDA-MB-468 cells.

Stem-like breast cancer cells build laminin into their ECM for support of self-renewal and tumorigenicity per Chang et al., "A laminin 511 matrix is regulated by TAZ and functions as the ligand for the alpha6Bbeta1 integrin to sustain breast cancer stem cells," Molecular, Cell and Cancer Biology Publications 22 (2015), the relevant portions of which are incorporated herein by reference. Here, the experiment detects if the enrichments in the CD44$^+$/CD24$^-$ and CD44$^+$/CD24$^-$/ALDH$^+$ populations are correlated with laminin secretion. MDA-MB-468 cells are cultured four days on cFN-scaffolds; the scaffolds are subsequently decellularized, and both the synthetically deposited cFN as well as the cell secreted laminin are stained. The decellularized cFN-scaffolds reveal that the MDA-MB-468s secreted small and sporadic amounts of laminin and left the cFN matrix intact.

Example 8

This example pertains to cFN-scaffolds used to support expansion of patient-derived cells and induce an epithelial to mesenchymal transition (EMT) of cells. Where not otherwise indicated, the same techniques and components as those listed in the previous examples are used.

Upon observing trends in both mouse and human breast cancer cell lines towards a tumor-forming phenotype, the capability of cFN-scaffolds prepared in accordance with certain aspects of the present disclosure is tested to form patient specific tumor grafts in vitro without the use of animal models. Patient cells are obtained from malignant pleural effusions or ascites from women with metastatic breast cancer and a seeding density was determined for primary cell culture on cFN-scaffolds. 14 out of 14 patient samples are successfully cultured on cFN-scaffolds without prior fractionation, as shown in Table 1.

TABLE 1

Breast cancer patient data

| Patient* | Sample type** | Patient age | Receptor status*** | | | Detected metastases |
|---|---|---|---|---|---|---|
| | | | ER | PR | HER2 | |
| A - IDC | AC | 47 | − | − | − | Lymph node, Bone |
| B - ILC | AC | 76 | + | + | − | Peritoneum, Bone |
| C - ILC | AC | 54 | + | + | + | Peritoneum, Bone |
| D - —   | AC | 73 | — | — | — | Renal, Omental, Peritoneum |
| E - IDC | AC | 61 | + | + | − | Endometrial, Uterine cancer |
| F - IDC | AC | 51 | − | − | + | Chest wall, Skin, Left axilla, Lymph node |

TABLE 1-continued

Breast cancer patient data

| Patient* | Sample type** | Patient age | Receptor status*** | | | Detected metastases |
|---|---|---|---|---|---|---|
| | | | ER | PR | HER2 | |
| G - IDC | PE | 51 | + | + | + | Skin, Pleura, Bone |
| H - IBC | PE | 44 | − | − | + | Pleura |
| I - IBC | PE | 53 | + | + | − | Chest wall, Ovaries, Bone |
| J - IDC, ILC | PE | 57 | + | − | − | Liver, Bone |
| K - IDC | PE | 56 | + | + | − | Skin, Liver, Lung, Pleura, Lymph node |
| L - IDC | PE | 42 | + | + | − | Leptomeningeal, Eye, Bone |
| M - IDC | PE | 40 | − | − | + | Lymph node |
| N - — | PE | 62 | — | — | — | Bone |

*Patient: Patient sample as arbitrary letter name followed by cancer type. Invasive ductal carcinoma (IDC), invasive lobular carcinoma (ILC), inflammatory breast cancer (IBC)
**Sample type: ascites (AC), pleural effusion (PE)
***Receptor status: estrogen receptor (ER), progesterone receptor (PR), human epidermal growth factor receptor 2 (HER2)

8 out of 12 (2 patients had unknown receptor status) were estrogen receptor positive, a breast cancer subtype that is significantly less likely to form a PDX. All 14 patient samples thrived and proliferated on cFN-scaffolds, but not on comparative TCPS or FN on TCPS, as represented in FIG. 17D. Ki67 staining further indicated that the cells are in a proliferative state on cFN-scaffolds but senescent on TCPS (FIG. 17D). Interestingly, Patient E cells that are first cultured on cFN-scaffolds for one day, removed and re-seeded onto TCPS, successfully proliferated on TCPS thereafter, as shown in FIG. 26A. Throughout this proliferative state on cFN-scaffolds, heterogeneous cell populations are maintained with respect to cell morphology or cytokeratin 5 (CK5) expression (FIG. 17B). Cytokeratin 5 (CK5) is used to identify the cancer cells within the mixed population. Interestingly, the cancer cell population, denoted by lineage negative cells, increases relative to the original patient sample after culture on cFN-scaffolds. This shift is also observable by microscopy as with the ascites sample from Patient C (patient samples arbitrarily named), where after five days of culture, the CK5-rich cells remain in clusters just off of the microfiber crosshairs of the cFN-scaffold while the actin-rich cells adhere to the to the scaffold. By the tenth day of this culture however, the CK5-expressing cancer cells had increased in population and formed a cell network spreading out into the open areas of the cFN-scaffold. To some extent, cFN-scaffold culture is inherently selective as some extraneous cell types such as platelets and blood cells had not adhered to the cFN-scaffold but instead are removed after the first media changes. Cells from certain patient samples are found to spatially separate on cFN-scaffolds such as with Patient K, where CK5-rich cells formed clusters in one area while actin-rich cells of a more spindle-like morphology adhere first to the microfibers of the scaffold and proliferate outwards. Importantly, the patient cells are able to be expanded at large scale on cFN-scaffolds. FIG. 17C depicts how Patient B cells are able to proliferate and fill all open areas of the cFN-scaffold after only three days in culture.

Figure 17F:
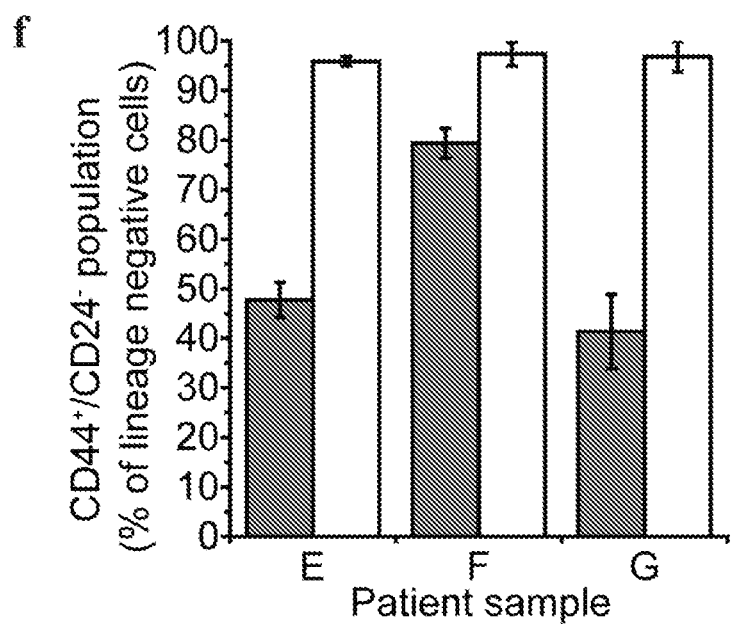
Figure 17G:
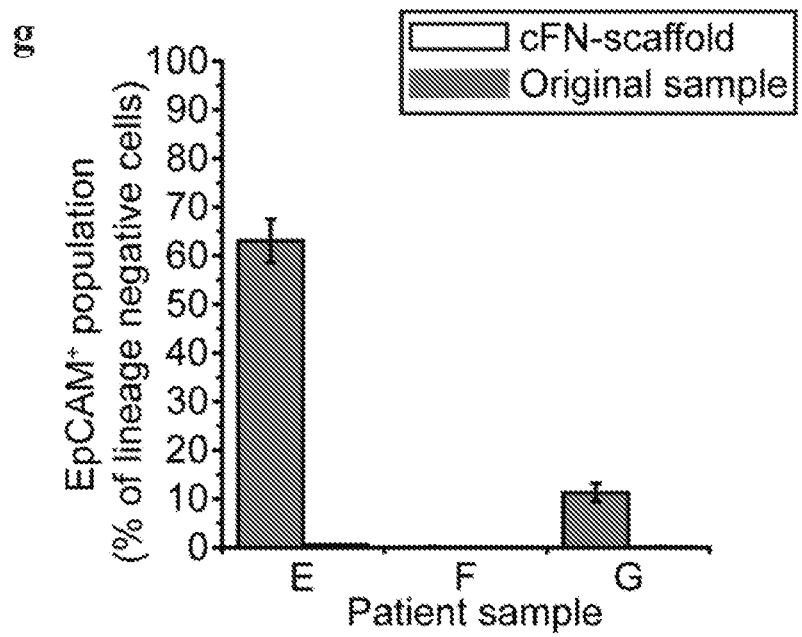
Figure 17H:
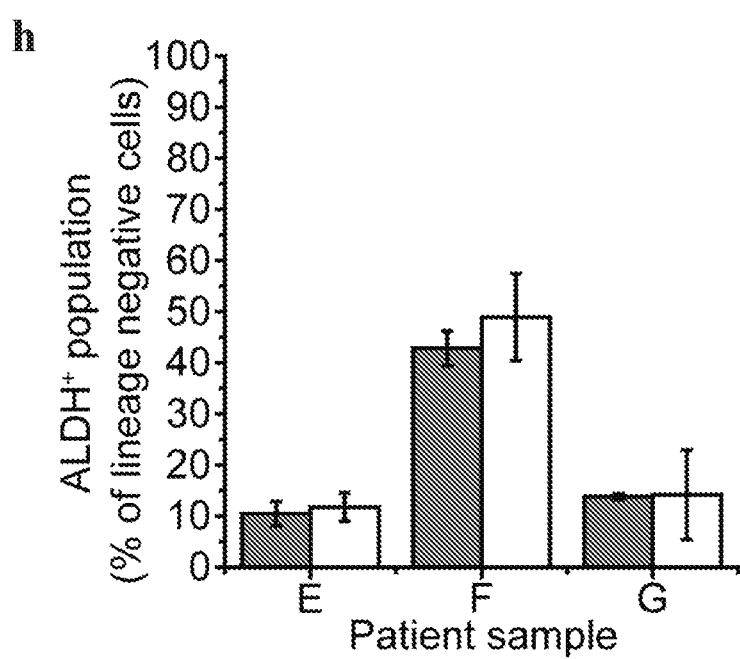
Figure 17I:
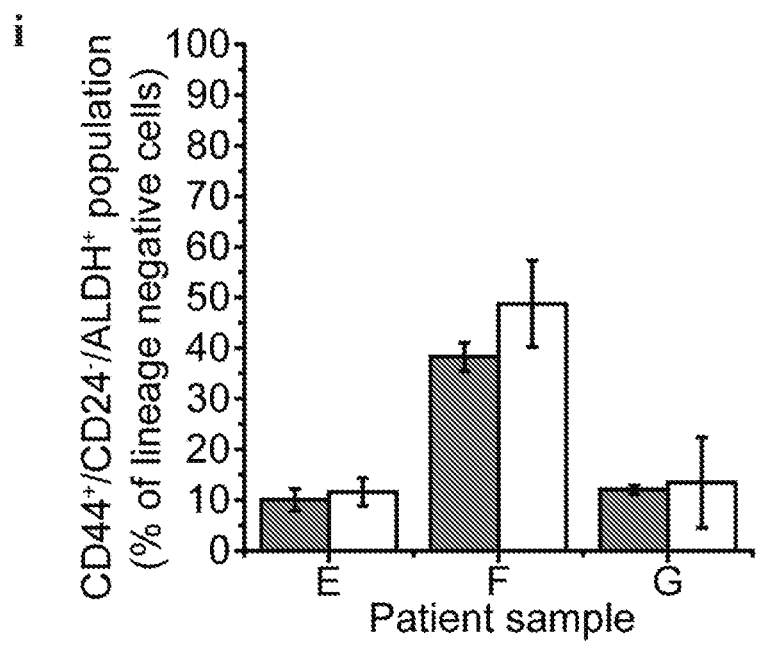

Within the cancer cell population (marked by lineage negative cells), culture on cFN-scaffolds prepared in accordance with certain aspects of the present disclosure enriches the mesenchymal stem-like CD44$^+$/CD24$^-$ subpopulation as compared to the original patient sample (FIGS. 17E-17F). At the same time, the epithelial-like tumor-initiating subpopulations indicated by ALDH$^+$ (FIG. 17H), and the overlapping immunotype CD44$^+$/CD24$^-$/ALDH$^+$ (FIG. 17I) are maintained on cFN-scaffolds. This implies that most of the ALDH$^+$ cells in the original patient samples are also CD44$^+$/CD24$^-$. For comparison, cells from Patient E are plated directly onto TCPS. The cells struggled to proliferate (FIG. 26B), but grew sufficiently to detect the ALDH$^+$ population. The percentage of ALDH$^+$ cells from the original patient sample is maintained on cFN-scaffolds, but drops significantly on TCPS. When present in the original patient sample, the percentage of cancer cells expressing the epithelial cell adhesion molecule (EpCAM) dropped to nearly zero after culture on cFN-scaffolds (FIG. 17G). Despite these shifts in cell phenotype, the breast cancer receptor status of the original sample is maintained on cFN-scaffolds (n=1) as shown in FIG. 27. Together, these results suggest that cFN-scaffolds induce an epithelial to mesenchymal transition (EMT) in patient derived breast cancer cells.

As research shifts away from 2D monolayer cultures, it is believed that three dimensional tissue scaffolds having one or more suspended protein bridges spanning one or more voids, like cFN-scaffolds, can address the current need for a new standard 3D cell culture system. Such three-dimensional tissue scaffolds, like cFN-scaffolds, are a biophysically and biochemically relevant 3D cell microenvironment for maintenance of both immortalized and primary cells in vitro, and can serve as an implantable tissue engineering scaffold as shown in the AT-3 tumor graft assay.

A desirable culture system offers an ability to independently investigate the effects of ECM composition and how cells are remodeling the ECM, while preserving the biological activity of proteins; at the same time it can be easily handled, and remain amenable to standard culture and characterization techniques.

Without limiting the present disclosure to any particular teachings, it is hypothesized that in vitro formation of 3D cell-protein structures prior to implantation, as in the AT-3 mouse tumor graft study, enables three-dimensional tissue scaffolds, like cFN-scaffolds, prepared in accordance with certain aspects of the present disclosure to serve as an effective cell delivery vehicle. Enhanced cell survival and engraftment upon implantation is thus expected, because the cells have pre-formed a thriving tissue element, in contrast to injection of freely floating cells. The improved AT-3 engraftment efficiency is hypothesized to be due to the presence of the ECM that improves localization of cells within the region.

AT-3 tumor engraftment efficiency is improved in parallel with the observed enrichment of the tumor-initiating population in the cFN-scaffolds (FIGS. 24A-24F), particularly the metastatic CD90$^+$/CD24$^+$ population. Notably, three mice were immunocompetent in the AT-3 tumor engraftment study. There is evidence supporting a role for the immune system in promoting tumor growth and progression. Minimizing contact between proteins and synthetic surfaces also maximizes the likelihood that the deposited protein remains in a native, biologically active conformation. At the same time, a scaffold, such as a PLGA microfiber scaffold, provides structural support for the protein matrix. Furthermore, in light of the reversibility of fibronectin extension and FNIII domain unfolding, the microfiber scaffold also aids in securing the fibronectin fibrils in an extended form while keeping the bulk of the protein free standing.

The suspended protein bridges are not limited to fibronectin alone, but include various other proteins, like collagen, laminin, and with minor protocol variations, also include other ECM proteins as well. This provides the ability to tune the composition of the protein microenvironment, either by addition of individual proteins, or combinations of proteins in controlled ratios.

Fibronectin is a known pre-metastatic niche protein and a mesenchymal marker and its expression has been shown to be upregulated in primary human breast cancer cells of the $CD44^+/CD24^-$ phenotype. When cultured on cFN-scaffolds prepared in accordance with certain aspects of the present disclosure for five days, primary human breast cancer cells from pleural effusions or ascites show a distinct upregulation of the mesenchymal stem cell phenotype, $CD44^+/CD24^-$, which coincides with a downregulation of EpCAM, and maintenance of the ALDH population compared to the original sample. CD24 and CD44 have been shown to play a role in vitro in cell anchorage to several ECM proteins, including fibronectin, either directly or indirectly through integrin activation. Cell signaling through binding to specific ECM proteins reiterates the importance of maintaining large proteins in a conformation that resembles cell-secreted matrix, complete with exposure of critical binding sites on the protein. These results characterize an epithelial to mesenchymal transition, and suggest that cFN-scaffolds may serve as a model to study EMT, which is thought to be the underlying mechanism of metastasis.

Going forward, cFN-scaffolds prepared in accordance with certain aspects of the present disclosure may be used to unravel current uncertainties regarding the roles of CD44, CD24, and ALDH in EMT, and the search for additional markers of the tumor-initiating phenotype. Therapeutic targeting of these cells will largely benefit from a reliable set of identifying characteristics. At a fundamental level, cFN-scaffolds can also inform the bidirectional relationship between cancer cells and the microenvironment as it relates to tumor progression.

In certain aspects, the cellular support system comprising a three-dimensional scaffold structure comprising at least one void and a suspended protein bridge can provide the capability to generate patient-derived tumor grafts that authentically represent the subtypes, heterogeneity, architecture, and patient-to-patient variability of breast cancer. Such grafts could provide a platform for (1) fundamental cancer studies, (2) precision medicine, and (3) pharmaceutical development and preclinical screening, by way of non-limiting example.

As described above, cFN-scaffolds make it possible to culture a bulk patient sample, where less than 5% are cancer cells, into a self-selected composition of differentiated cancer cells, stem-like cancer cells, and various stromal cells with an average of 40% increase in the tumor-initiating population after five days (n=3).

Patient microtissues grown on cFN-scaffolds can either be directly implanted into a mouse, or the cells can be removed and injected. Another option is to remove the cells, flow-sort for a particular tumorigenic phenotype, and inject only these cells into a mouse for PDX formation.

Three-dimensional tissue scaffolds prepared in accordance with certain aspects of the present disclosure, like cFN-scaffolds, can serve as a pre-culture system if other culture systems are required. As demonstrated above, Patient A cells did not survive when directly seeded onto TCPS, but grew on TCPS after culture on cFN-scaffolds. While not limiting to any particular theory, pre-culture on tissue scaffolds (e.g., cFN-scaffolds) may reduce the environmental shock on primary cells where the cFN-scaffold provides a more native or in vivo like microenvironment.

In certain other aspects, the three-dimensional scaffold structure comprising at least one void and a suspended protein bridge can provide may be able to curtail the need for animal models. Simply culturing a mixture of cell types from a patient on such scaffold structures, like cFN-scaffolds, selects for cancer and tumorigenic cells, which may be considered an ex vivo, mimics the patient tumor tissue.

The elevated population of the $ALDH^+/CD44^+/CD24^-$ fraction is hypothesized to be due to the cell source (ascites and pleural effusion), because the patient cancer cells had already metastasized, indicating the important role that this population plays in metastasis.

Without the risk of xeno-contamination, lower costs, higher-throughput, and having thus far a "tumor-take rate" of 100% at 14 out of 14 patient samples successfully cultured, cFN-scaffolds provide not only a patient-specific tissue element, but by serial propagation, a more physiologically relevant model representing human patients at large for screening of pharmaceutical compounds. Primary breast cancer patient samples cultured on three-dimensional tissue scaffolds prepared in accordance with certain aspects of the present disclosure, like cFN-scaffolds, maintain their receptor status. Therefore, the effectiveness of hormone based therapies such as letrozole or lapitinib can be tested on cells cultured on cFN-scaffolds.

In vitro model microenvironments that faithfully capture the key distinguishing features of breast cancer will be indispensable in the understanding of metastasis and development of drugs that target cells of a more stem-like or tumor-initiating phenotype. Three-dimensional tissue scaffolds prepared in accordance with certain aspects of the present disclosure, like cFN-scaffolds, can potentially meet this need, not just for breast cancer but for a variety of diseases.

The cellular support system comprising a three-dimensional scaffold structure comprising at least one void and a suspended protein bridge, such as cFN-scaffolds, can provide researchers with control of ECM composition while preserving protein biological activity, and the ability to culture primary patient cells into tissues that are otherwise a challenge to maintain in vitro.

As research shifts away from 2D monolayer cultures, the cellular support system comprising a three-dimensional scaffold structure comprising at least one void and a suspended protein bridge can address the current need for a new standard 3D cell culture system. The cellular support system comprising a three-dimensional scaffold structure comprising at least one void and a suspended protein bridge, such as cFN-scaffolds, are a biophysically and biochemically relevant 3D cell microenvironment for maintenance of both immortalized and primary cells in vitro, and can serve as an implantable tissue engineering scaffold as shown in the AT-3 tumor graft assay.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A cellular support system comprising:
   a three-dimensional scaffold structure comprising at least one void; and a suspended protein bridge in a form of a fiber spanning across the at least one void from a first surface to a second distinct surface in the three-dimensional scaffold structure wherein a first end of the fiber is anchored to the first surface and an opposite second end of the fiber is anchored to the distinct second surface, wherein the suspended protein bridge comprises an extracellular matrix protein selected from the group consisting of laminin, fibronectin, and combination thereof that is in the form of the fiber capable of supporting cells and promotes three-dimensional cellular growth.

2. The cellular support system of claim 1, wherein the void has a major dimension of greater than or equal to about 0.1 micrometers to less than or equal to about 5 centimeters.

3. The cellular support system of claim 1, wherein the suspended protein bridge further comprises one or more additional proteins selected from the group consisting of: collagen, tenascin, elastin, vitronectin, periostin, and combinations thereof.

4. The cellular support system of claim 1, wherein the three-dimensional scaffold structure is formed from a material selected from the group consisting of: a metal material, a polymeric material, a composite material, a ceramic material, a biologically-derived material, and combinations thereof.

5. The cellular support system of claim 1, wherein the three-dimensional scaffold structure comprises a polymer and is formed from a polymeric precursor or is a polymer selected from the group consisting of: polylactic acid, polyglycolide, polycaprolactone, poly(lactide-co-glycolide), poly(lactide-co-caprolactone), polyethylene glycol, starches, polydimethylsiloxane, polyurethanes, polyolefins, polyamides, celluloses, lignins, biodegradable polyesters, polystyrene, and combinations thereof.

6. The cellular support system of claim 1, wherein the three-dimensional scaffold structure has a rough surface that defines the at least one void, wherein an average surface roughness ($R_a$) of the rough surface is greater than or equal to about 0.025 micrometers.

7. The cellular support system of claim 1, wherein the three-dimensional scaffold structure comprises a polymer and a protein loading density in the cellular support system is less than or equal to about 8 milligrams of protein per milligram of polymer.

8. The cellular support system of claim 1, wherein the at least one void comprises a plurality of distinct suspended protein bridges spanning across the at least one void in the three-dimensional scaffold structure.

9. The cellular support system of claim 1, wherein the first surface and the distinct second surface respectively comprise a coating comprising a protein so as to anchor the first end of the suspended protein bridge and the opposite second end of the suspended protein bridge within the void.

10. The cellular support system of claim 1, wherein the suspended protein bridge is insoluble in water and aqueous solutions.

11. The cellular support system of claim 1, wherein the extracellular matrix protein comprises fibronectin.

12. The cellular support system of claim 11, wherein the suspended protein bridge has at least one exposed cryptic binding site.

13. A cellular support system comprising:
a three-dimensional scaffold structure comprising a plurality of voids; and
multiple voids of the plurality of voids in the three-dimensional scaffold structure respectively comprising distinct suspended protein bridges each in the form of a fiber so as to define a fibrillar network of suspended protein bridges, wherein each suspended protein bridge defines a first end of the fiber anchored to a first surface of the three-dimensional scaffold structure and an opposite second end of the fiber anchored to a distinct second surface the three-dimensional scaffold structure to span a void in the plurality of voids, wherein each suspended protein bridge comprises an extracellular matrix protein selected from the group consisting of laminin, fibronectin, and combination thereof and is capable of supporting cells and promotes three-dimensional cellular growth within the respective void in the plurality.

14. The cellular support system of claim 13, wherein a wall defined between two of the plurality of voids has an average thickness of greater than or equal to about 0.025 micrometers.

15. The cellular support system of claim 13, wherein a wall defined between two of the plurality of voids has an average thickness of greater than or equal to about 0.5 micrometers to less than or equal to about 300 micrometers.

16. The cellular support system of claim 13, wherein the first surface and the distinct second surface respectively comprise a coating comprising a protein so as to anchor the first end of the suspended protein bridge and the opposite second end of the suspended protein bridge within the void.

17. The cellular support system of claim 13, wherein the void has a major dimension of greater than or equal to about 0.1 micrometers to less than or equal to about 5 centimeters.

18. The cellular support system of claim 13, wherein the three-dimensional scaffold structure has a rough surface that defines the plurality of voids, wherein an average surface roughness ($R_a$) of the rough surface is greater than or equal to about 0.025 micrometers.

19. The cellular support system of claim 13, wherein the suspended protein bridge further comprises one or more proteins selected from the group consisting of: collagen, elastin, vitronectin, periostin, and combinations thereof.

20. The cellular support system of claim 13, wherein the three-dimensional scaffold structure is formed from a material selected from the group consisting of: a metal material, a polymeric material, a composite material, a ceramic material, a biologically-derived material, and combinations thereof.

21. The cellular support system of claim 13, wherein the three-dimensional scaffold structure comprises a polymer and is formed from a polymeric precursor or is a polymer selected from the group consisting of: polylactic acid, polyglycolide, polycaprolactone, poly(lactide-co-glycolide), poly(lactide-co-caprolactone), polyethylene glycol, starches, polydimethylsiloxane, polyurethanes, polyolefins, polyamides, celluloses, lignins, biodegradable polyesters, polystyrene, and combinations thereof.

22. The cellular support system of claim 13, wherein the three-dimensional scaffold structure comprises a polymer and a protein loading density in the cellular support system is less than or equal to about 8 milligrams of protein per milligram of polymer.

23. The cellular support system of claim 13, wherein each void of the plurality of voids respectively comprises a distinct suspended protein bridge.

24. The cellular support system of claim 13, wherein the respective suspended protein bridges are insoluble in water and aqueous solutions so that the fibrillar network is an insoluble fibrillar network of suspended protein bridges.

25. A cellular support system comprising:
- a three-dimensional scaffold structure comprising at least one void; and
- a suspended fibrillar fibronectin bridge spanning across the at least one void from a first surface to a second distinct surface in the three-dimensional scaffold structure, where a first end of the suspended fibrillar fibronectin bridge is anchored to the first surface and an opposite second end of the suspended fibrillar fibronectin bridge is anchored to the distinct second surface, wherein the suspended fibrillar fibronectin bridge has at least one exposed cryptic binding site and is capable of supporting cells and promotes three-dimensional cellular growth.

26. A method of making a cellular support system comprising:
- positioning a three-dimensional scaffold structure comprising a plurality of voids in a container at a two-phase interface comprising a liquid comprising a protein selected from the group consisting of laminin, fibronectin, and combination thereof, and a fluid; and
- passing liquid past the three-dimensional scaffold structure to dynamically incubate the protein so as to form a suspended protein bridge in a form of a fiber spanning across the at least one void by anchoring a first end of the fiber to a first surface of the three-dimensional scaffold structure and an opposite second end of the fiber to a distinct second surface of the three-dimensional scaffold structure in multiple voids of the plurality of voids so as to define a fibrillar network of suspended protein bridges, wherein each of the suspended protein bridges in the form of the fiber is capable of supporting cells and promotes three-dimensional cellular growth.

27. The method of claim 26, wherein the passing comprises moving the three-dimensional scaffold structure so that the liquid flows past the three-dimensional scaffold structure, wherein the moving is selected from the group consisting of: orbital rotation, tumbling rotation, vibration, shaking, and combinations thereof.

28. The method of claim 26, wherein the fluid is a gas that comprises air.

29. The method of claim 26, wherein the passing occurs for greater than or equal to about 5 minutes to less than or equal to about 24 hours.

30. The method of claim 26, wherein the liquid comprising protein is a protein solution having a concentration of protein from about 0.01 mg/mL to about 1 mg/mL.

31. The method of claim 26, wherein the protein is selected from the group consisting of: collagen, tenascin, elastin, vitronectin, periostin, and combinations thereof.

32. The method of claim 26, wherein the three-dimensional scaffold structure is formed from a material selected from the group consisting of: a metal material, a polymeric material, a composite material, a ceramic material, a biologically-derived material, and combinations thereof.

33. The method of claim 26, wherein the three-dimensional scaffold structure comprises a polymer and is formed from a polymeric precursor or is a polymer selected from the group consisting of: polylactic acid, polyglycolide, polycaprolactone, poly(lactide-co-glycolide), poly(lactide-co-caprolactone), polyethylene glycol, starches, polydimethylsiloxane, polyurethanes, polyolefins, polyamides, celluloses, lignins, biodegradable polyesters, polystyrene, and combinations thereof.

* * * * *

UNITED STATES PATENT AND TRADEMARK OFFICE
CERTIFICATE OF CORRECTION

PATENT NO. : 11,479,753 B2
APPLICATION NO. : 16/300499
DATED : October 25, 2022
INVENTOR(S) : Stacy Ramcharan et al.

It is certified that error appears in the above-identified patent and that said Letters Patent is hereby corrected as shown below:

On the Title Page

Page 2, Column 1, other publications, Line 8, delete "proteinmonolayer" and insert --protein monolayer--.

In the Claims

Column 43, Claim 1, Line 9, before "combination", insert --a--.

Column 44, Claim 13, Line 10, before "combination", insert --a--.

Column 45, Claim 26, Line 20, before "combination", insert --a--.

Signed and Sealed this
Twentieth Day of December, 2022

Katherine Kelly Vidal
*Director of the United States Patent and Trademark Office*